US007534580B2

(12) United States Patent  (10) Patent No.: US 7,534,580 B2
Reeves et al.  (45) Date of Patent: May 19, 2009

(54) PSP94 DIAGNOSTIC REAGENTS AND ASSAYS

(75) Inventors: Jonathan Reeves, Hawkesbury (CA); Edward Jerome Tanner, Dollard-des-Ormeaux (CA); Chandra J. Panchal, London (CA); Pierre Du Ruisseau, Laval (CA)

(73) Assignee: Ambrilia Biopharma Inc., Verdun, Quebec ( * ) Notice: Subject to any disclaimer, the term of this patent is extended or adjusted under 35 U.S.C. 154(b) by 295 days.

(21) Appl. No.: 11/154,673

(22) Filed: Jun. 17, 2005

(65) Prior Publication Data

US 2006/0029984 A1  Feb. 9, 2006

Related U.S. Application Data

(63) Continuation-in-part of application No. 10/429,668, filed on May 1, 2003.

(30) Foreign Application Priority Data

May 1, 2002  (CA) ..................................... 2380662
Jun. 25, 2002  (CA) ..................................... 2391438

(51) Int. Cl.
G01N 33/535 (2006.01)
G01N 33/543 (2006.01)
G01N 33/563 (2006.01)
G01N 33/574 (2006.01)
G01N 33/577 (2006.01)
C07K 16/18 (2006.01)
C07K 16/26 (2006.01)
C12N 5/20 (2006.01)

(52) U.S. Cl. ....................... 435/7.94; 435/7.2; 435/7.92; 435/28; 435/70.21; 435/452; 435/336; 435/337; 435/287.9; 435/975; 436/512; 436/518; 436/15; 530/388.24; 530/388.25; 530/389.2; 530/389.3; 530/391.1; 530/391.3; 530/391.7

(58) Field of Classification Search .................. 435/7.2, 435/7.94, 28, 70.21, 452, 336, 337, 975, 435/287.9, 7.92; 436/518, 15, 512; 530/388.24, 530/388.25, 389.2, 389.3, 391.1, 391.3, 391.7
See application file for complete search history.

(56) References Cited

U.S. PATENT DOCUMENTS 5,501,983 A   3/1996  Lilja et al.
6,107,103 A  * 8/2000  Xuan et al. ................. 436/518

FOREIGN PATENT DOCUMENTS

EP  03724694.9  11/2003
EP  03724694.9  8/2007
EP  03724694.9  7/2008

JP  59-038657  * 3/1984

OTHER PUBLICATIONS von der Kammer, 1990. Characterization of a monoclonal antibody specific for prostatic secretory protein of 94 amino acids (PSP94) and development of a two-site binding enzyme immunoassay for PSP94. Clinica Chimica Acta 187: 207-219.*
Huang et al., 1992. Two-site monoclonal antibody-based immunoradiometric assay for measuring prostate secretory protein in serum. Clin. Chem. 38: 817-823.*
Xuan et al., 1997. Analysis of epitope structure of PSP94 (prostate secretory protein of 94 amino acids): (II) epitope mapping by monoclonal antibodies. J. Cell. Biochem. 65: 186-197.*
Wu et al., 1999. Serum bound forms of PSP94 (prostate secretory protein of 94 amino acids) in prostate cancer patients. J. Cell. Biochem. 76: 71-83.*
Ulvsback et al., 1989. Molecular cloning of a smal prostate protein, known as beta-microseminoprotein, PSP94 or beta-inhibin, and demonstration of transcripts in non-genital tissues. Biochem. Biophys. Res. Comm. 164: 1310-1315.*
Green et al., Biochem. Biophys. Ress. Comm., 167: 1184, 1990.
Weiber et al., Am. J. Pathol., 137: 593, 1990.
Garde et al., Prostate, 22 : 225, 1993.
Lokeshwar et al., Cancer Ress. 53: 4855, 1993.
Bauman, G.S. et al., The Prostate Journal, 2: 94-101, 2000.
Puck et al., J. Exp. Med, 108: 945-956, 1958.
Buckholz et al., Bitechnology, 9: 1067-1072, 1991.
Cregg J.M. et al., Biotechnology, 11: 905-910, 1993.
Sreekrishna et al., J.Basic Microbiol., 28: 265-278, 1988.
Wegner, FEMS Microbiology Reviews, 87: 279-284, 1990.
Smith et al., Ad. Appl. Math., 2: 482-489, 1981.
Baijal Gupta et al. , Prot. Exp. And Purification 8 : 483-488, 1996.
Needleman et al., J. Mol. Biol., 48: 443-453, 1970.
Xuan J W et al., Journal of Cellular Biochemistry, 63 :61-73, 1996.
Yang J.P. et al., Journal of Urology , 160 : 2240-2244, 1998.
Gene Bank Accession No. AX. 136261; Ota et al. (seq. 183 from EP 1067182).
Catalona et al (1991) N. Engl. J. Med., 324:1156-1161.
Xuan et al (1995) Oncogene, 11:1041-1047.
Table of content of : Essential Molecular Biology: A Practical Approach, vols. 1 and 2, IRL Press (1991), D.M. Glover and B.D. Hames (editors).
Table of Content of: J. Perbal, A Practical Guide to Molecular Cloning, John Wiley and Sons (1984).
Chadwick et al (1991) Lancet, 338:613-616.
Chen et al (1995) Clin. Chem., 41:1273-1282.
Davis, B.D. (1964) Ann. N.Y. Acad. Sci., 121:404-427.
Galfrè G. and Milstein C, Meth. Enzymol. 73:3-46, 1981.

(Continued)

*Primary Examiner*—Ann Y. Lam
*Assistant Examiner*—James L Grun

(57) ABSTRACT

In the serum, PSP94 occurs as a free form or is associated with a carrier protein. PSP94 in its bound form has been quantified in the blood of prostate cancer patients and these measurements have shown utility as evaluation or prognosis of prostate cancer. Diagnostic assays, methods, and kits for detecting a free form of PSP94, and reagents such as antibodies able to bind to a free form of PSP94 are disclosed herein.

17 Claims, 21 Drawing Sheets

OTHER PUBLICATIONS

Gene Bank accession No. BC022399.
Gene Bank accession No. BC035634.
Gene Bank accession No. NM 153370.

Stenman et al (1994) Lancet, 344:1594-98.
Todaro GJ and Green H., J. Cell Biol. 17: 299-313, 1963.
von der Kammer et al (1993) Urol. Res., 21:227-233.

* cited by examiner

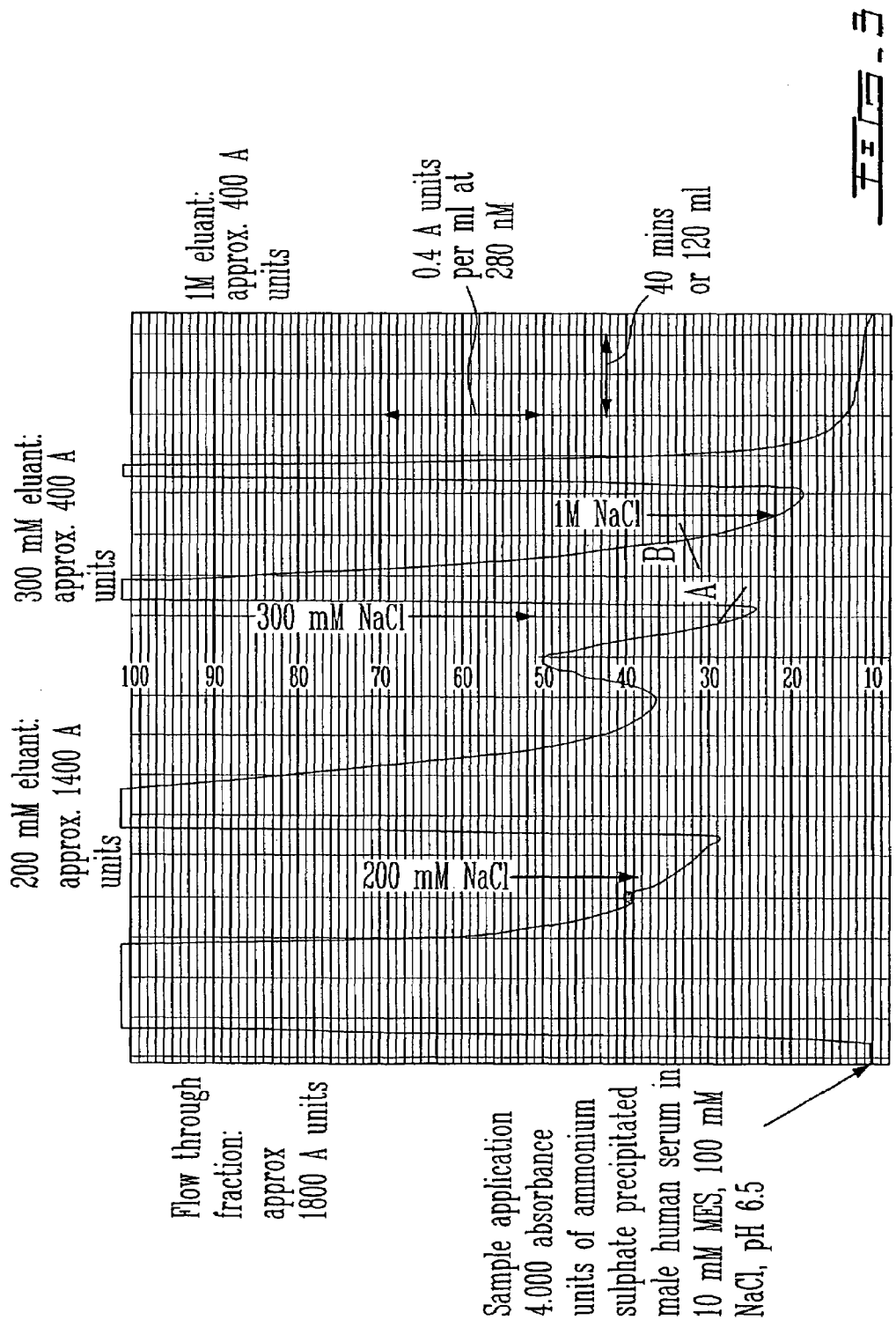

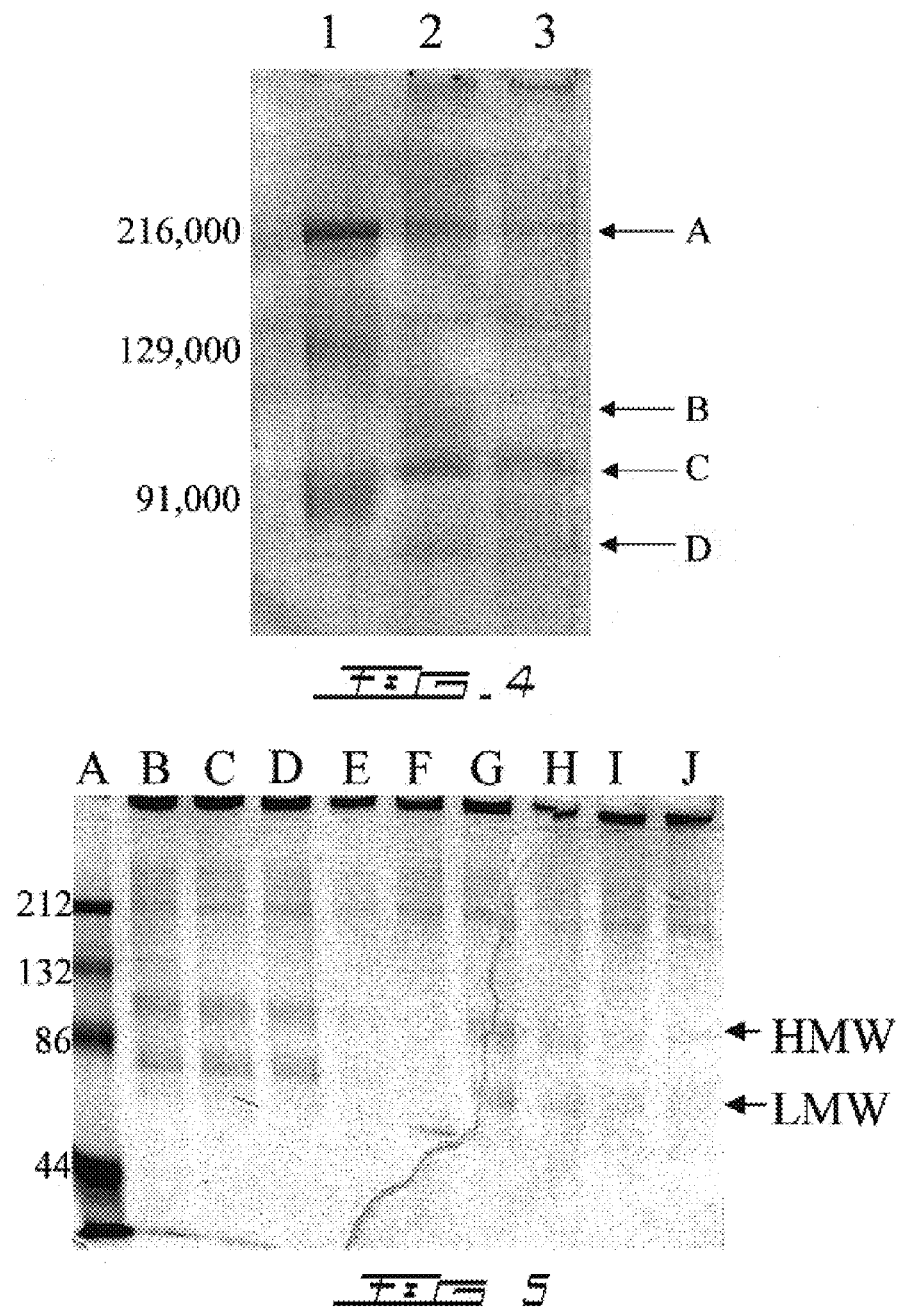

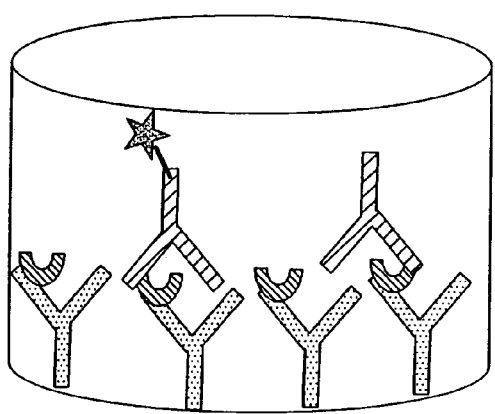
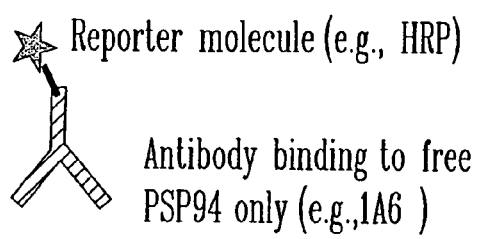 Reporter molecule (e.g., HRP)
Antibody binding to free PSP94 only (e.g.,1A6)
PSP94
Anti-PSP94 Polyclonal antibody
 FIG_12C

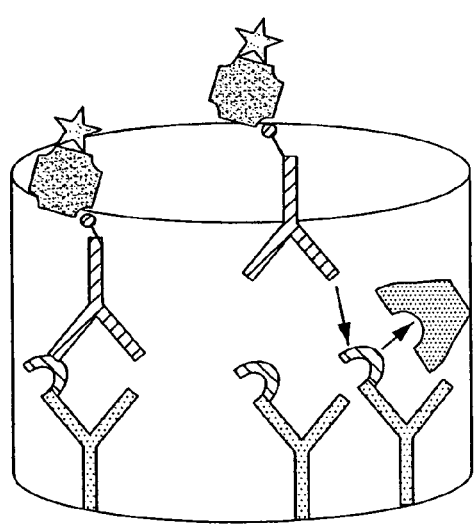
 Streptavidin peroxidase
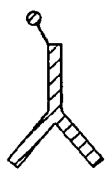 Biotinylated 2D3
 PSP94
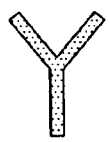 Unlabelled P1E8
 PSP94-binding protein
FIG. 13

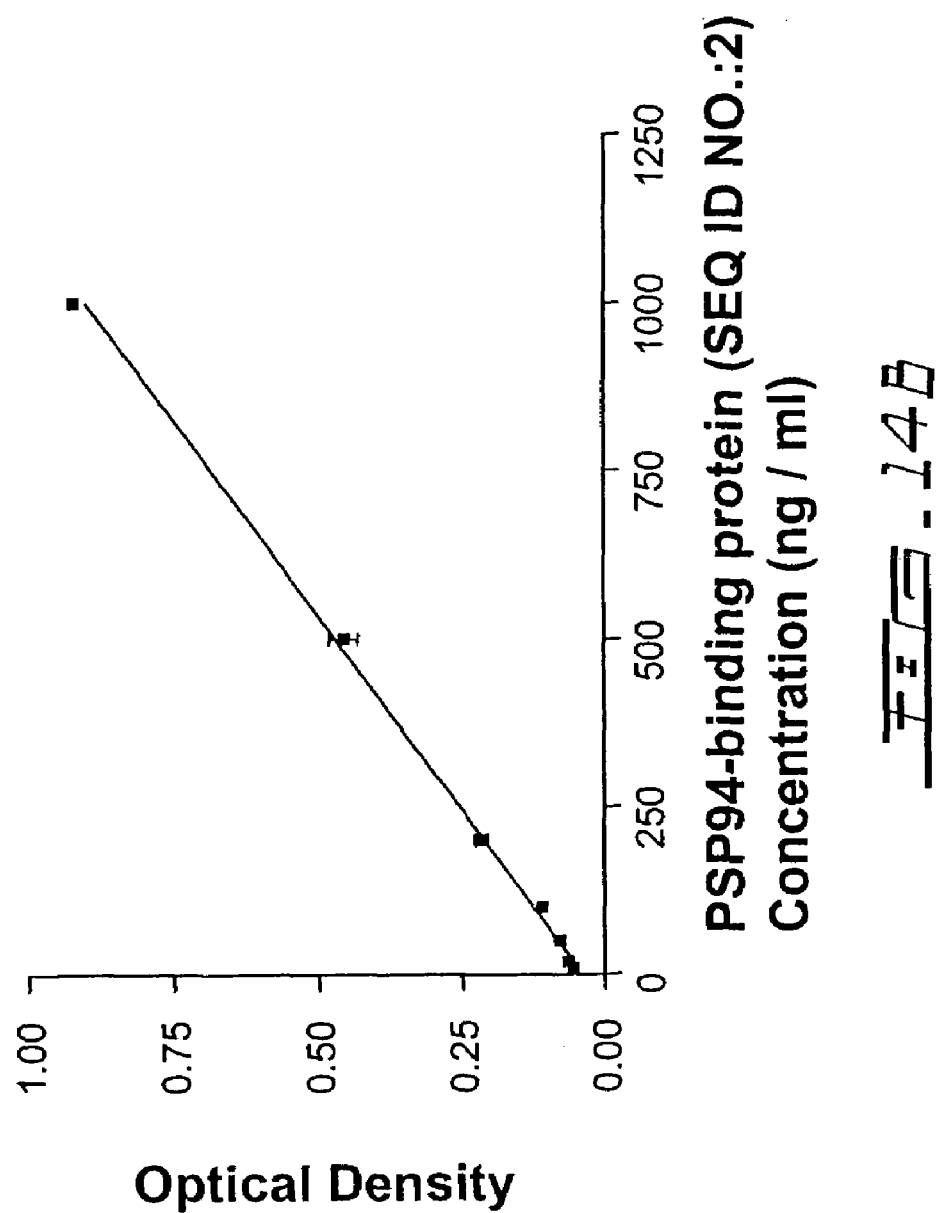

Total PSP[94]

| Range | 0.0 – 27.0 | 1.4 – 81.0 |
| Median | 4.35 | 5.89 |
| p value | 0.124 ( Mann-Whitney U test) ||

Total PSP$^{94}$

| Range | 698 – 28,975 | 1437 – 125,000 |
| --- | --- | --- |
| Median | 3,614 | 3,464 |
| p value | 0.94 (Mann-Whitney U test) | |

Total Binding Protein

Corrected Free PSP[94]

PSP94 DIAGNOSTIC REAGENTS AND ASSAYS

This application is a continuation-in-part of U.S. patent application Ser. No. 10/429,668, filed on May 1, 2003, which claims priority to Canadian Application No. 2,380,662 filed on May 1, 2002 and Canadian Application No. 2,391,438 filed on Jun. 25, 2002 the entire content of which is incorporated herein by reference.

FIELD OF THE INVENTION

This invention relates to diagnostic assays, methods, and kits for detecting a free form of PSP94, and reagents such as antibodies able to bind to a free form of PSP94.

BACKGROUND OF THE INVENTION

The prostate gland, which is found exclusively in male mammals, produces several components of semen and blood and several regulatory peptides. The prostate gland comprises stromal and epithelial cells, the latter group consisting of columnar secretory cells and basal nonsecretory cells. A proliferation of these basal cells as well as stromal cells gives rise to benign prostatic hyperplasia (BPH), which is one common prostate disease. Another common prostate disease is prostatic adenocarcinoma (CaP), which is the most common of the fatal pathophysiological prostate cancers, and involves a malignant transformation of epithelial cells in the peripheral region of the prostate gland. Prostatic adenocarcinoma and benign prostatic hyperplasia are two common prostate diseases, which have a high rate of incidence in the aging human male population.

Approximately one out of every four males above the age of 55 suffers from a prostate disease of some form or another. Prostate cancer is the second most common cause of cancer related death in elderly men, with approximately 185,000 cases diagnosed and about 39,000 deaths reported annually in the United States.

Studies of the various substances synthesized and secreted by normal, benign and cancerous prostates carried out in order to gain an understanding of the pathogenesis of the various prostate diseases reveal that certain of these substances may be used as immunohistochemical tumor markers in the diagnosis of prostate disease. The three predominant proteins or polypeptides secreted by a normal prostate gland are: (1) Prostatic Acid Phosphatase (PAP); (2) Prostate Specific Antigen (PSA); and, (3) Prostate Secretory Protein of 94 amino acids (PSP94), which is also known as Prostatic Inhibin Peptide (PIP), Human Seminal Plasma Inhibin (HSPI), or β-microseminoprotein (β-MSP), and which is hereinafter referred to as PSP94.

PSP94 is a simple non-glycosylated cysteine-rich protein, and constitutes one of three predominant proteins found in human seminal fluid along with Prostate Specific Antigen (PSA) and Prostate Acid Phosphatase (PAP). PSP94 has a molecular weight of 10.7 kDa, and the complete amino acid sequence of this protein has already been determined. The cDNA and gene for PSP94 have been cloned and characterized (Ulvsback, et al., Biochem. Biophys. Res. Comm., 164: 1310, 1989; Green, et al., Biochem. Biophys. Res. Comm., 167:1184, 1990). Immunochemical and in situ hybridization techniques have shown that PSP94 is located predominantly in prostate epithelial cells. It is also present, however, in a variety of other secretory epithelial cells (Weiber, et al., Am. J. Pathol., 137:593, 1990). PSP94 has been shown to be expressed in prostate adenocarcinoma cell line, LNCap (Yang, et al., J. Urol., 160:2240, 1998). As well, an inhibitory effect of exogenous PSP94 on tumor cell growth has been observed both in vivo and in vitro (Garde, et al., Prostate, 22:225, 1993; Lokeshwar, et al., Cancer Res., 53:4855, 1993), suggesting that PSP94 could be a negative regulator for prostate carcinoma growth via interaction with cognate receptors on tumor cells.

Native PSP94 has been shown to have a therapeutic effect in the treatment of hormone refractory prostate cancer (and potentially other prostate indications). For example, PSP94 expression within prostate cancer is known to decrease as tumor grade and agressivity increases. Tumor PSP94 expression is stimulated upon anti-androgen treatment, particularly in high grade tumors. U.S. Pat. No. 5,428,011 (Sheth A. R. et al., issued 1995-06-27), incorporated herein by reference, describes pharmaceutical preparations comprising native PSP94 used in the in-vitro and in-vivo inhibition of prostate, gastrointestinal and breast tumor growth. These pharmaceutical preparations include either native PSP94 alone or a mixture of native PSP94 and an anticancer drug such as, for example, mitomycin, idalubicin, cisplatin, 5-fluorouracil, methotrexate, adriamycin and daunomycin. In addition, the therapeutic effect of recombinant human PSP94 (rhuPSP94) and polypeptide analogues such as PCK3145 has been described in Canadian Patent Application No.: 2,359,650 (incorporated herein by reference).

Immunohistochemical studies and investigations at the level of mRNA have shown that the prostate is a major source of PSP94. PSP94 is involved in the feedback control of, and acts to suppress secretion of, circulating follicle-stimulating hormone (FSH) both in-vitro and in-vivo in adult male rats. PSP94 acts both at the pituitary as well as at the prostate site since both are provided with receptor sites for PSP94. PSP94 has been demonstrated to suppress the biosynthesis and release of FSH from the rat pituitary as well as to possibly affect the synthesis/secretion of an FSH-like peptide by the prostate. These findings suggest that the effects of PSP94 on tumor growth in vivo, could be attributed to the reduction in serum FSH levels.

Recently, it has been shown that PSP94 concentrations in serum of patients with BPH or CaP are significantly higher than normal. The highest serum concentration of PSP94 observed in normal men is approximatly 40 ng/ml, while in men with either BPH or CaP, serum concentrations of PSP94 have been observed up to 400 ng/ml.

In the serum, PSP94 occurs as a free (unbound) form or bound form associated with a carrier protein(s) of unknown identity. PSP94 in its bound form (state) has been quantified in the blood of prostate cancer patients and these measurements have been analyzed for their utility as prognostic evaluation (Bauman, G. S., et al., The Prostate J. 2:94-101, 2000; Xuan, J. W. U.S. Pat. No. 6,107,103; Wu, D. et al., J. Cell. Biochem. 76:71-83, 1999). It was suggested that measurements of the free and bound forms of PSP94 are likely to have a greater clinical relevance in several areas of prostate cancer than measurements of the free form alone. In addition, it was demonstrated that measurements of both forms of PSP94 allows an accurate prediction of relapse free interval in post-radiotherapy prostate cancer. However current assay for PSP94 measurement, such as the one described in U.S. Pat. No. 6,107,103 rely on a purification step for separating bound and free forms of the protein and therefore lack the simplicity necessary for a useful and efficient commercial assay.

SUMMARY OF THE INVENTION

Methods for evaluating (quantifying) levels of PSP94 (free or bound forms of PSP94 as well as total PSP94) are described herein. The present invention relates to antibodies having specificity for PSP94 or a PSP94-binding protein and improved diagnostic and prognostic assays, hybridomas, kits and reagents thereof.

In addition, the carrier protein(s) to which PSP94 is bound is described, identified and characterized in the present application.

Due to its ability to be associated with PSP94, a PSP94-binding protein(s) and related antibodies may have an impact on the biological activity of PSP94 and may therefore be used herein as a diagnostic and prognostic marker of (PSP94-related) disease.

More particularly, the present invention relates to an (isolated) antibody able to bind to an epitope of PSP94 which may be available when PSP94 is in a free form. For example, an (isolated) antibody of the present invention may bind to a free form of PSP94 (SEQ ID NO.:1) without being able to bind to a PSP94/PSP94-binding protein complex.

In accordance with the present invention, the antibody may be, for example, an antibody produced by the hybridoma cell line deposited to the ATCC under Patent Deposit No.: PTA-4240 or antigen binding fragments thereof. Also in accordance with the present invention, the antibody may be, for example, the antibody produced by the hybridoma cell line deposited to the ATCC under Patent Deposit No.: PTA-6599 or antigen binding fragments thereof.

Also more particularly, the present invention relates to a hybridoma cell line producing an antibody that may bind to an epitope of PSP94 which may be available when PSP94 is in a free form. Examples of hybridoma cell line which may be used for the present invention may include the hybridoma cell line deposited to the ATCC under Patent Deposit No.: PTA-4240 or the hybridoma cell line deposited to the ATCC under Patent Deposit No.: PTA-6599. Hybridomas designated PTA-4240, PTA-4241, PTA-4242 and PTA-4243 were deposited on Apr. 23, 2002 at the American Type Culture Collection (ATCC), 10801 University Blyd, Manassas, Va., 20110-2209 according to the provisions of the Budapest Treaty. The hybridoma designated PTA-6599 was deposited on Feb. 23, 2005 at the American Type Culture Collection (ATCC), 10801 University Blvd, Manassas, Va., 20110-2209, U.S.A. according to the provisions of the Budapest Treaty.

This invention also relates to polypeptides (SEQ ID NO.:2, SEQ ID NO.:3, SEQ ID NO.:7, SEQ ID NO.:8, SEQ ID NO.:9) identified herein as PSP94-binding protein(s), purification process, nucleic acid and amino acid sequence and the use of these sequences in the diagnosis, and prognosis of diseases (e.g., prostate cancer or diseases characterized by abnormal or elevated levels of PSP94 and/or follicle stimulating hormone (FSH) and/or abnormal or elevated levels of a PSP94-binding protein).

In a first aspect, the present invention provides a (e.g., isolated) polynucleotide (e.g., encoding a PSP94-binding protein), which may comprise a member selected from the group consisting of
  a) a polynucleotide as set forth in SEQ ID NO.: 1,
  b) a polynucleotide as set forth in SEQ ID NO.: 6,
  c) a polynucleotide having sequence 1 to 1392 of SEQ ID NO.:6,
  d) a polynucleotide having sequence 1 to 1653 of SEQ ID NO.:6,
  e) a polynucleotide of a size between 10 and 2005 (or 2004) bases in length identical in sequence to a contiguous portion of at least 10 bases of the polynucleotide as set forth in SEQ ID NO.: 1, and
  f) a polynucleotide of a size between 10 and 1876 (or 1875) bases in length identical in sequence to a contiguous portion of at least 10 bases of the polynucleotide as set forth in SEQ ID NO.: 6.

The polynucleotide may preferably be the polynucleotide as set forth in SEQ ID NO.:1 or the polynucleotide as set forth in SEQ ID NO.:6 or the polynucleotide having sequence 1 to 1392 of SEQ ID NO.:6 or a polynucleotide having sequence 1 to 1653 of SEQ ID NO.:6. The polynucleotide of the present invention may particularly be chosen based on the ability of the encoded protein to bind PSP94. It is to be understood herein that SEQ ID NO.:1 may be considered an analogue of SEQ ID NO.: 6.

In a second aspect, the present invention provides polypeptides and polypeptides analogues such as for example,
  a polypeptide as set forth in SEQ ID NO.: 2,
  a polypeptide as set forth in SEQ ID NO.: 3,
  a polypeptide as set forth in SEQ ID NO.: 7,
  a polypeptide as set forth in SEQ ID NO.: 8,
  a polypeptide as set forth in SEQ ID NO.: 9,
  a polypeptide of a size between 10 and 505 amino acids in length identical to a contiguous portion of the same size of SEQ ID NO.:2,
  a polypeptide of a size between 10 and 592 amino acids in length identical to a contiguous portion of the same size of SEQ ID NO.:3,
  a polypeptide of a size between 10 and 624 amino acids in length identical to a contiguous portion of the same size of SEQ ID NO.:7,
  a polypeptide analogue having at least 90% of its amino acid sequence identical to the amino acid sequence set forth in SEQ ID NO: 2, in SEQ ID NO.:3, in SEQ ID NO.:7, in SEQ ID NO: 8 or in SEQ ID NO.:9,
  a polypeptide analog having at least 70% of its amino acid sequence identical to the amino acid sequence set forth in SEQ ID NO: 2, in SEQ ID NO.:3, in SEQ ID NO.:7, in SEQ ID NO: 8 or in SEQ ID NO.:9,
  a polypeptide analog having at least 50% of its amino acid sequence identical to the amino acid sequence set forth in SEQ ID NO: 2 in SEQ ID NO.:3, in SEQ ID NO.:7, in SEQ ID NO: 8 or in SEQ ID NO.:9,
  a polypeptide analogue having at least 90% of its amino acid sequence identical to the amino acid sequence of
    a polypeptide of a length from between 10 and 505 contiguous amino acids of SEQ ID NO.:2,
    a polypeptide of a length from between 10 and 592 contiguous amino acids of SEQ ID NO.:3 or,
    a polypeptide of a length from between 10 and 624 contiguous amino acids of SEQ ID NO.:7,
  a polypeptide analogue having at least 70% of its amino acid sequence identical to the amino acid sequence of
    a polypeptide of a length from between 10 and 505 contiguous amino acids of SEQ ID NO.:2,
    a polypeptide of a length from between 10 and 592 contiguous amino acids of SEQ ID NO.:3 or,
    a polypeptide of a length from between 10 and 624 contiguous amino acids of SEQ ID NO.:7,
  a polypeptide analogue having at least 50% of its amino acid sequence identical to the amino acid sequence of
    a polypeptide of a length from between 10 and 505 contiguous amino acids of SEQ ID NO.:2, a polypeptide of a length from between 10 and 592 contiguous amino acids of SEQ ID NO.:3 or, a polypeptide of a length from between 10 and 624 contiguous amino acids of SEQ ID NO.:7.

In accordance with the present invention, the polypeptide may preferably be the polypeptide as set forth SEQ ID NO.: 2, the polypeptide as set forth SEQ ID NO.: 3, the polypeptide as set forth SEQ ID NO.:7, the polypeptide as set forth SEQ ID NO.:8 or the polypeptide as set forth SEQ ID NO.:9. The polypeptide of the present invention may particularly be chosen based on its ability to bind PSP94. It is to be understood herein that SEQ ID NO.: 2 and SEQ ID NO.: 3 may be considered analogues of SEQ ID NO.: 7. SEQ ID NO.: 8 and SEQ ID NO.:9 may also be considered analogues of SEQ ID NO.:7.

In an additional aspect, the present invention provides an immunizing composition including, for example, a vector comprising a polynucleotide as defined herein. It is sometimes preferable to have a polynucleotide of at least 21 bases in length of a desired sequence since a polypeptide of 7 amino acids (encoded by a 21 base pair polynucleotide sequence) is often associated with the major histocompatibility complex (MHC) during antigen presentation. The vector may comprise, for example, a polynucleotide selected from the group consisting of a polynucleotide as set forth in SEQ ID NO.: 1, a polynucleotide as set forth in SEQ ID NO.: 6, a polynucleotide having sequence 1 to 1392 of SEQ ID NO.:6, a polynucleotide having sequence 1 to 1653 of SEQ ID NO.:6, a polynucleotide of a size between 21 and 2005 bases in length identical in sequence to a contiguous portion of the same size of the polynucleotide set forth in SEQ ID NO.: 1 or a polynucleotide of a size between 21 and 1876, bases in length, identical in sequence to a contiguous portion of the same size of the polynucleotide set forth in SEQ ID NO.: 6, and a diluent or buffer. It is to be understood herein that the vector may enable the expression of a polypeptide encoded from the polynucleotide. The vector may be linear or circular and may contain minimal sequences in addition to the polynucleotide itself (e.g., sequence for integration into the genome, promoter, CpG sequences). Administration of a polynucleotide of the present invention (without any additional sequence, i.e, without a vector) may sometimes be sufficient to initiate a desired immune response.

In a further aspect, the present invention relates to an immunizing composition comprising a polypeptide as defined herein (e.g., SEQ ID NO.:2, SEQ ID NO.:3, SEQ ID NO.:7, SEQ ID NO.:8, SEQ ID NO.:9), a polypeptide analogue, variant, fragment or combination thereof and a diluent or a buffer. Immunization with a combination of any of the immunizing composition described herein is also encompassed by the present invention.

The immunizing composition(s) may further comprise an adjuvant. In an additional embodiment, the immunizing composition may also comprise PSP94 (native and/or recombinant), PSP94 variant, PSP94 fragment, a vector comprising a polynucleotide encoding PSP94, a polynucleotide encoding a PSP94 variant, a polynucleotide encoding a PSP94 fragment and combination thereof. Again, the vector may enable the expression of a polypeptide encoded from the polynucleotide. For reference on native PSP94, recombinant PSP94 (e.g., rHuPSP94), PSP94 variants, analogues and fragments, please see Canadian patent application No.: 2,359,650 or international patent application, published under No. WO 02/33090.

In a further aspect, the present invention relates to a method of (for) generating an antibody (monoclonal or polyclonal) to a polypeptide (e.g., PSP94, PSP94-binding protein and/or PSP94/PSP94-binding protein complex), the method comprising administering to a mammal an immunizing composition (comprising a polypeptide, polypeptide analogue, a polynucleotide and combination thereof etc.) as defined herein.

In accordance with the present invention, mammals that may be immunized using the present method include, for example, a human, a mouse, a rabbit, a sheep, a horse, a cow, a rat, a pig, and other mammals having a functional immune system. A "mammal having a functional immune system" is to be understood herein as a mammal able to produce antibodies (immunoglobulins) when immunized with an antigen (i.e., having a humoral immune response and/or a cellular immune response to the antigen).

Further aspects of the present invention relate to a monoclonal antibody produced by the hybridoma cell line deposited to the ATCC under Patent Deposit No.: PTA-4242 and antigen binding fragments thereof, to a monoclonal antibody produced by the hybridoma cell line deposited to the ATCC under Patent Deposit No.: PTA-4243 and antigen binding fragments thereof, to an hybridoma cell line deposited to the ATCC under Patent Deposit No.: PTA-4242 and to a hybridoma cell line deposited to the ATCC under Patent Deposit No.: PTA-4243.

In an additional aspect, the present invention relates to a cell that has incorporated (has been transformed, transduced, transfected, etc.) with any of the polynucleotide of the present invention e.g., SEQ ID NO.: 1, SEQ ID NO.:6, antisenses, fragments, variants, mRNA, etc.

In yet an additional aspect, the present invention relates to a (isolated) cell that has incorporated and/or that is expressing at least one of the polypeptides of the present invention, e.g., SEQ ID NO.: 2, SEQ ID NO.:3, SEQ ID NO.:7, SEQ ID NO.:8, SEQ ID NO.:9, variants, fragments, analogues or combination thereof.

In another aspect, the present invention comprises the use of a polynucleotide as defined herein (SEQ ID NO.:1, SEQ ID NO.:6, fragments, antisense, analogues, mRNA), in the diagnosis or prognosis, (or treatment) of a condition linked with abnormal (e.g., high, elevated) levels of PSP94, or with abnormal (e.g., high, elevated) levels of a PSP94-binding protein.

In yet another aspect, the present invention provides the use of the polypeptide as defined herein (e.g., SEQ ID NO.:2, SEQ ID NO.:3, SEQ ID NO.:7, SEQ ID NO.:8, SEQ ID NO.:9, analogue, variant, fragments) in the diagnosis or prognosis, (or treatment) of a condition linked with abnormal (e.g., high, elevated) levels of PSP94 or with abnormal (e.g., high, elevated) levels of a PSP94-binding protein.

In accordance with the present invention the polynucleotide defined herein or the polypeptide defined herein may be used in the diagnosis, or prognosis of a condition such as, for example, prostate cancer, stomach cancer, breast cancer, endometrial cancer, ovarian cancer, other cancers of epithelial secretion and benign prostate hyperplasia (BPH) or a disease characterized with an elevated level of FSH.

In an additional aspect, the present invention relates to a method for measuring, in a sample, the amount of a polypeptide as defined herein, for example, a polypeptide selected from the group consisting of SEQ ID NO.: 2, SEQ ID NO.: 3, SEQ ID NO.:7, SEQ ID NO.:8 and SEQ ID NO.:9 (as well variants, analogues and fragments thereof) or combination thereof. In accordance with the present invention, the method may comprise contacting the sample with a molecule (an antibody or a polypeptide) able to recognize the polypeptide. The method contemplated herein may be applied to polypeptides that are immobilized to a blot membrane, a plate, a matrix or not (in solution).

It is to be understood herein that in order to develop a quantitative assay to assess the level of a polypeptide, a preferred molecule may have sufficient affinity and specificity for the desired polypeptide. Affinity and specificity may be determined, for example, by comparing binding of the molecule to irrelevant polypeptides, by competition assays for the polypeptide of interest, etc.

In one embodiment of the present invention, the molecule used for the above described method may include, for example, the monoclonal antibody produced by the hybridoma cell line deposited to the ATCC under Patent Deposit No.: PTA-4242 and the monoclonal antibody produced by the hybridoma cell line deposited to the ATCC under Patent Deposit No.: PTA-4243. In another embodiment of the present invention, the molecule may be, for example PSP94 and analogues thereof.

The method for measuring the amount of a polypeptide selected from the group consisting of SEQ ID NO.: 2, SEQ ID NO.: 3, SEQ ID NO.:7, SEQ ID NO.:8 and SEQ ID NO.:9 contemplated herein may further comprise, for example, the following steps:
a) bringing a sample comprising at least one of the polypeptide of the present invention into contact with an antibody immobilized to a suitable substrate (e.g., ELISA plate, matrix, SDS-PAGE, Western blot membranes),
b) adding to step a) a detection reagent comprising a label or marker, and;
c) detecting a signal resulting from a label or marker.

Suitable detection reagents may comprise, for example, an antibody or a polypeptide having an affinity for a polypeptide(s) of the present invention, and the detection reagent may have preferably, a different binding site than the antibody. As described herein, the detection reagent may either be directly coupled (conjugated) to a label (or marker) or able to be recognized by a second molecule carrying (conjugated with) the label or marker.

An example of an antibody that may be used in step a) is the monoclonal antibody (17G9) produced by the hybridoma cell line deposited to the ATCC under Patent Deposit No.: PTA-4243. In that case, the monoclonal antibody (3F4) produced by the hybridoma cell line deposited to the ATCC under Patent Deposit no.: PTA-4242 may be used as a detection reagent in step c).

Any antibodies able to bind to a PSP94-binding protein (SEQ ID NO.:2, SEQ ID NO.:3, etc.), such as those antibodies listed in table 10 (identified as clones), may be used in the methods described herein (e.g., (clone) 2B10, 1B11, 9B6, P8C2, B3D1, 26B10, 1A6). When two antibodies are needed to perform the present methods it may be preferable to choose antibodies binding to different epitopes.

Another example of an antibody that may be used in step a) is the monoclonal antibody (3F4) produced by the hybridoma cell line deposited to the ATCC under Patent Deposit no.: PTA-4242. In that case the monoclonal antibody (17G9) produced by the hybridoma cell line deposited to the ATCC under Patent Deposit no.: PTA-4243 may be used as a detection reagent in step c).

In a further aspect, the present invention relates to a method for measuring, in a sample the amount of a polypeptide selected from the group consisting of SEQ ID NO.: 2, SEQ ID NO.:3, SEQ ID NO.:7, SEQ ID NO.:8 and SEQ ID NO.:9 (variants, analogues, fragments) or combination thereof, that is not bound (i.e., free (unbound)) to PSP94, the method comprising;
a) removing, from the sample, a complex formed by PSP94 and any one of the polypeptide selected from the group consisting of SEQ ID NO.: 2, SEQ ID NO.:3, SEQ ID NO.:7, SEQ ID NO.:8 and SEQ ID NO.:9 (variants, analogues, fragments) generating a complex-free sample, and;
b) contacting the complex-free sample with an antibody able to recognize any one of the polypeptide selected from the group consisting of SEQ ID NO.: 2, SEQ ID NO.:3, SEQ ID NO.:7, SEQ ID NO.:8 and SEQ ID NO.:9 (variants, analogues, fragments) and combination thereof.

In one embodiment of the present invention, the antibody used in step b) may be selected from the group consisting of the monoclonal antibody produced by the hybridoma cell line deposited to the ATCC under Patent Deposit No.: PTA-4242 and the monoclonal antibody produced by the hybridoma cell line deposited to the ATCC under Patent Deposit No.: PTA-4243.

The method for measuring the amount of the polypeptide of the present invention that is not bound to PSP94 contemplated above may, for example, comprise the following step;
a) removing, from the sample, a complex formed by PSP94 and any one of the polypeptide selected from the group consisting of SEQ ID NO.: 2, SEQ ID NO.:3, SEQ ID NO.:7, SEQ ID NO.:8 and SEQ ID NO.:9, generating a complex-free,
b) immobilizing (coating, adsorbing) an antibody to a suitable substrate (ELISA plate, matrix, SDS-PAGE, Western blot membranes),
c) adding the complex-free sample,
d) adding a detection reagent comprising a label or marker, and;
e) detecting a signal resulting from a label or marker.

The removal of the complex may be performed, for example, by using the monoclonal antibody produced by the hybridoma cell line deposited to the ATCC under Patent Deposit No.: PTA-4241.

Suitable antibodies that may be used in step b) are antibodies selected from the group consisting of the monoclonal antibody (3F4) produced by the hybridoma cell line deposited to the ATCC under Patent Deposit No.: PTA-4242 and the monoclonal antibody (17G9) produced by the hybridoma cell line deposited to the ATCC under Patent Deposit No.: PTA-4243.

In an additional aspect, the present invention includes the use of an (monoclonal) antibody selected from the group consisting of a monoclonal antibody (2D3) produced by the hybridoma cell line deposited to the ATCC under Patent Deposit No.: PTA-4240, a monoclonal antibody (P1E8) produced by the hybridoma cell line deposited to the ATCC under Patent Deposit No.: PTA-4241, a monoclonal antibody (3F4) produced by the hybridoma cell line deposited to the ATCC under Patent Deposit No.: PTA-4242 and a monoclonal antibody (17G9) produced by the hybridoma cell line deposited to the ATCC under Patent Deposit No.: PTA-4243, for evaluating (in a sample) the amount (quantity, concentrations) (free, bound, and/or total amounts) of SEQ ID NO.:2, SEQ ID NO.: 3, SEQ ID NO.:7, SEQ ID NO.:8, SEQ ID NO.:9, variants, fragments, analogues, and/or combination thereof.

In another aspect, the present invention includes the use of a molecule selected from the group consisting of a polypeptide as set forth in SEQ ID NO.:2, a polypeptide as set forth in SEQ ID NO.: 3, a polypeptide as set forth in SEQ ID NO.: 7, a polypeptide as set forth in SEQ ID NO.: 8, a polypeptide as set forth in SEQ ID NO.: 9, a monoclonal antibody (2D3) produced by the hybridoma cell line deposited to the ATCC under Patent Deposit No.: PTA-4240, a monoclonal antibody (P1E8) produced by the hybridoma cell line deposited to the ATCC under Patent Deposit No.: PTA-4241, a monoclonal antibody (3F4) produced by the hybridoma cell line deposited to the ATCC under Patent Deposit No.: PTA-4242, a monoclonal antibody (17G9) produced by the hybridoma cell line deposited to the ATCC under Patent Deposit No.: PTA-4243, and a monoclonal antibody produced by the hybridoma cell line deposited to the ATCC under Patent Deposit No.: PTA-6599, for evaluating (in a sample) the amount of PSP94 or for the diagnostic of a condition linked with abnormal or elevated levels of PSP94 or of a PSP94-binding protein.

In another aspect, the present invention relates to an antibody conjugate comprising a first moiety and a second moiety, the first moiety being selected from the group consisting of a monoclonal antibody (2D3) produced by the hybridoma cell line deposited to the ATCC under Patent Deposit No.: PTA-4240, a monoclonal antibody (P1E8) produced by the hybridoma cell line deposited to the ATCC under Patent Deposit No.: PTA-4241, a monoclonal antibody (3F4) produced by the hybridoma cell line deposited to the ATCC under Patent Deposit No.: PTA-4242 and a monoclonal antibody (17G9) produced by the hybridoma cell line deposited to the ATCC under Patent Deposit No.: PTA-4243 and the second moiety being selected from the group consisting of a pharmaceutical agent, a solid support, a reporter molecule, a group carrying a reporter molecule, a chelating agent, an acylating agent, a cross-linking agent, and a targeting group, wherein the second moiety or conjugation of the second moiety does not interfere with the biological activity (e.g., affinity, stability) of the first moiety.

In an additional aspect, the present invention relates to an antibody conjugate which may comprise a first moiety and a second moiety, the first moiety may be an antibody able to bind to an epitope of PSP94 which may be available when PSP94 is in a free form and the second moiety may be selected, for example, from the group consisting of a pharmaceutical agent, a solid support, a reporter molecule, a group carrying a reporter molecule, a chelating agent, an acylating agent, a cross-linking agent, and a targeting group.

In accordance with the present invention, the solid support may be selected, for example, from the group consisting of carbohydrates, liposomes, lipids, colloidal gold, microparticles, microcapsules, microemulsions, and a solid matrix.

Also in accordance with the present invention, the reporter molecule may be selected, for example, from the group consisting of a fluorophore, a chromophore, a dye, an enzyme, a radioactive molecule and a molecule of a binding/ligand complex.

Further in accordance with the present invention, the pharmaceutical agent may be selected, for example, from the group consisting of a toxin, a drug and a pro-drug.

More particulalry, in accordance with the present invention, the first moiety may be, for example, an antibody produced by a hybridoma cell line deposited to the ATCC under Patent Deposit No.: PTA-4240 or may be an antibody produced by a hybridoma cell line deposited to the ATCC under Patent Deposit No.: PTA-6599.

In one embodiment of the present invention, examples of solid support may comprise, for example, carbohydrates, liposomes, lipids, colloidal gold, microparticles, microcapsules, microemulsions, and the matrix of an affinity column.

In an additional embodiment, reporter molecule may be selected from the group consisting of a fluorophore (e.g., rhodamine, fluoroscein, and green fluorescent protein), a chromophore, a dye, an enzyme (e.g., alkaline phosphatase, horseradish peroxidase, beta-galactosidase, chloramphenicol acetyl transferase), a radioactive molecule and a molecule of a binding/ligand (e.g., biotin/avidin (streptavidin)) complex.

In yet an additional embodiment, the pharmaceutical agent may be selected from the group of a toxin (e.g., bacterial toxins), a (e.g., anti-cancer) drug and a pro-drug.

In a further aspect, the present invention includes a kit for use in evaluating (in a sample) the amount of PSP94 or for the diagnosis of a condition linked with abnormal (e.g., high, elevated) levels of PSP94 (or of a PSP94-binding protein) comprising a container having a molecule able to recognize (bind) PSP94. It is to be understood herein that the kit may be provided (sold) in separate constituents.

In one embodiment of the present invention, the molecule able to recognize PSP94 that may be included in the kit, may (comprise, for example) be a molecule selected from the group consisting of (one or more of the following) a monoclonal antibody (2D3) produced by the hybridoma cell line deposited to the ATCC under Patent Deposit No.: PTA-4240, a monoclonal antibody (P1E8) produced by the hybridoma cell line deposited to the ATCC under Patent Deposit No.: PTA-4241, a monoclonal antibody (3F4) produced by the hybridoma cell line deposited to the ATCC under Patent Deposit No.: PTA-4242, a monoclonal antibody (17G9) produced by the hybridoma cell line deposited to the ATCC under Patent Deposit No.: PTA-4243, the antibody conjugate(s) of the present inventions and a polypeptide selected from the group consisting of SEQ ID NO.:2, SEQ ID NO.:3, SEQ ID NO.:7, SEQ ID NO.:8 and SEQ ID NO.:9.

In another embodiment of the present invention, the kit may further comprise a container having an antibody able to recognize (bind) a polypeptide selected from the group consisting of the polypeptide set forth in SEQ ID NO.:2, the polypeptide set forth in SEQ ID NO.:3 and the polypeptide set forth in SEQ ID NO.:7, the polypeptide set forth in SEQ ID NO.:8, the polypeptide set forth in SEQ ID NO.:8, variant, fragment, analogues and combination thereof. Contemplated by the present invention are the monoclonal antibody (17G9) produced by the hybridoma cell line deposited to the ATCC under Patent Deposit No.: PTA-4243 and a monoclonal antibody (3F4) produced by the hybridoma cell line deposited to the ATCC under Patent Deposit No.: PTA-4242.

It is to be understood herein that kits may be provided in separate constituents. The antibodies provided with the kit may be in different forms such as bound to plates or membranes or other type of solid matrix or in vials containing concentrated forms or suitable working dilutions of the antibodies.

More particularly, the present invention relates to a kit comprising an antibody (a first antibody) which is able to bind to an epitope of PSP94 which may be available when PSP94 is in a free form.

In accordance with the present invention, the kit may be use in evaluating the amount of PSP94 or for the diagnosis of a condition linked with abnormal or elevated levels of PSP94. The kit may comprise a container having a molecule able to recognize PSP94.

In accordance with the present invention, the antibody used in the kit may be conjugated, for example, with a reporter molecule. The reporter molecule may be, for example, an enzyme such as a peroxidase (e.g., horseradish peroxidase).

Also in accordance with the present invention, the kit may further comprise a control sample containing a known (predetermined) amount of PSP94 (for example in a substantially purified form). Suitable (first) antibody which may be used in the kit of the present invention includes, for example, the antibody produced by the hybridoma cell line deposited to the ATCC under Patent Deposit No.: PTA-6599.

Further in accordance with the present invention, the kit may also comprise a second antibody which may bind to a different epitope of PSP94 or may alternatively comprise a polyclonal antibody which binds to PSP94. The second antibody may be, for example, the antibody produced by a hybridoma cell line deposited to the ATCC under Patent Deposit No.: PTA-4240.

Alternatively, another suitable (first) antibody which may be used in the present invention includes an antibody produced by the hybridoma cell line deposited to the ATCC under Patent Deposit No.: PTA-4240. In accordance with the present invention, the kit may further comprise a second antibody which may bind to a different epitope of PSP94 or alternatively, the kit may further comprise a polyclonal antibody which may bind to PSP94.

It is to be understood herein that one of the antibody of the kits may be bound to a solid matrix (e.g., a plate, a membrane, etc.). Any unspecific binding sites of the solid matrix may also be blocked (using bovine serum albumin, milk protein, etc.) if desired.

The present invention, more particularly relates to a kit which may comprise a first and second antibody which binds to PSP94. In accordance with the present invention, at least one of the first or second antibody may bind to a free form of PSP94 (only). Also in accordance with the present invention, the first and second antibody may bind to a different epitope of PSP94.

In accordance with the present invention, the kit may comprise a control sample which may contain a known (predetermined) amount of PSP94 (for example, in a substantially purified form).

In accordance with the present invention, the first antibody may be selected, for example, from the group consisting of a polyclonal antibody, an antibody produced by a hybridoma cell line deposited to the ATCC under Patent Deposit No.: PTA-4240, an antibody produced by a hybridoma cell line deposited to the ATCC under Patent Deposit No.: PTA-4241 and an antibody produced by the hybridoma cell line deposited to the ATCC under Patent Deposit No.: PTA-6599. The second antibody may be selected, for example, from the group consisting of a polyclonal antibody, an antibody produced by the hybridoma cell line deposited to the ATCC under Patent Deposit No.: PTA-4240, an antibody produced by a hybridoma cell line deposited to the ATCC under Patent Deposit No.: PTA-4241 and an antibody produced by the hybridoma cell line deposited to the ATCC under Patent Deposit No.: PTA-6599.

In accordance with the present invention, the first antibody may be a polyclonal antibody and the second antibody may be selected, for example, from the group consisting of an antibody produced by a hybridoma cell line deposited to the ATCC under Patent Deposit No.: PTA-6599 and an antibody produced by a hybridoma cell line deposited to the ATCC under Patent Deposit No.: PTA-4240.

In accordance with the present invention, the first antibody may be produced by the hybridoma cell line deposited to the ATCC under Patent Deposit No.: PTA-4241 and the second antibody may be selected, for example, from the group consisting of an antibody produced by a hybridoma cell line deposited to the ATCC under Patent Deposit No.: PTA-6599 and an antibody produced by a hybridoma cell line deposited to the ATCC under Patent Deposit No.: PTA-4240.

In accordance with the present invention, the second antibody may be conjugated with a reporter molecule. Also in accordance with the present invention, the reporter molecule may be, for example, an enzyme such as a peroxidase (e.g., horseradish peroxidase).

In another aspect, the present invention provides a method for preparing a polypeptide as defined herein (a PSP94-binding protein, e.g., a polypeptide selected from the group consisting of the polypeptide set forth in SEQ ID NO.:2, the polypeptide set forth in SEQ ID NO.:3, the polypeptide set forth in SEQ ID NO.:7, the polypeptide set forth in SEQ ID NO.:8 and the polypeptide set forth in SEQ ID NO.:9) comprising:
  a) cultivating a host cell under conditions which provide for the expression of the polypeptide by the cell; and
  b) recovering the polypeptide by one or more purification step.

In yet another aspect, the present invention provides a method for preparing the polypeptide as defined herein (a PSP94-binding protein, e.g., a polypeptide selected from the group consisting of the polypeptide set forth in SEQ ID NO.:2, the polypeptide set forth in SEQ ID NO.:3, the polypeptide set forth in SEQ ID NO.:7 the polypeptide set forth in SEQ ID NO.:8, the polypeptide set forth in SEQ ID NO.:9 and combination thereof) comprising:
  a) collecting one or more biological sample containing the polypeptide; and
  b) recovering the polypeptide by one or more purification step.

It is to be understood herein that the purification step either alone or in combination may be selected from the group consisting of ammonium sulfate precipitation, size exclusion chromatography, affinity chromatography, ion-exchange chromatography or the like.

In another embodiment of the present invention, the purification step may comprise;
  a) adding ammonium sulfate to the biological sample,
  b) performing ion-exchange chromatography,
  c) performing affinity-chromatography using a PSP94-conjugated affinity matrix,
  d) performing size-exclusion chromatography, and
  e) recovering a fraction containing a substantially pure PSP94-binding protein.

In a further aspect, the present invention also includes a process for the purification of a PSP94-binding protein from a sample comprising:
  a) adding ammonium sulfate to the sample (e.g., human male serum) in a manner as to provide precipitation of a PSP94-binding protein,
  b) centrifuging the mixture of step a) to recover precipitated proteins,
  c) resuspending the precipitated proteins,
  d) performing ion-exchange chromatography to recover a fraction of proteins containing a PSP94-binding protein,
  e) performing affinity-chromatography using a PSP94-conjugated affinity matrix to recover a fraction of proteins containing a PSP94-binding protein,
  f) performing size exclusion chromatography to recover a fraction of proteins containing a PSP94-binding protein and;
  g) recovering a fraction containing a substantially pure PSP94-binding protein (e.g., a polypeptide selected from the group consisting of the polypeptide defined in SEQ ID NO.:2, the polypeptide defined in SEQ ID NO.:3, the polypeptide defined in SEQ ID NO.:7, the polypeptide set forth in SEQ ID NO.:8, the polypeptide set forth in SEQ ID NO.:9 and combination thereof.

In one embodiment of the present invention, the precipitation of a PSP94-binding protein in step a) may be effected by adding ammonium sulfate to a final concentration of up to 47%.

In a second embodiment of the present invention, the ion-exchange chromatography of step d) may be performed by using an anion-exchange chromatography matrix.

The present invention in a further aspect thereof comprises a purification process for a PSP94-binding protein (e.g., a polypeptide selected from the group consisting of the polypeptide defined in SEQ ID NO.:2, the polypeptide defined in SEQ ID NO.:3, the polypeptide defined in SEQ ID NO.:7, the polypeptide defined in SEQ ID NO.:8, the polypeptide defined in SEQ ID NO.:9 and combination thereof) (summarized in FIG. 8). The purification of a PSP94-binding protein from serum may comprise, for example, the following steps:
a) adding ammonium sulfate to a human (male) serum sample to provide a solution with a final concentration of ammonium sulfate of 32%,
b) centrifuging the solution of the previous step to recover a pellet fraction of proteins containing unspecific human serum proteins and a supernatant fraction of proteins containing a PSP94-binding protein,
c) recovering the supernatant fraction of proteins containing a PSP94-binding protein and adjusting the concentration of ammonium sulfate to a final concentration of 47% to provide a solution of precipitated proteins containing a PSP94-binding protein,
d) centrifuging the mixture to recover precipitated proteins containing a PSP94-binding protein,
e) resuspending the precipitated proteins containing a PSP94-binding protein in an aqueous media (e.g., water, phosphate buffered saline, 10 mM MES, 10 mM MOPS, 10 mM Bicine: these solution (when applicable) may be at a pH comprised, for example, between 4.7 and 9.0, preferably between 5.7 and 8.0 and more preferably between 5.7 and 6.7) However a preferred aqueous media is 10 mM MES buffer at a pH of 6.5,
f) loading (contacting, charging) the aqueous solution of proteins containing a PSP94-binding protein in an ion-exchange (anion-exchange) chromatography column containing an ion-exchange (anion-exchange) chromatography matrix (resin, gel),
g) adding a salt solution selected from the group consisting of sodium chloride, magnesium chloride, potassium chloride to recover (elute, detach) proteins containing a PSP94-binding protein from the ion-exchange chromatography column, preferably sodium chloride with a molarity ranging from, for example, 100 mM to 1000 mM,
h) recovering a fraction (peak) of proteins containing a PSP94-binding protein,
i) contacting (charging, passing through) a PSP94-conjugated affinity matrix with the fraction recovered in order to generate a PSP94-conjugated affinity matrix bound to a PSP94-binding protein,
j) adding an eluting reagent (free PSP94, urea, sodium acetate or CAPS; preferably free PSP94) to the PSP94-conjugated affinity matrix bound to a PSP94-binding protein to recover (elute, detach) a PSP94-binding protein,
k) recovering a fraction containing a PSP94-binding protein,
l) loading the PSP94-binding protein in a size exclusion chromatography column containing a size exclusion chromatography matrix to separate PSP94-binding protein from contaminants, and;
m) recovering a fraction containing a (substantially) pure PSP94-binding protein.
It is to be understood that some of the purification steps described herein may prove to be unnecessary depending on the level of purification required or depending on the optimization of one or more of the remaining steps.

In a further aspect, the present invention relates to the product obtained from the purification process defined above.

In accordance with the present invention, samples (e.g., biological sample) referred herein may comprise, for example, blood, plasma, serum, urine, seminal fluid, cell culture media, cell lyzate, etc. The sample is preferably a human (e.g., male) sample.

In another aspect, the present invention relates to an antibody, and antigen binding fragments thereof, able to recognize a PSP94 epitope (i.e., exposed epitope) that is available even when PSP94 is bound to another polypeptide (another molecule). Such polypeptide may be for example, a polypeptide selected from the group consisting of SEQ ID NO.: 2, SEQ ID NO.: 3, SEQ ID NO.: 7, SEQ ID NO.:8, SEQ ID NO.:9, variant, fragment, analogue and combination thereof. The hybridoma cell line producing such antibody is also contemplated by the present invention. An example of such antibody is the monoclonal antibody produced by the hybridoma cell line deposited to the ATCC under Patent Deposit NO.: PTA-4241 (P1E8) or a polyclonal antibody able to recognize free and bound forms of PSP94.

The identification of an exposed epitope may be performed by testing a panel of antibody for their specificity to free and bound forms of PSP94. Antibodies which react (recognize) with both forms may represent candidate antibodies. In parallel, partial trypsin digestion may be performed on the PSP94/PSP94-binding protein complex. PSP94 epitopes (e.g., linear epitopes) available in the complexed forms may then be identified by amino acid sequence analysis. Antibodies able to bind to this or these (available) epitope(s) may be generated. Exposed epitopes are to be understood herein, as epitopes of a molecule (e.g., PSP94, SEQ ID NO.:2, SEQ ID NO.:3. SEQ ID NO.: 7, SEQ ID NO.:8, SEQ ID NO.:9 and their complex) that are accessible to an antibody, preferably when the molecule(s) or complex is in its native (natural) state (e.g., non-denatured, natural or 3D form).

In a further aspect, the present invention provides a method for removing PSP94 from a sample, the method comprising
a) contacting the sample with a molecule able to bind to PSP94 (the molecule may be directly or indirectly bound to a matrix or solid support) and;
b) recuperating a sample free of PSP94.

It may prove useful to remove PSP94 from a sample (biological sample) for example, removing excess PSP94 from serum of individuals (i.e., serum depletion of PSP94) having elevated levels of PSP94 and to reinfuse a depleted serum into the individual (e.g., patient in need). In other instance, it may be useful to remove PSP94 from a sample in order to optimize measurement of other serum constituents. Removal of PSP94 is based on the affinity between PSP94 and any one of the sequence set forth in SEQ ID NO.: 2, SEQ ID NO.: 3, SEQ ID NO.: 7, SEQ ID NO.: 8, SEQ ID NO.: 9, PSP94 antibodies, and combination thereof.

The molecule referred above may be selected from the group consisting of SEQ ID NO.: 2, SEQ ID NO.:3, SEQ ID NO.: 7, SEQ ID NO.:8, SEQ ID NO.: 9, a monoclonal antibody produced by the hybridoma cell line deposited to the ATCC under Patent Deposit No.: PTA-4240 and a monoclonal antibody produced by the hybridoma cell line deposited to the ATCC under Patent Deposit No.: PTA-4241.

In yet a further aspect, the present invention provides a method for removing a complex formed by PSP94 and any one of the polypeptide defined in SEQ ID NO: 2, SEQ ID NO.:3, SEQ ID NO.:7, SEQ ID NO.:8, SEQ ID NO.:9 and combination thereof (e.g., PSP94/SEQ ID NO:2 and/or PSP94/SEQ ID NO.:3 and/or PSP94/SEQ ID NO:7, etc.) from a sample, the method comprising;

a) contacting the sample with an antibody able to recognize an available (exposed) epitope of the complex (e.g., the antibody may be directly or indirectly bound to a matrix or solid support) and;
b) recuperating a sample free of the complex.

In one embodiment of the present invention, the antibody used in step b) may comprise, for example, a monoclonal antibody produced by the hybridoma cell line deposited to the ATCC under Patent Deposit No.: PTA-4241, a monoclonal antibody produced by the hybridoma cell line deposited to the ATCC under Patent Deposit No.: PTA-4242 and a monoclonal antibody produced by the hybridoma cell line deposited to the ATCC under Patent Deposit No.: PTA-4243. Preferably used is the monoclonal antibody produced by the hybridoma cell line deposited to the ATCC under Patent Deposit No.: PTA-4243.

Other aspects of the present invention encompass the antibody produced by the hybridoma cell line deposited to the ATCC under Patent Deposit (e.g., Accession) No.: PTA-4240, the monoclonal antibody produced by the hybridoma cell line deposited to the ATCC under Patent Deposit (e.g., Accession) No.: PTA-4241 as well as antibody produced by the hybridoma cell line deposited to the ATCC under Patent Deposit No.: PTA-6599 and antigen binding fragments thereof.

Also covered by the present invention are the hybridoma cell lines producing the antibodies described herein. These include the hybridoma cell line deposited to the ATCC under Patent Deposit (e.g., Accession) No.: PTA-4240, the hybridoma cell line deposited to the ATCC under Patent Deposit (e.g., Accession) No.: PTA-4241 and the hybridoma cell line deposited to the ATCC under Patent Deposit No. PTA-6599.

In another aspect, the present invention provides a method for measuring, in a sample, the total amount of PSP94, the method may comprise contacting the sample with an antibody able to recognize PSP94 even when PSP94 is bound to another polypeptide (such as for example, SEQ ID NO.:2, SEQ ID NO.:3. SEQ ID NO.:7, SEQ ID NO.:8, SEQ ID NO.:9 variants, fragments and analogues). This aspect of the invention encompasses any method which comprises this step, irrelevant of the fact that one or more steps are to be performed or not.

In one embodiment, the antibody that may be used in measuring the total amount of PSP94 in a sample, may be, for example, the monoclonal antibody produced by the hybridoma cell line deposited to the ATCC under Patent Deposit No.: PTA-4241 or it may be a polyclonal antibody able to recognize free and bound forms of PSP94.

The method for measuring total (free (unbound) and bound) amount of PSP94 in a sample contemplated above may comprise the following steps;
a) immobilizing (coating, adsorbing) a PSP94-antibody to a suitable substrate (ELISA plate, matrix, SDS-PAGE, Western blot membranes). The antibody may be able to recognize PSP94 even when bound to a PSP94-binding protein (such as SEQ ID NO.:2, SEQ ID NO.:3, SEQ ID NO.:7, SEQ ID NO.:8, SEQ ID NO.:9);
b) adding a sample comprising PSP94,
c) adding a PSP94 detection reagent comprising a label or marker, and;
d) detecting a signal resulting from a label or marker.

Examples of suitable detection reagents that may be used in step c) of the present method, include an antibody and a polypeptide having an affinity for PSP94. However, the detection reagent may preferably have a different binding site than the PSP94-antibody and a PSP94-binding protein. The detection reagent may either be directly coupled to a label (or marker) (e.g., antibody conjugate of the present invention) or able to be recognized by a second molecule carrying (conjugated with) the label or marker.

An example of a PSP94-antibody that may be used in step a) is the antibody (P1E8) produced by the hybridoma cell line deposited to the ATCC under Patent Deposit no.: PTA-4241. In that case, the detection reagent may be, for example, the antibody (2D3) (e.g., antibody-conjugate) produced by the hybridoma cell line deposited to the ATCC under Patent Deposit no.: PTA-4240 or any other suitable PSP94 antibody.

It is to be understood herein that a polyclonal antibody (one or more polyclonal antibodies) able to recognize free and bound forms of PSP94 may be suitable for any of steps a) or c) in combination with any of the monoclonal antibody described herein. For example, total PSP94 may be captured with a polyclonal antibody (an antibody able to recognize free and bound forms of PSP94) and detection may be performed (directly or indirectly) with another antibody such as P1E8 (and vice versa).

In addition, total PSP94 may be captured with an antibody able to recognize PSP94 in its free and bound forms (e.g., bound to a PSP94-binding protein as described herein), such as, for example, a polyclonal antibody or the P1E8 antibody (produced by the hybridoma cell line PTA-4241), and detection of the captured proteins (complex) may be performed with a combination of two or more antibodies i.e., one able to detect the free PSP94 (e.g., 2D3 produced by hybridoma cell line PTA-4240) and one or more antibodies able to detect PSP94-binding protein (e.g., 17G9 produced by the hybridoma cell line PTA-4243; and/or 3F4 produced by the hybridoma cell line PTA-4242).

In yet another aspect, the present invention provides an improved method for measuring the amount of free PSP94 in a sample, the method comprising contacting the sample with an antibody able to recognize PSP94 (e.g., in its free form).

More particularly, the present invention relates to a method for measuring the amount of free PSP94 in a sample, the method may comprise contacting the sample with an antibody able to recognize PSP94 (a free form of PSP94).

Also more particularly, the present invention relates to a method for detecting or measuring a free form of PSP94 in a sample, the method may comprise for example,
  contacting the sample with an antibody of the present invention (e.g., an antibody able to bind to an epitope of PSP94 which is available when PSP94 is in a free form) and;
  detecting a signal from a label that is provided by the antibody or by a second molecule carrying the label.

In accordance with the present invention, suitable antibody used with the method of the present invention includes the antibody produced by a hybridoma cell line deposited to the ATCC under Patent Deposit No.: PTA-4240 antigen binding fragments thereof ot the antibody produced by a hybridoma cell line deposited to the ATCC under Patent Deposit No.: PTA-6599 and antigen binding fragments thereof.

In accordance with the present invention, the signal obtained for the sample may be compared with a signal obtained for a control sample containing a predetermined amount of PSP94.

The present invention also relates to a method for detecting or measuring a free form of PSP94 in a sample, the method may comprise:
  contacting the sample with a first antibody able to bind to PSP94;
  contacting the sample with a second antibody which may bind to an epitope of PSP94 which is available when PSP94 is in a free form; and detecting a signal from a label coupled to the second antibody or from a label provided by a third antibody carrying the label.

In accordance with the present invention, the first and second antibody may bind to a different PSP94 epitope.

In accordance with the present invention, the first antibody may be selected, for example, from the group consisting of a polyclonal antibody, an antibody produced by a hybridoma cell line deposited to the ATCC under Patent Deposit No.: PTA-4240 and an antibody produced by a hybridoma cell line deposited to the ATCC under Patent Deposit No.: PTA-6599.

In accordance with the present invention, the first antibody may be a polyclonal antibody and the second antibody may be an antibody produced by the hybridoma cell line deposited to the ATCC under Patent Deposit No.: PTA-4240.

Also in accordance with the present invention, the first antibody may be a polyclonal antibody and the second antibody may be an antibody produced by the hybridoma cell line deposited to the ATCC under Patent Deposit No.: PTA-6599.

Further in accordance with the present invention, the sample may be selected, for example, from the group consisting of blood, plasma, serum, urine, seminal fluid, cell culture media and cell lyzate.

In an additional aspect, the present invention relates to a method for detecting or measuring a free form of PSP94 in a sample, the method may comprise:
    contacting the sample with a first antibody which may be able to bind to an epitope of PSP94 which is available when PSP94 is in a free form;
    contacting the sample with a second antibody which may be able to bind to PSP94; and
    detecting a signal from a label coupled to the second antibody or from a label provided by a third antibody carrying the label, Further in accordance with the present invention, the first and second antibody may bind to a different PSP94 epitope.

In accordance with the present invention, the first antibody may be an antibody produced by a hybridoma cell line deposited to the ATCC under Patent Deposit No.: PTA-4240 and the second antibody may be selected from the group consisting of a polyclonal antibody, an antibody produced by a hybridoma cell line deposited to the ATCC under Patent Deposit No.: PTA-4241 and an antibody produced by a hybridoma cell line deposited to the ATCC under Patent Deposit No.: PTA-6599.

Also in accordance with the present invention, the first antibody may be an antibody produced by a hybridoma cell line deposited to the ATCC under Patent Deposit No.: PTA-6599 and the second antibody may be selected from the group consisting of a polyclonal antibody, an antibody produced by a hybridoma cell line deposited to the ATCC under Patent Deposit No.: PTA-4241 and an antibody produced by a hybridoma cell line deposited to the ATCC under Patent Deposit No.: PTA-4240.

In a further aspect, the present invention relates to a method for detecting or measuring a free form of PSP94 in a sample, the method may comprise contacting the sample with an antibody conjugate able to bind to an epitope of PSP94 which may be available when PSP94 is in a free form. The antibody conjugate may comprise a first moiety and a second moiety. The first moiety may be an antibody able to bind to an epitope of PSP94 which may be available when PSP94 is in a free form and the second moiety may be selected from the group consisting of a reporter molecule and a group carrying a reporter molecule.

In yet a further aspect, the present invention relates to a method for measuring free PSP94 in a sample, the method may comprise contacting the sample with a first antibody and second antibody. Each of the first antibody and second antibody may be able to bind to a different epitope of PSP94. In accordance with the present invention at least one of the first antibody and second antibody may bind to PSP94 in its free form only.

In an embodiment of the present invention, suitable antibodies may include for example, the monoclonal antibody produced by the hybridoma cell line deposited to the ATCC under Patent Deposit No.: PTA-4240 and the monoclonal antibody produced by the hybridoma cell line deposited to the ATCC under Patent Deposit No.: PTA-4241. However, other suitable antibodies are encompassed by the present invention, such as the 12C3 antibody (Table 10).

Any of the antibodies binding to PSP94 described herein may be used to detect PSP94 in other types of assays such as immunohistochemistry, Western blot, etc. For example a tissue section (e.g., from a prostate) which comprises PSP94 expressing cells may be contacted with one of the anti-PSP94 antibody of the present invention and the presence of PSP94 is assessed by detecting a signal from a label carried by the anti-PSP94 antibody. The presence of PSP94 may also be assessed by detecting a signal, for example, from a label carried by a second antibody able to bind to the anti-PSP94 antibody. An example of a suitable second antibody is an anti-mouse IgG (e.g., anti-mouse $IgG_1\kappa$) for the monoclonal antibodies (e.g., 1A6, 2D3, 12C3, P1E8, etc.) or for the anti-PSP94 polyconal antibody, an anti-rabbit antibody (e.g., anti rabbit IgG). It is to be understood herein that the anti-PSP94 antibodies described herein are able to recognize human PSP94.

An example of an immunodetection assay (a sandwich ELISA assay measuring free PSP94) may be performed with an antibody able to recognize PSP94 coated onto the wells of an ELISA plate which is contacted with a sample containing PSP94. A second antibody able to bind to an epitope of PSP94 available when PSP94 is in a free form may be added and detection may be performed. The second antibody may carry a reporter molecule. In this type of assay, two antibodies are used; (a first antibody and a second antibody) each one may be able to bind a different epitope of PSP94. It is to be understood that the first and second antibody may be interchanged without affecting the results. One of the first or second antibody may be an antibody able to bind to PSP94 in its free form only (e.g., not in a form bound to a PSP94 binding protein described herein).

For example, the first antibody may be an antibody able to bind to all forms of PSP94 (bound and free, for example, a polyclonal antibody) and the second antibody may be an antibody able to bind to the free form of PSP94 only (i.e., an antibody able to bind to an epitope of PSP94 which is available when PSP94 is in a free form only, i.e., the antibody may bind to an epitope of PSP94 which is masked when PSP94 is bound (e.g., to a PSP94 binding protein described herein)). Therefore although all forms of PSP94 are captured by the first antibody, only the free form of PSP94 may be detected by the second antibody in this type of assay.

Alternatively, the first antibody may be an antibody which may bind to the free form of PSP94 only (1A6), as described herein, and the second antibody may be an antibody which may bind to all (every) form of PSP94 (bound and unbound). As the first antibody captures only the free form of PSP94 and the bound form is not retained, the second antibody may detect the free form of PSP94 only.

Also alternatively, the first antibody may be an antibody which binds to the free form of PSP94 only (1A6), as described herein, and the second antibody may also be an antibody which binds to the free form of PSP94 (only). The first and second antibody may bind to different epitopes of PSP94.

The second antibody may carry an enzyme, i.e. horseradish peroxidase which, when the enzyme's substrate is added, produces a colorimetric reaction. In some cases, it may be useful to use a third antibody as a detection reagent instead of conjugating one of the specific antibodies (a first or a second antibody). In cases where a third antibody is used as detection reagent, this third antibody may carry itself a reporter molecule (or else). This third antibody may be able to recognize the second antibody (it may recognize the isotype and species of the second antibody).

In an additional aspect, the present invention provides an improved method for measuring the amount of free (unbound PSP94) PSP94 (and/or PSP94 fragments and analogues thereof) in a sample, the method comprising, contacting a sample free of the PSP94/PSP94-binding protein complex with an antibody able to recognize PSP94, PSP94 fragments and analogues thereof. For example, the improved method may for measuring the amount of free PSP94 in a sample may comprise;
   a) removing a complex formed by PSP94 and any one of the polypeptide selected from the group consisting of SEQ ID NO.: 2, SEQ ID NO.:3, SEQ ID NO.:7 SEQ ID NO.:8, SEQ ID NO.:9 and combination thereof, generating a complex-free sample, and;
   b) contacting the complex-free sample with an antibody able to recognize PSP94.

The improved method for measuring the amount of free (unbound PSP94) PSP94 in a sample contemplated herein may also comprise, for example, the following steps;
   a) removing a complex formed by PSP94 and any one of the polypeptide selected from the group consisting of SEQ ID NO.: 2, SEQ ID NO.:3, SEQ ID NO.:7, SEQ ID NO.:8, SEQ ID NO.:9 variants, fragments analogues and combination thereof, generating a complex-free sample (e.g., using methods described herein)
   b) immobilizing (coating, adsorbing) a PSP94-antibody to a suitable substrate (ELISA plate, matrix, SDS-PAGE, Western blot membranes),
   c) adding the complex-free sample comprising free (unbound) PSP94,
   d) adding a (PSP94) detection reagent comprising a label or marker, and;
   e) detecting a signal resulting from a label or marker.

Examples of suitable detection reagents that may be used in the present invention are reagents selected from the group consisting of an antibody, a polypeptide or other molecule having an affinity for PSP94. The detection reagent may have a different binding site than the PSP94-antibody, and the detection reagent may either be directly coupled to a label (or marker) or able to be recognized by a second molecule carrying (conjugated with) the label or marker.

An example of a PSP94-antibody used in step b) is the monoclonal antibody (2D3) produced by the hybridoma cell line deposited to the ATCC under Patent Deposit no.: PTA-4240. In that case, the monoclonal antibody (P1E8) (e.g., conjugated) produced by the hybridoma cell line deposited to the ATCC under Patent Deposit no.: PTA-4241 may be used as a detection reagent (directly or indirectly as described herein).

Another example of a PSP94-antibody that may be used in step b) is the monoclonal antibody (P1E8) produced by the hybridoma cell line deposited to the ATCC under Patent Deposit no.: PTA-4241. In that case the monoclonal antibody (2D3) (e.g., conjugated) produced by the hybridoma cell line deposited to the ATCC under Patent Deposit no.: PTA-4240 may be used as a detection reagent (directly or indirectly as described herein).

In a further aspect, the present invention relates to a method for measuring the amount of total PSP94 (bound and unbound (free)) in a sample, the method may comprise using a first and a second antibody able to bind to PSP94 even when PSP94 is bound to another polypeptide (e.g., SEQ ID NO.:2, SEQ ID NO.:3, SEQ ID NO.:7, SEQ ID NO.:8, SEQ ID NO.:9). It may be preferable that the first and second antibodies bind to a different PSP94 epitope.

In yet a further aspect, the present invention relates also to a method for measuring total PSP94 in a sample, the method comprising using a first and a second antibody, wherein the first antibody is able to bind to PSP94 even when PSP94 is bound to a polypeptide and wherein the second antibody is able to bind to PSP94 and to displace any one of the polypeptide selected from the group consisting of SEQ ID NO.:2, SEQ ID NO.:3, SEQ ID NO.:7, SEQ ID NO.:8, SEQ ID NO.:9 from a complex formed by PSP94 and the polypeptide.

In an embodiment of the present invention, the first antibody may be, for example, the monoclonal antibody produced by the hybridoma cell line deposited to the ATCC under Patent Deposit No.: PTA-4241, or any other suitable antibody. The second antibody may be, for example, the monoclonal antibody produced by the hybridoma cell line deposited to the ATCC under Patent Deposit No.: PTA-4240.

In an additional aspect the present invention provides a method for measuring the level (amount, concentration) of PSP94 in a sample the method comprising contacting the sample with an antibody that is able to recognize PSP94 in its free and bound forms (e.g., bound to SEQ ID NO.:2, SEQ ID NO.:3, SEQ ID NO.:7, SEQ ID NO.:8, SEQ ID NO.:9 etc.) forms.

In an embodiment of the present invention, the monoclonal antibody produced by the hybridoma cell line deposited to the ATCC under Patent Deposit NO.: PTA-4241 may be used.

When methods (e.g., measuring total PSP94, free PSP94, free or total PSP94-binding protein and calculating ratios) described herein are applied to clinical samples (serum, blood, plasma, etc.), they may be useful for screening subjects for a condition linked to abnormal or elevated levels of PSP94 (e.g., prostate cancer (e.g., prediction of relapse free interval in post-radiotherapy prostate cancer)) and for assessing, for example, prognosis in a subject diagnosed with prostate cancer. For example, it may be found that the higher the level of total PSP94 (or ratio of free PSP94/total PSP94, or total PSP94-binding protein) in individual with prostate cancer, relative to control subjects, the poorer the prognosis or higher the chance of having (developed recurrent) prostate cancer. In addition, when a raised level of total PSP94 (or other parameter described herein) is observed in a subject, it may be predictive (or suggestive) of prostate cancer in that subject. Thus, diagnostic and prognostic methods for screening subject for prostate cancer (or any other condition linked with an abnormal or elevated level of PSP94 or of PSP94-binding protein) are also encompassed by the present invention.

If desired or necessary, methods of the present invention may also include a step of collecting a sample; for example, a blood sample from an individual with a condition linked with elevated levels of PSP94 or other condition and performing the above-mentioned methods and assays.

Methods of the present invention may further comprise detecting a signal from a label that is provided (carried) by the molecule (antibody, polypeptide; e.g., from the label attached to the molecule) or by a second molecule (antibody or binding/ligand system) carrying the label.

Methods of the present invention may also include comparing (detecting) the signal (results) obtained for the sample with signal (results) obtained for a control sample containing a known amount of the polypeptide of interest.

In a further aspect, the present invention relates to the use of a PSP94 antibody for the treatment of a condition associated with elevated levels of PSP94. It is to be understood that a method of treating a patient with such condition, comprising administering a PSP94 antibody is also encompassed herein.

In yet a further aspect, the present invention relates to the use of a PSP94 antibody in the manufacture of a medicament for the treatment of a condition associated with elevated levels of PSP94.

The PSP94 antibodies may be for example, a monoclonal antibody produced by the hybridoma cell line deposited to the ATCC under Patent Deposit No.: PTA-4240 or a monoclonal antibody produced by the hybridoma cell line deposited to the ATCC under Patent Deposit No.: PTA-4241.

A sample, is to be understood herein as an aliquot of blood, serum, plasma, biological fluid, or it may be, for example, proteins (containing other constituents or not) bound to the well of an ELISA plate, a membrane, a gel, a matrix, etc.

In yet a further aspect, the present invention relates to the use of a molecule selected from the group consisting of the polypeptide as set forth in SEQ ID NO.:2, SEQ ID NO.:3, SEQ ID NO.: 7, SEQ ID NO.:8, SEQ ID NO.:9, a monoclonal antibody (2D3) produced by the hybridoma cell line deposited to the ATCC under Patent Deposit No.: PTA-4240, a monoclonal antibody (P1E8) produced by the hybridoma cell line deposited to the ATCC under Patent Deposit No.: PTA-4241, a monoclonal antibody (3F4) produced by the hybridoma cell line deposited to the ATCC under Patent Deposit No.: PTA-4242 and a monoclonal antibody (17G9) produced by the hybridoma cell line deposited to the ATCC under Patent Deposit No.: PTA-4243, for evaluating the amount of PSP94 (free and/or bound and/or total), PSP94 variants and analogues thereof in a sample.

According to the present invention, conditions that are contemplated for methods and uses described herein may comprise, for example, prostate cancer, stomach cancer, breast cancer, endometrial cancer, ovarian cancer, other cancers of epithelial secretory cells and benign prostate hyperplasia (BPH).

It is to be understood herein that other antibody may be used (are suitable) in the methods described herein. For example, PSP94-binding protein specific antibodies listed in table 10 are interchangeable and are encompassed by the present invention (including their hydridoma cell lines). For example the monoclonal antibody (3F4) produced by the hybridoma cell line deposited to the ATCC under Patent Deposit NO.: PTA-4242 may be interchanged with the monoclonal antibodies 2B10, 9B6, 1B11, etc. and the monoclonal antibody (17G9) produced by the hybridoma cell line deposited to the ATCC under Patent Deposit NO.: PTA-4243 may be interchanged with the monoclonal antibody P8C2, 1B11, 26B10, 9B6, etc. A variety of other conditions are possible. However, when two antibodies are needed to perform the present methods it is preferable to choose antibodies that bind to different epitopes.

It is also to be understood herein that antibody fragments, such as an antigen-binding fragment (e.g., antigen binding site) of any of the (monoclonal) antibodies disclosed herein are encompassed by the present invention.

General Molecular Biology and Definitions

Unless otherwise indicated, the recombinant DNA techniques utilized in the present invention are standard procedures, known to those skilled in the art. Solutions, reagents and buffer described herein may be prepared using reagents and methods known in the art. Example of techniques, solutions and reagents are explained in the literature in sources such as J. Perbal, A Practical Guide to Molecular Cloning, John Wiley and Sons (1984), J. Sambrook et al., Molecular Cloning: A Laboratory Manual, Cold Spring Harbor Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present) and are incorporated herein by reference.

"Polynucleotide" generally refers to any polyribonucleotide or polydeoxyribonucleotide, which may be unmodified RNA or DNA, or modified RNA or DNA. "Polynucleotides" include, without limitation single- and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus "polynucleotide" embraces chemically, enzymatically or metabolically modified forms of polynucleotides as typically found in nature, as well as the chemical forms of DNA and RNA characteristic of viruses and cells. "Polynucleotide" includes but is not limited to linear and end-closed molecules. "Polynucleotide" also embraces relatively short polynucleotides, often referred to as oligonucleotides.

Therefore, in accordance with the present invention, the polynucleotide may be, for example, a polyribonucleotide, a polydeoxyribonucleotide, a modified polyribonucleotide, a modified polydeoxyribonucleotide, a complementary polynucleotide (e.g., antisense) or a combination thereof.

"Polypeptide" refers to any peptide or protein comprising two or more amino acids joined to each other by peptide bonds or modified peptide bonds (i.e., peptide isosteres). "Polypeptide" refers to both short chains, commonly referred as peptides, oligopeptides or oligomers, and to longer chains generally referred to as proteins. As described above, polypeptides may contain amino acids other than the 20 gene-encoded amino acids.

"Variant" as the term used herein, is a polynucleotide or polypeptide that differs from reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusion and truncations in the polypeptide encoded by the reference sequence, as discussed herein. A typical variant of a polypeptide differs in amino acid sequence from another, reference polypeptide. Generally, differences are limited so that the sequence of the reference polypeptide and the variant are closely similar overall and, in many regions, identical. A variant and reference polypeptide may differ in amino acid by one or more substitutions, additions, deletions, or any combination therefore. A substituted or inserted amino acid residue may or may not be one encoded by the genetic code. A variant polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis. "Variants" as used herein encompass (active) mutants, analogues, homologues, chimeras, fragments and portions thereof. However, "variants" as used herein may retain parts of the biological activity of the original polypeptide.

As used herein, "pharmaceutical composition" means therapeutically effective amounts of the agent together with suitable diluents, preservatives, solubilizers, emulsifiers, adjuvant and/or carriers. A "therapeutically effective amount" as used herein refers to that amount which provides a therapeutic effect for a given condition and administration regimen. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts) solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils). Also comprehended by the invention are particulate compositions coated with polymers (e.g., poloxamers or poloxamines). Other embodiments of the compositions of the invention incorporate particulate forms protective coatings, protease inhibitors or permeation enhancers for various routes of administration, including parenteral, pulmonary, nasal and oral routes. In one embodiment the pharmaceutical composition is administered parenterally, paracancerally, transmucosally, transdermally, intramuscularly, intravenously, intradermally, subcutaneously, intraperitonealy, intraventricularly, intracranially and intratumorally.

An "immunizing composition" or "immunogenic composition" as used herein refers to a composition able to promote an immune response in the host receiving such composition. An "immunizing composition" includes a compound, such as for example, a polypeptide (or a DNA or RNA able to encode a polypeptide) for which an antibody is sought. The polypeptide is usually diluted in a buffer, diluent or a pharmaceutically acceptable carrier. An "immunizing composition" may comprise an adjuvant such as or example complete Freund's adjuvant, incomplete Freund's adjuvant and aluminum hydroxide.

Further, as used herein "pharmaceutically acceptable carrier" or "pharmaceutical carrier" are known in the art and include, but are not limited to, 0.01-0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's orfixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

As used herein, "PSP94-binding protein" relates to a protein (such as SEQ ID NO.:2, SEQ ID No.:3, SEQ ID NO.:7, SEQ ID NO.:8, SEQ ID NO.:9) that is able to bind (i.e., associate) to PSP94, usually in a reversible fashion.

As used herein, the term "free PSP94" relates to a PSP94 protein that is not associated with another polypeptide (e.g., with a PSP94-binding protein). The term "free PSP94" means that PSP94 is in an unbound form (state).

As used herein, the term "antibody" refers to either monoclonal antibody, polyclonal antibody, humanized antibody, single-chain antibody, antibody fragments including Fc, F(ab)2, F(ab)2' and Fab and the like. It is to be understood that a "polyclonal antibody" is a term used to refer to antibodies generated by immunizing an animal against an antigen and which are often directed to multiple epitopes of the antigen.

As used herein, the term "antigen binding fragment" relates to an antibody fragment (antigen binding domain) able to recognize (bind) the antigen of interest. An "antigen binding fragment", may be isolated from the gene(s) (e.g., gene encoding a variable region) encoding the antibody using molecular biology methods. The isolated gene(s) may engineered to create, for example, a single chain antibody. The "antigen binding fragment" of an antibody is known to be responsible for the specific binding of the antibody to the antigen.

As used herein "PSP94" or "PSP" relates to the native and recombinant PSP94.

Gene (cDNA) Cloning and Protein Expression

The identified and isolated gene (i.e., polynucleotide) may be inserted into an appropriate cloning or expression vector (i.e., expression system). A large number of vector-host systems known in the art may be used. Possible vectors include, but are not limited to, plasmids or modified viruses (e.g., bacteriophages, adenoviruses, adeno-associated viruses, retroviruses), but the vector system must be compatible with the host cell used. Examples of cloning vectors include, but are not limited to, *Escherichia coli* (*E. coli*), bacteriophages such as lambda derivatives, or plasmids such as pBR322 derivatives or pUC plasmid derivatives (e.g., pGEX vectors, pmal-c, pFLAG, etc). Examples of expression vectors are discussed bellow. The insertion into a cloning or expression vector can, for example, be accomplished by ligating the DNA fragment into a cloning vector, which has complementary cohesive termini. However, if the complementary restriction sites used to fragment the DNA are not present in the cloning vector, the ends of the DNA molecules may be enzymatically modified.

Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, lipofection, infection, electroporation, etc. The cloned gene may be contained on a shuttle vector plasmid, which provides for expansion in a cloning cell, e.g., *E. coli*, and facilitate purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences from the yeast 2.mu. plasmid.

It is to be understood herein that when the polynucleotide (e.g., gene, cDNA, RNA) of the present invention is inserted into the appropriate vector, it may be used, for example, as a way to express the protein in a foreign host cell for its isolation (such as bacteria, yeast, insect, animal or plant cells) or in a (isolated) cell from an individual for purpose of gene therapy treatment or cell-mediated vaccination (using, for example, dendritic cells). For example, cells may be isolated from a mammal and treated (e.g., exposed, transfected, lipofected, infected, bombarded (using high velocity microprojectiles)) ex-vivo with the polynucleotide (cDNA, gene, RNA, antisense) of the present invention before being re-infused in the same individual or in a compatible individual. In vivo delivery of a polynucleotide may be performed by other methods than the one described above. For example, liposomal formulations when injected, may also be suitable for mediating in vivo delivery of a polynucleotide.

Any of a wide variety of expression systems may be used to provide a recombinant polypeptide (protein). The precise host cell used is not critical to the invention. Polypeptides of the present invention may be produced in a prokaryotic host (e.g., *E. coli* or *Bacillus subtilis* (*B. subtilis*)) or in a eukaryotic host (yeast e.g., *Saccharomyces* or *Pichia Pastoris*; mammalian cells, e.g., monkey COS cells, mouse 3T3 cells (Todaro G J and Green H., J. Cell Biol. 17: 299-313, 1963), Chinese Hamster Ovary cells (CHO) (e.g., Puck T T et al., J. Exp. Med. 108: 945-956, 1958), BHK, human kidney 293 cells (e.g., ATCC: CRL-1573), or human Heal cells (e.g., ATCC: CCL-2); or insect cells).

In a yeast cell expression system such as *Pichia Pastors* (*P. Pastoris*), DNA sequence encoding polypeptides of the present invention may be cloned into a suitable expression vector such as the pPIC9 vector (Invitrogen). Upon introduction of a vector containing the DNA sequence encoding all or part of the polypeptides of the present invention into the *P. Pastors* host cells, recombination event may occur for example in the AOX1 locus. Such recombination event may place the DNA sequence of polypeptides of the present invention under the dependency of the AOX1 gene promoter. Successful insertion of a gene (i.e. DNA sequence) encoding polypeptides of the present invention may result in an expression of such polypeptides that is regulated and/or induced by methanol added in the growth media of the host cell (for reference see Buckholz, R. G. and Gleeson, M. A. G., Biotechnology, 9:1067-1072, 1991; Cregg, J. M., et al., Biotechnology, 11:905-910, 1993; Sreekrishna, K., et al., J. Basic Microbiol., 28:265-278, 1988; Wegner, G. H., FEMS Microbiology Reviews, 87:279-284, 1990).

In mammalian host cells, a number of viral-based expression systems may be utilized. For example, in the event where an adenovirus is used as an expression vector for the polypeptides of the present invention, nucleic acid sequence may be ligated to an adenovirus transcription/translation control complex (e.g., the late promoter and tripartite leader sequence). This chimeric gene may be inserted into the adenovirus genome, for example, by in vitro or in vivo recombination. Insertion into a non-essential region of the viral genome (e.g., region E1 or E3) may result in a recombinant virus that is viable and capable of expressing polypeptides of the present invention in infected hosts.

Proteins and polypeptides of the present invention may also be produced by plant cells. Expression vectors such as cauliflower mosaic virus and tobacco mosaic virus and plasmid expression vectors (e.g., Ti plasmid) may be used for the expression of polypeptides in plant cells. Such cells are available from a wide range of sources (e.g., the American Type Culture Collection, Rockland, Md.). The methods of transformation or transfection and the choice of expression vehicle are of course to be chosen accordingly to the host cell selected.

In an insect cell expression system such as *Autographa californica* nuclear polyhedrosis virus (AcNPV), which grows in *Spodoptera frugiperda* cells, AcNPV may be used as a vector to express foreign genes. For example, DNA sequence coding for polypeptides of the present invention may be cloned into non-essential regions of the virus (for example the polyhedrin gene) and placed under control of an AcNPV promoter, (e.g., the polyhedrin promoter). Successful insertion of a gene (i.e., DNA sequence) encoding polypeptides of the present invention may result in inactivation of the polyhedrin gene and production of non-occluded recombinant virus (i.e., virus lacking the proteinaceous coat encoded by the polyhedrin gene). These recombinant viruses may be used to infect *spodoptera frugiperda* cells in which the inserted gene is expressed.

In addition, a host cell may be chosen for its ability to modulate the expression of the inserted sequences, or to modify or process the gene product in a specific, desired fashion. Such modifications (e.g., glycosylation) and processing (e.g., cleavage) of protein products may be important for the function of the protein. Different host cells have characteristics and specific mechanisms for posttranslational processing and modification of proteins and gene products. Of course, cell lines or host systems may be chosen to ensure desired modification and processing of the foreign protein expressed. To this end, eukaryotic host cells that possess the cellular machinery for proper processing of the primary transcript, glycosylation, and phosphorylation of the gene product may be used. Such mammalian host cells comprise for example, but are not limited to, CHO, VERO, BHK, Heal, COS, MDCK, 293, and 3T3.

Alternatively, polypeptides of the present invention may be produced by a stably-transfected mammalian cell line. A number of vectors suitable for stable transfection of mammalian cells are available to the public; methods for constructing such cell lines are also publicly available. In one example, cDNA encoding the rHuPSP94 protein may be cloned into an expression vector that includes the dihydrofolate reductase (DHFR) gene. Integration of the plasmid and, therefore, DNA sequence of polypeptides of the present invention, into the host cell chromosome may be selected for by including methotrexate in the cell culture media. This selection may be accomplished in most cell types.

Specific initiation signals may also be required for the efficient translation of DNA sequences inserted in a suitable expression vehicle as described above. These signals may include the ATG initiation codon and adjacent sequences. For example, in the event where gene or cDNA encoding polypeptides of the present invention, would not have their own initiation codon and adjacent sequences, additional translational control signals may be needed. For example, exogenous translational control signals, including, perhaps, the ATG initiation codon, may be needed. It is known in the art that the initiation codon must be in phase with the reading frame of the polypeptide sequence to ensure proper translation of the desired polypeptide. Exogenous translational control signals and initiation codons may be of a variety of origins, including both natural and synthetic. The efficiency of expression may be enhanced by the inclusion of appropriate transcription enhancer elements, transcription terminators. The transcription, translation signals may be specifically engineered to provide a desired expression pattern and level (e.g., signals that may require a specific inducer, signals that will allow expression in a defined cell type or in a specific time frame).

However, these signals may be provided by the expression vector, which often contains a promoter enabling the expression of the polypeptide in a desired host cell.

Polypeptide Modifications (Mutants, Variants, Analogues, Homologues Chimeras and Portions/Fragments).

As may be appreciated, a number of modifications may be made to the polypeptides and fragments of the present invention without deleteriously affecting the biological activity of the polypeptides or fragments. Polypeptides of the present invention comprises for example, those containing amino acid sequences modified either by natural processes, such as posttranslational processing, or by chemical modification techniques which are known in the art. Modifications may occur anywhere in a polypeptide including the polypeptide backbone, the amino acid side-chains and the amino or carboxy-termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslational natural processes or may be made by synthetic methods. Modifications comprise for example, without limitation, acetylation, acylation, addition of acetomidomethyl (Acm) group, ADP-ribosylation, amidation, covalent attachment to fiavin, covalent attachment to a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation and ubiquitination (for reference see, Protein-structure and molecular properties, 2$^{nd}$ Ed., T. E. Creighton, W. H. Freeman and Company, New-York, 1993).

Other type of polypeptide modification may comprises for example, amino acid insertion (i.e., addition), deletion and substitution (i.e., replacement), either conservative or non-conservative (e.g., D-amino acids, desamino acids) in the polypeptide sequence where such changes do not substantially alter the overall biological activity of the polypeptide. Polypeptides of the present invention comprise for example, biologically active mutants, variants, fragments, chimeras, and analogs; fragments encompass amino acid sequences having truncations of one or more amino acids, wherein the truncation may originate from the amino terminus (N-terminus), carboxy terminus (C-terminus), or from the interior of the protein. Polypeptide analogs of the invention involve an insertion or a substitution of one or more amino acids. Variants, mutants, fragments, chimeras and analogs may have the biological property of polypeptides of the present invention.

It should be further noted that if the polypeptides are made synthetically, substitutions by amino acids, which are not naturally encoded by DNA may also be made. For example, alternative residues include the omega amino acids of the formula NH2(CH2)nCOOH wherein n is 2-6. These are neutral nonpolar amino acids, as are sarcosine, t-butyl alanine, t-butyl glycine, N-methyl isoleucine, and norleucine. Phenylglycine may substitute for Trp, Tyr or Phe; citrulline and methionine sulfoxide are neutral nonpolar, cysteic acid is acidic, and ornithine is basic. Proline may be substituted with hydroxyproline and retain the conformation conferring properties.

It is known in the art that mutants or variants may be generated by substitutional mutagenesis and retain the biological activity of the polypeptides of the present invention. These variants have at least one amino acid residue in the protein molecule removed and a different residue inserted in its place. For example, one site of interest for substitutional mutagenesis may include but are not restricted to sites identified as the active site(s), or immunological site(s). Other sites of interest may be those, for example, in which particular residues obtained from various species are identical. These positions may be important for biological activity. Examples of substitutions identified as "conservative substitutions" are shown in table 1. If such substitutions result in a change not desired, then other type of substitutions, denominated "exemplary substitutions" in table 1, or as further described herein in reference to amino acid classes, are introduced and the products screened.

Example of substitutions may be those, which are conservative (i.e., wherein a residue is replaced by another of the same general type). As is understood, naturally-occurring amino acids may be sub-classified as acidic, basic, neutral and polar, or neutral and non-polar. Furthermore, three of the encoded amino acids are aromatic. It may be of use that encoded polypeptides differing from the determined polypeptide of the present invention contain substituted codons for amino acids, which are from the same group as that of the amino acid be replaced. Thus, in some cases, the basic amino acids Lysine (Lys), Arginine (Arg) and Histidine (His) may be interchangeable; the acidic amino acids Aspartic acid (Asp) and Glutamic acid (Glu) may be interchangeable; the neutral polar amino acids Serine (Ser), Threonine (Thr), Cysteine (Cys), Glutamine (Gln), and Asparagine (Asn) may be interchangeable; the non-polar aliphatic amino acids Glycine (Gly), Alanine (Ala), Valine (Val), Isoleucine (Ile), and Leucine (Leu) are interchangeable but because of size Gly and Ala are more closely related and Val, Ile and Leu are more closely related to each other, and the aromatic amino acids Phenylalanine (Phe), Tryptophan (Trp) and Tyrosine (Tyr) may be interchangeable.

TABLE 1

Exemplary amino acid substitution

| Original residue | Exemplary substitution | Conservative substitution |
|---|---|---|
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Asn, Gln, Lys, Arg | Arg |
| Ile (I) | Leu, Val, Met, Ala, Phe, norleucine | Leu |

TABLE 1-continued

Exemplary amino acid substitution

| Original residue | Exemplary substitution | Conservative substitution |
|---|---|---|
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala | Leu |
| Pro (P) | Gly | Gly |
| Ser (S) | Thr | Thr |
| Thr (T) | Ser | Ser |
| Trp (W) | Tyr | Tyr |
| Tyr (Y) | Trp, Phe, Thr, Ser | Phe |
| Val (V) | Ile, Leu, Met, Phe, Ala, norleucine | Leu |

In some cases it may be of interest to modify the biological activity of a polypeptide by amino acid substitution, insertion, or deletion. For example, modification of a polypeptide may result in an increase in the polypeptide's biological activity, may modulate its toxicity, may result in changes in bioavailability or in stability, or may modulate its immunological activity or immunological identity. Substantial modifications in function or immunological identity are accomplished by selecting substitutions that differ significantly in their effect on maintaining (a) the structure of the polypeptide backbone in the area of the substitution, for example, as a sheet or helical conformation. (b) the charge or hydrophobicity of the molecule at the target site, or (c) the bulk of the side chain. Naturally occurring residues are divided into groups based on common side chain properties:

(1) hydrophobic: norleucine, methionine (Met), Alanine (Ala), Valine (Val), Leucine (Leu), Isoleucine (Ile)
(2) neutral hydrophilic: Cysteine (Cys), Serine (Ser), Threonine (Thr)
(3) acidic: Aspartic acid (Asp), Glutamic acid (Glu)
(4) basic: Asparagine (Asn), Glutamine (Gln), Histidine (His), Lysine (Lys), Arginine (Arg)
(5) residues that influence chain orientation: Glycine (Gly), Proline (Pro); and
(6) aromatic: Tryptophan (Trp), Tyrosine (Tyr), Phenylalanine (Phe)

Non-conservative substitutions will entail exchanging a member of one of these classes for another.

Mutant polypeptides will possess one or more mutations, which are deletions (e.g., truncations), insertions (e.g., additions), or substitutions of amino acid residues. Mutants can be either naturally occurring (that is to say, purified or isolated from a natural source) or synthetic (for example, by performing site-directed mutagenesis on the encoding DNA or made by other synthetic methods such as chemical synthesis). It is thus apparent that the polypeptides of the invention can be either naturally occurring or recombinant (that is to say prepared from the recombinant DNA techniques).

A protein at least 50% identical to those polypeptides of the present invention, as determined by methods known to those skilled in the art (for example, the methods described by Smith, T. F. and Waterman M. S. (1981) Ad. Appl. Math., 2:482-489, or Needleman, S. B. and Wunsch, C. D. (1970) J. Mol. Biol., 48: 443-453) is included in the invention, as are proteins at least 70% or 80% and more preferably at least 90% identical to the protein of the present invention. This will generally be over a region of at least 5, preferably at least 20, contiguous amino acids.

Amino acid sequence variants may be prepared by introducing appropriate nucleotide changes into DNA, or by in vitro synthesis of the desired polypeptide. Such variant include, for example, deletions, insertions, or substitutions of residues within the amino acid sequence. A combination of deletion, insertion and substitution can be made to arrive at the final construct, provided that the final protein product possesses the desired characteristics. The amino acid changes also may alter posttranslational processes such as changing the number or position of the glycosylation sites, altering the membrane anchoring characteristics, altering the intra-cellular location by inserting, deleting or otherwise affecting the transmembrane sequence of the native protein, or modifying its susceptibility to proteolytic cleavage.

Protein Purification

Some aspects of the present invention concern the purification, and in particular embodiments, the substantial purification, of a polypeptide. The term "purified polypeptide" as used herein, is intended to refer to a composition, isolatable from other components, wherein the polypeptide is purified to any degree relative to its naturally-obtainable state, (i.e., in this case, relative to its purity within a prostate, cell extract). A purified polypeptide therefore also refers to a polypeptide, free from the environment in which it may naturally occur.

Generally, "purified" will refer to a polypeptide composition, which has been subjected to fractionation to remove various other components, and which composition substantially retains its expressed biological activity. Where the term "substantially purified" is used, this will refer to a composition in which the polypeptide forms the major component or portion of the composition, such as constituting about 50% or more of the polypeptides in the composition.

Various techniques suitable for use in polypeptide purification will be well known to those of skill in the art. These include, for example, precipitation with ammonium sulfate, PEG, antibodies and the like or by heat denaturation, followed by centrifugation; chromatography steps such as ion exchange, gel filtration (i.e., size exclusion chromatography), reverse phase, hydroxylapatite and affinity chromatography; isoelectric focusing; gel electrophoresis; and combinations of such and other techniques. These techniques may be used either alone or in combination. As is generally known in the art, it is believed that the order of conducting the various purification steps may be changed, or that certain steps may be omitted, and still result in a suitable method for the preparation of a substantially purified polypeptide.

The ability of purifying a protein by ammonium sulfate precipitation is based on the fact that a protein's solubility is lowered at high salt concentration. However, the solubility of proteins is affected in a different manner depending on their properties.

Size exclusion chromatography or gel filtration separates molecules based on their size. The gel (i.e., matrix, resin) media may consist of beads containing pores of a specific distribution. Separation may occur when molecules of different size are included or excluded from the pores within the matrix. Small molecules may diffuse into the pores and their flow through the column is retarded, while large molecules do not enter the pores and are eluted in the column's void volume. Consequently, molecules separate based on their size as they pass through the column and are eluted in order of decreasing molecular weight.

Proteins can be separated on the basis of their net charge by ion-exchange chromatography. For example, if a protein has a net positive charge at pH 7, it will usually bind (adsorb) to beads (i.e., matrix) containing a negatively charged group.

For example, a positively charged protein can be separated on a negatively charged carboxymethyl-cellulose or carboxymethyl-agarose matrix. Following elution, proteins that have a low density of net positive charge will tend to emerge first from the column followed by those having a higher charge density. Negatively charged proteins can be separated by chromatography on positively charged diethylaminoethyl-cellulose (DEAE-cellulose) or DEAE-agarose matrix. A charged protein bound to an ion-exchange matrix may be eluted (released, detached) by increasing the concentration of sodium chloride or another salt solution as an eluting buffer. Ions will compete with the charged groups on the protein for binding to the matrix.

Salt solutions may be added to the matrix in a sequential manner (i.e., by adding a solution of a specific molarity (e.g., 100 mM sodium chloride) followed by the addition of one or more solutions of different molarity (e.g., 200 mM, followed by a solution of 300 mM, followed by a solution of 400 mM, followed by a solution of 500 mM, followed by a solution of 1000 mM)) until the specific polypeptide of the invention (i.e., PSP94-binding protein (SEQ ID NO.:2, SEQ ID NO.:3, SEQ ID NO.:7, SEQ ID NO.:8, SEQ ID NO.:9) is eluted. In addition, salts solution may be added as a continuous gradient. For example, a salt solution of high molarity (e.g., 1000 mM) may be gradually added to a second solution of lower molarity (e.g., 100 mM) before entering the ion-exchange chromatography column. The salt solution entering the column will have a molarity slowly increasing from 100 mM to up to 1000 mM.

Affinity chromatography may be used when the specificity (affinity) of a polypeptide for a compound is known or suspected. For example, as a first step such compound (e.g., PSP94) is covalently attached to a column (e.g., a cyanogen bromide activated sepharose matrix) and a mixture (solution) containing a desired polypeptide (e.g., a PSP94-binding protein) may be added to the matrix. After washing the matrix, to remove unbound proteins, the desired polypeptide may be eluted from the matrix by adding a high concentration of the compound (e.g., PSP94) in a soluble form. Antibodies are an example of a compound, which is often used to purify proteins to which it binds.

It is known in the art, that equilibration and substantial washing of chromatography matrix (i.e., resin) (e.g., ion-exchange matrix, size-exclusion matrix, affinity matrix) is preferred in order to minimize binding of unwanted (i.e., unspecific) proteins (non-specific binding).

Antibodies and Hybridoma

Other aspects of the present invention relates to antibodies and hybridoma cell lines. The preparation and characterization of antibodies are well known in the art (See, e.g., Antibodies: A Laboratory Manual., Cold Spring Harbor Laboratory, 1988; incorporated herein by reference) and has been discussed in U.S. Pat. No. 6,156,515, the entire content of which is incorporated herein by reference.

For example, a polyclonal antibody preparation may be obtained by immunizing an animal with an immunogenic (immunizing) composition and collecting antisera from that immunized animal. A wide range of animal species may be used for the production of antisera. Typically the animal used for production of anti-antisera is a rabbit, a mouse, a rat, a hamster, a guinea pig or a goat.

It is often necessary to boost the host immune system by coupling, for example, an immunogen to a carrier (e.g., keyhole limpet hemocyanin (KLH) and bovine serum albumin (BSA)) or by incorporating an adjuvant to the immunizing composition, as described herein.

The production of antibodies may be monitored by sampling blood of the immunized animal at various time points following immunization. Sometimes, additional boosts may be required to provide a sufficient titer of the antibody(ies).

The desired antibody may be purified by known methods, such as affinity chromatography using, for example, another antibody or a peptide bound to a solid matrix.

Monoclonal antibodies (mAbs) may be readily prepared through use of known techniques, such as those exemplified in U.S. Pat. No. 4,196,265, the entire content of which is incorporated herein by reference. Mice (e.g., BALB/c mouse) and rats are the animals that are usually used for the immunization. Following immunization, B lymphocytes (B cells), are selected for use in the mAb generating protocol. Often, a panel of animals will have to be immunized and the animal having the highest antibody titer will be chosen. The antibody-producing B lymphocytes from the immunized animal are then fused (e.g., using polyethylene glycol) with cells of an immortal myeloma cell. Any one of a number of myeloma cells may be used, as are known to those of skill in the art (Goding, pp. 65-66, 1986; Campbell, pp. 75-83, 1984). For example, where the immunized animal is a mouse, one may use P3-X63/Ag8, X63-Ag8.653, NS1/1.Ag 4 1, Sp210-Ag14, FO, NSO/JU, MPC-11, MPC11-X45-GTG 1.7 and S194/5XXO Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

Fused hybrids are grown in a selective medium that enables the differentiation between fused cells and the parental cells (i.e., myeloma and B cells). The selective medium usually contains an agent (e.g., aminopterin, methotrexate, azaserine) that blocks the de novo synthesis of nucleotides. When aminopterin or methotrexate is used, the media is supplemented with hypoxanthine and thymidine as a source of nucleotides (HAT medium). Where azaserine is used, the media is supplemented with hypoxanthine. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells may operate this pathway, but they have a limited life span in culture and generally die within about two weeks. Therefore, the only cells that can survive in the selective media are those hybrids formed from myeloma and B cells.

Selection of hybridomas is performed by culturing the cells by single-clone dilution in microtiter plates, followed by testing the individual clonal supernatants for the desired reactivity. The selected hybridomas may then be serially diluted and cloned into individual antibody-producing cell lines, which clones may then be propagated indefinitely to provide mAbs.

Fragments of monoclonal antibody(ies) are encompassed by the present invention. These may be obtained by methods, which include digestion with enzymes such as pepsin or papain and/or cleavage of disulfide bonds by chemical reduction. Alternatively, monoclonal antibody fragments encompassed by the present invention may be synthesized using an automated peptide synthesizer or may be produced from cloned gene segments engineered to produce such fragment (e.g., single-chain antibody) in a suitable cell (cell line).

Antibody conjugates are also encompassed by the present invention. These may be generated by coupling the antibody with a reporter molecule, a fluorophore, a chromophore or dye (e.g., rhodamine, fluoroscein, and green fluorescent protein) or any other agent or label that gives rise to a detectable signal, either by acting alone or following a biochemical reaction (e.g., enzymes such as horseradish peroxidase, alkaline phosphatase and beta-galactosidase). A molecule such as diethylenetriaminepentaacetic acid (DTPA) may also be linked to the antibody. DTPA may act as a chelating agent that is able to bind to heavy metal ions including radioisotopes (e.g. Isotope 111 of Indium ($^{111}$In)). These conjugates may be used as detection tools in immunoassays or in imaging. Alternatively, conjugates having a therapeutic agent such as a toxin may be prepared from the monoclonal antibodies of the present invention, these may be used to target cancer cells and to promote their destruction.

It will be appreciated by those of skill in the art that monoclonal or polyclonal antibodies specific for proteins that are linked to prostate cancer will have utilities in several types of applications. These may include the production of diagnostic kits for use in detecting, diagnosing or evaluating the prognosis of individual with prostate cancer.

Antigen Detection

In terms of antigen detection, the biological sample analyzed may be any sample that is suspected of containing an antigen of interest, either a tissue, cell lysate, urine, blood, serum, plasma, etc.

Contacting the biological sample with the antigen detection (detecting) reagent (protein, peptide or antibody) is generally a matter of simply adding the composition to the sample and incubating the mixture for a period of time long enough for the antibodies to form immune complexes with the antigen. Washing of the sample (i.e., tissue section, ELISA plate, dot blot or Western blot) is generally required to remove any non-specifically bound antibody species. The antigen-antibody complex (immunocomplex) is then detected using specific reagents.

When, for example, the antigen detecting reagent is an antibody (a specific antibody), this antibody may be (directly) labeled with a marker (fluorophore, chromophore, dye, enzyme, radioisotope, etc.) for enabling the detection of the complex. In other instances, it may be advantageous to use a secondary binding ligand such as a secondary antibody or a biotin/avidin (streptavidin) (binding/ligand complex) arrangement, as is known in the art. Again, secondary antibodies may be labeled with a marker as described above or with an arrangement of biotin/avidin (i.e. avidin peroxidase) or biotin/streptavidin (i.e. streptavidin coupled with a reporter molecule (e.g., peroxidase)), which allow the detection of the immunocomplex. United States patents concerning the use of such labels include U.S. Pat. Nos. 3,817,837; 3,850,752; 3,939,350; 3,996,345; 4,277,437; 4,275,149 and 4,366,241, each incorporated herein by reference. Usually, the secondary antibody will be an antibody directed to the specific antibody (primary antibody) of a defined isotype and species such as, for example, an anti-mouse IgG.

On the other hand, the antigen detecting reagent may also be a polypeptide having affinity for an antibody or another polypeptide, which forms a complex (i.e., polypeptide-polypeptide complex or antibody-polypeptide complex). In that case, the polypeptide itself may be labeled using the markers described above, allowing direct detection. Again, the complex may be detected indirectly by adding a secondary (labeled) antibody or polypeptide.

Immunodetection methods, such as enzyme-linked immunosorbent assays (ELISA), Western blots, etc. have utility in the diagnosis of conditions such as prostate cancer. However, these methods also have applications to non-clinical samples, such as in the titering of antigen or antibody samples, in the selection of hybridomas, and the like.

ELISA

The methods, assays, kits, antibodies and reagent described herein may find utility for example, in the diagnosis/prognosis of prostate cancer.

Immunoassays that may be performed using reagents of the present invention includes, for example, enzyme linked immunosorbent assays (ELISAs) and radioimmunoassays (RIA), which are known in the art. Immunohistochemical detection using tissue sections is also particularly useful. However, it will be readily appreciated that detection is not limited to such techniques, and Western blotting, dot blotting, FACS analyses, and the like also may be used.

Examples of ELISA assays include the following; antibodies binding to a polypeptide (e.g., antibodies to PSP94) are immobilized onto a selected surface (i.e., suitable substrate) exhibiting protein affinity, such as a well in a polystyrene microtiter plate (ELISA plate). Then, a sample suspected of containing the polypeptide is added to the wells of the plate. After binding and washing to remove non-specifically bound immunocomplexes, the bound antigen may be detected. Detection may be achieved by the addition of a second antibody specific for the target polypeptide, which is linked to a detectable label. This type of ELISA is a simple "sandwich ELISA." Detection also may be achieved by the addition of a second antibody, followed by the addition of a third antibody that has binding affinity for the second antibody, with the third antibody being linked to a detectable label (marker).

Another example of ELISA assay is the following; the samples suspected of containing the polypeptide of interest are immobilized onto the surface of a suitable substrate and then contacted with the antibodies of the invention. After binding and washing to remove non-specifically bound immunocomplexes, the bound antigen is detected. The immunocomplexes may be detected directly or indirectly as described herein.

An additional example of an ELISA assay is the following; again, polypeptides are immobilized to a substrate, however, in that case the assay involves a competition step. In this ELISA, a known amount of the polypeptide of interest is adsorbed to the plate. The amount of polypeptide in an unknown sample is then determined by mixing the sample with a specific antibody before or during incubation with wells containing the immobilized polypeptide. A detection reagent is added (e.g., antibody) to quantify the antibody that is able to bind to the immobilized polypeptide. The presence of the polypeptide in the sample acts to reduce the amount of antibody available for binding to the polypeptide contained in the well (immobilized polypeptide) and thus reduces the signal.

In order to get a correlation between the signal and the amount (concentration) of polypeptide in an unknown sample, a control sample may be included during the assay. For example, known (predetermined) quantities of a polypeptide (usually in a substantially pure form) may be measured (detected) at the same time as the unknown sample. The signal obtained for the unknown sample is then compared with the signal obtained for the control. The intensity (level) of the signal is usually proportional to the amount of polypeptide (antibody bound to the polypeptide) in a sample. However, the amount of control polypeptide and antibodies required to generate a quantitative assay needs to be evaluated first.

In coating a plate with either an antigen (polypeptide) or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

Conditions that may allow immunocomplex (antigen/antibody) formation include diluting the antigens and antibodies with solutions such as BSA, bovine gamma globulin (BGG) and phosphate buffered saline (PBS)/Tween. These added agents also tend to assist in the reduction of nonspecific background.

Suitable conditions involves that the incubation is at a temperature and for a period of time sufficient to allow effective binding. Incubation steps are typically from about 1 to 2 to 4 h, at temperatures preferably on the order of 20° C. to 27° C., or may be overnight at about 4° C. or so.

Often, the detection of the immunocomplex is performed with a reagent that is linked to an enzyme. Detection usually requires the addition of the enzyme's substrate. Enzymes such as, for example, a phosphatase (e.g., alkaline phosphatase), a peroxidase, etc. when given an appropriate substrate will generate a reaction that may be quantified by measuring the intensity (degree) of color (radioactivity, fluorescence, etc.) produced. The reaction is usually linear over a wide range of concentrations and may be quantified using a visible spectra spectrophotometer.

Kits

The present invention also relates to immunodetection kits and reagents for use with the immunodetection methods described above. As the polypeptide of the present invention may be employed to detect antibodies and the corresponding antibodies may be employed to detect the polypeptide, either or both of such components may be provided in the kit. The immunodetection kits may thus comprise, in suitable container means, a polypeptide (PSP94, or PSP94-binding protein), or a first antibody that binds to a polypeptide and/or an immunodetection reagent. The kit may comprise also a suitable matrix to which the antibody or polypeptide of choice may already be bound. Suitable matrix include an ELISA plate. The plate provided with the kit may already be coated with the antibody or polypeptide of choice. The coated ELISA plate may also have been blocked using reagents described herein to prevent unspecific binding. Detection reagents may also be provided and may include, for example, a secondary antibody or a ligand, which may carry the label or marker and/or an enzyme substrate. Kits may further comprise an antibody or polypeptide (usually of known titer or concentration) that may be used for control. Reagents may be provided, for example, lyophilized or in liquid form (of a defined concentration) and are provided in suitable containers (ensuring stability of reagents, safety etc.).

It is to be understood herein, that if a "range", "group of substances" or particular characteristic (e.g., temperature, concentration, time and the like) is mentioned, the present invention relates to and explicitly incorporates herein each and every specific member and combination of sub-ranges or sub-groups therein whatsoever. Thus, any specified range or group is to be understood as a shorthand way of referring to each and every member of a range or group individually as well as each and every possible sub-ranges or sub-groups encompassed therein; and similarly with respect to any sub-ranges or sub-groups therein. Thus, for example, with respect to reaction time, a time of 1 minute or more is to be understood as specifically incorporating herein each and every individual time, as well as sub-range, above 1 minute, such as for example 1 minute, 3 to 15 minutes, 1 minute to 20 hours, 1 to 3 hours, 16 hours, 3 hours to 20 hours etc.;

and similarly with respect to other parameters such as concentrations, temperature, etc. . . .

It is also to be understood herein that non-PSP94-binding protein (or DNA encoding such polypeptide) are excluded of the polypeptide or polynucleotide of the present invention.

TABLE 2

Table of abbreviation.

| Abbreviation | Signification |
| --- | --- |
| M | Molar |
| mM | milliMolar |
| g | gram |
| mg | milligram |
| μg or ug | microgram |
| ng | nanogram |
| ° C. or ° C. | Degree Celcius |
| % | percent |
| cm | centimeter |
| cpm (CPM) | Counts per minute |
| PBS | Phosphate buffered saline |
| NaCl | Sodium chloride |
| MES | 2-(N-Morpholino)ethanesulfonic acid |
| MOPS | 3-(N-Morpholino)propanesulfonic acid |
| UV | ultraviolet |
| Da | dalton |
| kDa | kilodalton |
| Kd | Dissociation constant |
| nm | nanometer |
| OD | Optical density |
| CAPS | 3-(Cyclohexylamino)-1-propanesulfonic acid |
| HMW | High molecular weight |
| DMSO | Dimethylsulfoxide |
| PVDF | Polyvinylidene difluoride |
| LMW | Low molecular weight |
| FSH | Follicle stimulating hormone |
| PSP94 or PSP | Prostate Secretory Protein of 94 amino acids |
| SDS | Sodium dodecyl sulfate |
| PAGE | Polyacrylamide gel electrophoresis |
| EDTA | Ethylene diamine tetra acetate |
| MWCO | Molecular weight cut off |
| A280 | Absorbance at 280 nm |
| MES | 2-Morpholinoethanesulfonic acid |
| HPLC | High performance liquid chromatography |
| RP-HPLC | Reverse phase HPLC |
| RPM | Rotation per minute |

The content of each publication, patent and patent application mentioned in the present application is incorporated herein by reference.

BRIEF DESCRIPTION OF THE DRAWINGS

In drawings which illustrates exemplary embodiment of the invention;

FIG. 3 is a graph showing anion-exchange chromatography results using a MacroPrep High Q anion exchange column, loaded with proteins purified by ammonium sulfate. Proteins are eluted with sodium chloride. The peak located between point A and B represents the protein fraction containing PSP94-binding protein. Proteins are detected and quantified by the absorbance measured at 280 nm;

FIG. 4 is a picture of a reducing sodium dodecyl sulfate-polyacrylamide gel electrophoresis (SDS-PAGE) gel loaded with samples obtained following PSP94-affinity chromatography. The gel was run in an electric field and stained with Gelcode® Blue Code Reagent (Pierce). Lane 1 represents the molecular weight marker. Lane 2 represents proteins bound to the PSP94-conjugated affinity matrix. Lane 3 represents proteins that bound to the PSP94-conjugated affinity matrix when excess free PSP94 was included within the incubation mixture;

FIG. 5 is a picture of a non-reducing SDS-PAGE gel loaded with samples obtained following the elution of the PSP94-binding protein from the PSP94-conjugated affinity matrix using different eluting (dissociation) conditions. After incubation, in the different eluting buffers, the affinity matrix was removed from the eluting buffer by centrifugation. The matrix was washed in PBS, and boiled in non-reducing SDS-PAGE sample buffer. The SDS-PAGE was run in an electric field and was stained with Gelcode® Blue Code Reagent (Pierce). Arrows represent the position of the high molecular weight binding protein (HMW) and the low molecular weight binding protein (LMW). Lane A represents the molecular weight marker. Lane B represents untreated sample. Lane C represents sample incubated for 1 hour in PBS at 34° C. Lane D represents sample incubated for 1 hour in water at 34° C. Lane E represents sample incubated with 300 μg of PSP94 in 1 ml of PBS at 34° C. Lane F represents the competition control. Lane G represents sample incubated in 2 M urea. Lane H represents sample incubated in 8 M urea. Lane I represents sample incubated in 100 mM sodium acetate at pH 2.7. Lane J represents sample incubated in 100 mM 3-(Cyclohexylamino)-1-propanesulfonic acid (CAPS) at pH 11.0;

FIG. 12B is a result of an ELISA assay using the method illustrated in FIG. 12a;

FIG. 12C is a schematic of a sandwich ELISA assay used to measure the amount of free PSP94;

FIG. 13 is a schematic of a proposed method used to measure the amount (PSP94 sandwich ELISA) of total PSP94 in a sample;

FIG. 14b is a result of an ELISA assay used to measure the PSP94-binding protein in a sample using the method illustrated in FIG. 14a;

DETAILED DESCRIPTION OF THE INVENTION

Figure 1:
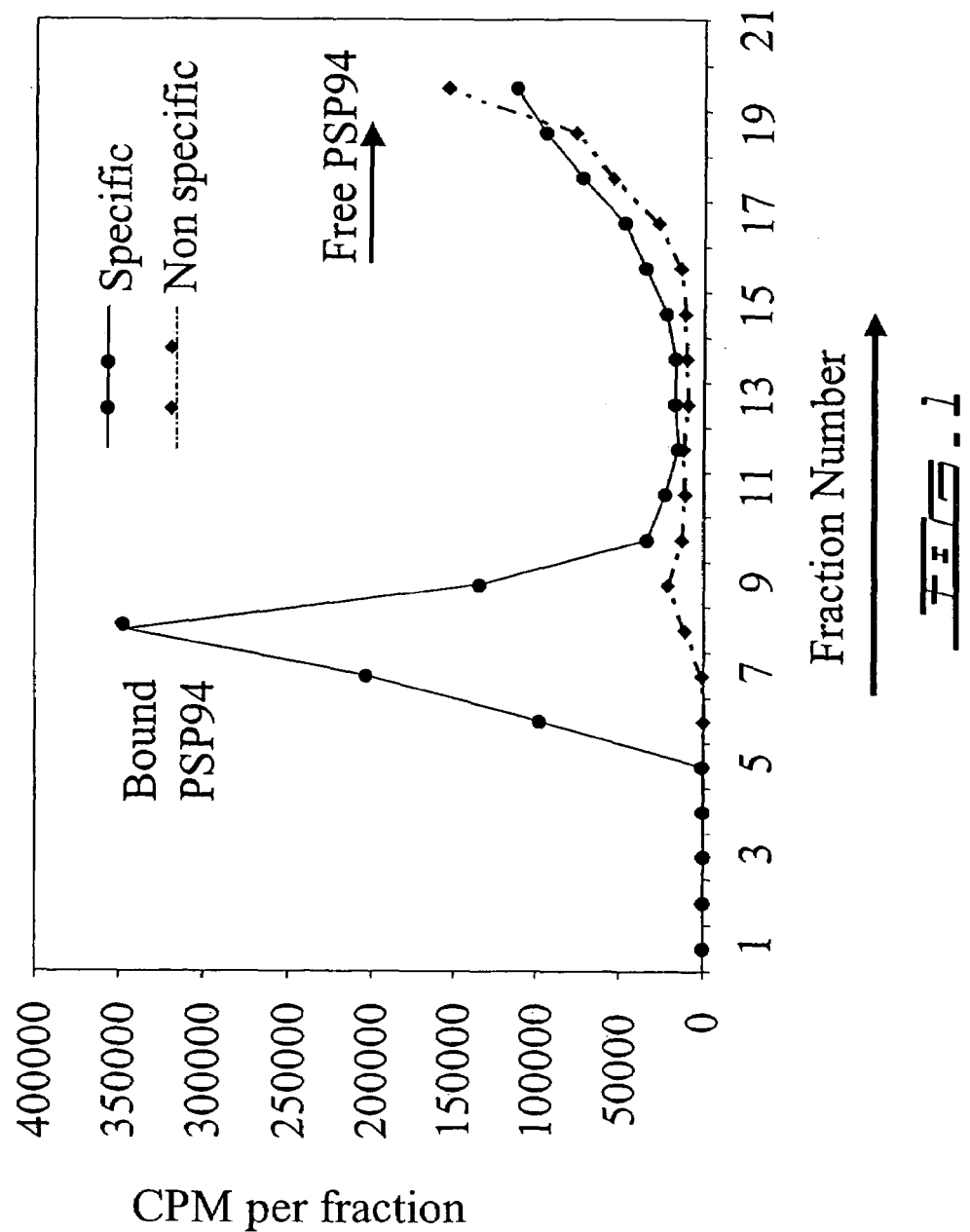
FIG. 1 is a graph showing size exclusion chromatography results of proteins from human male serum bound to PSP94 radiolabeled with isotope 125 of iodine ($^{125}$I) (specific binding). Binding of $^{125}$I-PSP94 to human male serum protein is determined by the radioactivity, expressed in counts per minute (cpm), in each fraction. Non-specific binding was determined by including free PSP94 in the incubation mixture together with human male serum and $^{125}$I-PSP94. The location of fractions containing free- and complexed-PSP94 (PSP94 associated with a carrier) are indicated in the graph.

PSP94 was used as bait in the isolation, identification and purification of a PSP94-binding protein. For that purpose, labeled-PSP94 was used to detect the presence of the PSP94- binding protein(s) in serum fractions that were submitted to various purification steps. In addition, PSP94 was used for affinity chromatography purification of the PSP94-binding protein. Examples described below illustrate the purification, identification and utility of the PSP94-binding protein.

PSP94 was also used for producing antibodies and for isolating, identifying and purifying anti-PSP94 antibodies.

EXAMPLE 1

Isolation of PSP94, Radiolabeling of PSP94 and PSP94-Binding Protein Kinetic Analysis Isolation and Purification of PSP94 from Human Seminal Plasma PSP94 was either prepared as described in Baijal Gupta et al. (Prot. Exp. and Purification 8:483-488, 1996) or alternatively, PSP94 was isolated and (substantially) purified as follow.

The procedures were carried out at 4° C. Semen samples (Bioreclamation) were thawed at 4° C. for 4-6 hours. Samples were pooled together and the volume was measured. A sample was kept for SDS-Page analysis. Samples were cleared of the sperms by centrifugation (4° C.) at 5000×g for 10 minutes.

Seminal plasma was precipitated overnight by adding 7 volumes of cold ethanol (without stirring). The next day, the sample was centrifuged (4° C.) at 3000 g for 10 min, washed twice with cold ethanol and was centrifuged between washings. Then, the pellet was resuspended with Endotoxin-free $H_2O$, to the original volume. The sample was transferred to a cold container about 4 times bigger in volume than the volume to lyophilise. Prior to lyophilisation, the sample were frozen by placing the Erlenmeyer at 45° in a slurry of dry ice/methanol and swirled until the seminal plasma was completely frozen, then it was lyophilised. This powder was found to be stable and was kept at −80° C. in a tight container filled with Nitrogen.

The mixture was reconstituted by adding 1 volume of endotoxin-free water (with reference to the original volume of seminal plasma) and 2 volumes of ice cold Buffer A (50 mM PBS pH 7.5, 2.5 mM EDTA pH 8.0, 1.5 mM PMSF), to which PMSF was freshly added, and was mixed to homogenise.

The pH of the reconstituted seminal plasma was adjusted to 6.0 using 0.1 M acetic acid and the volume of the resulting solution (pH 6.0) was measured.

Solid ammonium sulfate was added to from concentration of 0-30% (176 g/L) by slowly and constant stirring. The solution was stirred in cold for 1.5 hour.

The equilibration of cation exchange column was started with 10 mM sodium phosphate Buffer pH 6.3 according to the manufacturer's instructions for use the next day. The solution was transferred into appropriate centrifuge tubes and was centrifuged 60 min at 12,000×g in a refrigerated centrifuge.

The supernatant was saved and transfered into a fresh cold container. A sample was kept for SDS-Page analysis. The pellet was kept for record.

The supernatant volume was measured with a graduated cylinder. Ammonium sulfate was slowly added to the supernatant to obtain a final concentration of 30-70% (273 g/L). The mixture was stirred for 1.5 hour.

The solution was transferred into centrifuge tubes and was centrifuged 60 min at 12,000×g in a refrigerated centrifuge.

The pellet was saved and the supernatant was set aside. The pellets were scooped from each tube into a cold glass Dounce Tissue grinder. The pellet was dissolved in as small a volume of Buffer B (2.5 mM EDTA pH 8.0, 10 mM sodium phosphate pH 6.3) as possible (around 1 ml/2 ml of starting material).

A 1,000 MWCO dialysis tubing (Biolynk (Spectrum): 132103) for dialysis was prepared and the resuspended pellet was added to the tubing which was then sealed with clips. One volume of empty space was left to allow volume increase during dialysis. Dialysis was carried out against Buffer B overnight, using a container of around 15 liters of buffer. The next day, pH was verified to be similar or the same as buffer B.

Material was removed from dialysis tubing and was kept on ice. The material was tested by UV absorption at 280 nm. A sample was kept for SDS-Page analysis. Total protein concentration was calculated assuming that A280 (absorbance at 280 nm) of 1.0 equals to 1 mg/ml of protein.

The 200 mls Macro-prep High S Support column (BioRad: 156-0030, BioRad column: 737-5031) was used for a subsequent purification step. This column has a capacity of approximately 1600 mg of proteins. So, if needed, the sample may be divided for multiple runs making sure not to go over the capacity of the column.

Before loading the sample, the column was equilibrated with 10 mM Phosphate Buffer pH 6.3.

The dialysed, ammonium sulfate precipitated sample was loaded on the column. 10-13 mls fractions were collected and placed at 4° C.

Once the entire sample volume had passed into the column, further equilibration buffer (10 mM Phosphate Buffer, pH 6.3) was added. Fractions were collected until A280 measured below 0.1. Several fractions were analyzed on SDS-Page to determine the limit of PSP94 elution. Fractions containing PSP94 were pooled and all the other fractions (O.D.>0.1) are kept at −80° C. The volume of the pooled fractions was measured and the A280 read. Again, total protein concentration was calculated assuming that A280 (absorbance at 280 nm) of 1.0 equals 1 mg/ml of protein.

A sample of the pooled fractions was kept for SDS-Page analysis. The samples may be frozen or may be further purified by anion exchange.

Equilibration of the anion exchange column with 30 mM of Tris-HCl pH 8.8 was started according to the manufacturer's instructions.

The material collected from the cation column was pooled and brought to pH 8.8 using 2M Tris-HCl, pH 8.8. The final Tris concentration was below 50 mM. The protein concentration was kept at or higher than 0.8 mg/ml.

60 mls Macro-prep High Q Support (BioRad: 156-0040, BioRad column: 737-5031) column was used for a subsequent purification step. This column has a capacity of approximately 480 mg of proteins. So, if needed, the sample may be divided for multiple runs making sure not going over the capacity of the column.

Before loading the sample, the column was equilibrated with 30 mM Tris-HCl Buffer pH 8.8 (according to the manufacturer's instructions).

The sample was loaded on the column and 10-13 mls fractions were collected and placed at 4° C.

Once the entire sample volume had passed through the column, 50 mM Tris-HCl pH 8.8 (washing buffer) was added until the A280 returned to baseline. Stepwise elution with 250 mM Tris-HCl pH 8.8 until the A280 reached baseline was performed. A final elution with 300 mM Tris-HCl pH 8.8 until the A280 reached baseline was carried out. When no peak was seen, elution was continued with 350 mM Tris-HCl pH 8.8 and 400 mM until a peak was observed. Samples were kept for SDS-Page analysis. Fractions that did not contain pure PSP94 were frozen.

Fractions that contained pure PSP94 protein were pooled and concentrated with Amicon concentrator using a 1,000 MWCO membrane (molecular weight cut-off) according to the manufacturer's instructions (VWR: 29300-714) until the volume was approximately 10 ml. Dialysis was carried out for 18 hrs against 500-1000× volumes of 10 mM PBS pH 7.4.

Regeneration and packing of Detoxi-gel columns was performed according to the manufacturer's instructions (Biolynx: 20339). The regenerated matrix of one of the two columns was added to a 15 ml of 50 ml tube along with concentrated PSP94 and was incubated for 1 hr at room temperature on a rocking platform.

After incubation, the material was slowly transferred on the other packed column. All material was collected with gravity flow, on ice. Once all the material had passed into the column, cell culture grade PBS (endotoxin-free, Wisent (Multicell): 21 031CV) was added and the material was collected until A280 was lower than 25.

The optical density was measured and protein concentration was calculated as indicated above. When PSP94 (protein) concentration was more than 1 mg/ml, there was no need to concentrate the material. However, when the protein concentration was lower, 1,000 MWCO centrifuge concentrators were used to bring it to at least 1 mg/ml and the filter was rinsed with cell culture grade PBS to remove PSP (PSP94) completely.

The material was sterilized by filtration using a 0.22 um syringe filter (ex. Millex: SLGP033RS). Aliquots were made in cryogenic tubes provided with a rubber sealing to prevent evaporation and were frozen at −80° C. Some aliquots were kept for characterization.

Multiple analyses were done to assess the purity, concentration and 'activity' of PSP94. For example, SDS-Page using coomassie and silver staining (e.g. using a 12% Polyacrylamide gel with MES buffer (Invitrogen NP0342BOX, NP0002)), Western blot using for example, the P1E8 antibody, endotoxin level (Charles River), Elisa to measure the binding capacity to the PSP Binding Protein, amino acid sequencing, Mass Spectrometry and RP-HPLC. Results of PSP94 purification are presented in Table A.

Baijal Gupta et al. (Prot. Exp. and Purification 8:483-488, 1996) in 15 microliters of 100 mM sodium bicarbonate (pH 8.0) was labeled using one millicurie of mono-iodinated Bolton-Hunter reagent at 0° C. following the manufacturer's instructions (NEN Radiochemicals). The reaction was terminated after 2 hours by the addition of 100 microliters of 100 mM glycine. The free iodine was separated from the iodine incorporated into the PSP94 by a PD10 disposable gel filtration column according to manufacturer's instructions (BIO-RAD). Typically, the proportion of iodine that became incorporated into the PSP94 protein was about 60%, giving a specific activity of about 30 microcuries per microgram of PSP94.

Optimization of the binding assay of human male serum proteins to $^{125}$I-PSP94 was performed in order to identify the optimal incubation time, temperature, and separation conditions. Equilibrium (e.g., no further significant increase in binding as incubation time lengthens) was approached after a considerable incubation time at 37° C., so a 16 hours incubation time was selected. Separation of the complexed form (i.e., bound form) PSP94 (or complexed-$^{125}$I-PSP94), having a higher molecular weight and the free-PSP94 (or free-$^{125}$I-PSP94), having a low molecular weight, was effected by gel filtration chromatography, using Sephadex G100 resin (Amersham Pharmacia Biotech Ltd) packed into a 1×20 cm column. The molecular sieve chromatography was performed at 4° C. since at higher temperatures dissociation of the complex during the procedure was shown to be significant.

Based on the optimization results described above, radioligand binding analysis of PSP94-binding serum components (i.e., PSP94-binding protein) was performed. This assay was done in a total volume of 500 microliters. The test samples contained PSP94-binding protein (neat serum, or fractions from purification trials) 50 ng of radiolabeled PSP94, with or without excess free competitor (10 micrograms free PSP94 (unlabeled)) in phosphate buffered saline-gelatin (PBS-gelatin: 10 mM sodium phosphate, 140 mM NaCl, 0.1% gelatin (Fisher Scientific, Type A), pH 7.5, including 8 mM sodium azide as an antibacterial agent). Those were incubated for 16 hours at 37° C. At this time, the equilibrated mixture was

TABLE A

| Step | Volume (ml) | *Total proteins (mg) | ⁰Total PSP94 (Elisa)(mg) | % Recovery of PSP94 | ⁺Purification (folds) |
|---|---|---|---|---|---|
| Seminal Plasma | 70 | 2,200 (100) | 49 | 100 | — |
| Ammonium Sulfate | 40 | 1,300 (59) | 37 | 76 | 1.3 |
| Macro-Prep Hi S | 125 | 180 (8.2) | 33 | 68 | 8.3 |
| Macro-Prep Hi Q | 15 | 37 (1.7) | 27 | 55 | 32.4 |

Percentage yields based on the total protein in seminal plasma are indicated in parentheses ( )
*Total Protein estimated using Macro-BCA (BSA as a standard)
⁰Total PSP94 based on UV Abs 280 1.53 = 1 mg/ml
⁺Purification (folds) = % Recovery of PSP94/Percentage yield Preparation of Labeled PSP94

Experiments to optimize $^{125}$I-PSP94 labeling, $^{125}$I-PSP94 binding assay to human male serum proteins and development of means to separate free—(i.e., unbound) and complexed—(i.e., bound, associated) $^{125}$I-PSP94 were undertaken. Human male serum protein(s) that will bind to PSP94 (in the present case; $^{125}$I-PSP94) will generate the formation of a complex of higher molecular weight than free-PSP94 (or free $^{125}$I-PSP94).

Iodination of PSP94 was performed as followed. Twenty micrograms of native human PSP94 prepared as described in placed on ice, and the components separated according to their molecular weight by molecular sieve chromatography at 4° C. using a 1×20 cm sephadex G100 column equilibrated with PBS-gelatin. After the sample had run into the column, 3 ml was discarded, and 20 fractions of 0.5 ml were collected. A single fraction of 30 ml was also collected at the end of the run.

The radioactivity (expressed in counts per minute (cpm)) in the collected fractions was measured using an LKB rack gamma counter, and the total radioactivity in the high molecular weight peak (generally contained within fractions 4-14) and low molecular weight peak (the remainder of the 0.5 ml fractions and the single 30 ml fraction) were calculated. A typical elution profile is illustrated in FIG. 1.

FIG. 1 shows size exclusion chromatography results of proteins from human male serum bound to PSP94 radiolabeled with isotope 125 of iodine ($^{125}$I) (i.e., $^{125}$I-PSP94) (specific biding). Binding of $^{125}$I-PSP94 to human male serum protein is determined by the radioactivity, expressed in counts per minute (cpm), in each fraction. Non-specific binding was determined by including 10 µg of free PSP94 in the incubation mixture together with 250 µl of human male serum and 50 ng of $^{125}$I-PSP94. The location of fractions containing free—(i.e., unbound) and complexed (i.e., bound)-PSP94 are indicated in the graph. The majority of the free PSP94 ($^{125}$I-PSP94) eluted later than fraction 20. Typically, about 33% of the total radioactive PSP94 added to the 250 microliters of human serum eluted in the earlier fractions as part of the PSP94-binding protein complex, and about 67% of the radioactive PSP94 remained uncomplexed eluting in the later fractions. In the competitive control, with the inclusion of 10 micrograms of unlabelled PSP94 in the incubation mixture, only about 3% of the radioactive PSP94 eluted in the earlier fractions as part of a high molecular weight complex, confirming the specificity of the PSP94 for the PSP94-binding protein.

Using this methodology, and by varying the concentration of radiolabeled and competing PSP94 and maintaining the quantity of human male serum, constant (250 µl) it was possible to perform kinetic analysis of the equilibrium binding data. Assuming that PSP94 is about one fifth of the molecular weight of a PSP94-binding protein, this would suggest that each milliliter of serum has about 1 microgram of PSP94-binding protein. The total protein content of serum is about 80 milligrams per milliliter, so the PSP94-binding protein:total protein ratio in serum is approximately 1:80,000.

Further information from radioligand binding analysis indicated that a PSP94-binding protein is present in human female serum, virgin female human serum, fetal bovine serum, and pooled mouse serum.

EXAMPLE 2

Ammonium Sulfate Precipitation

From the kinetic results obtained in example 1, it was shown that the PSP94-binding protein was poorly abundant in human serum.

Figure 2:
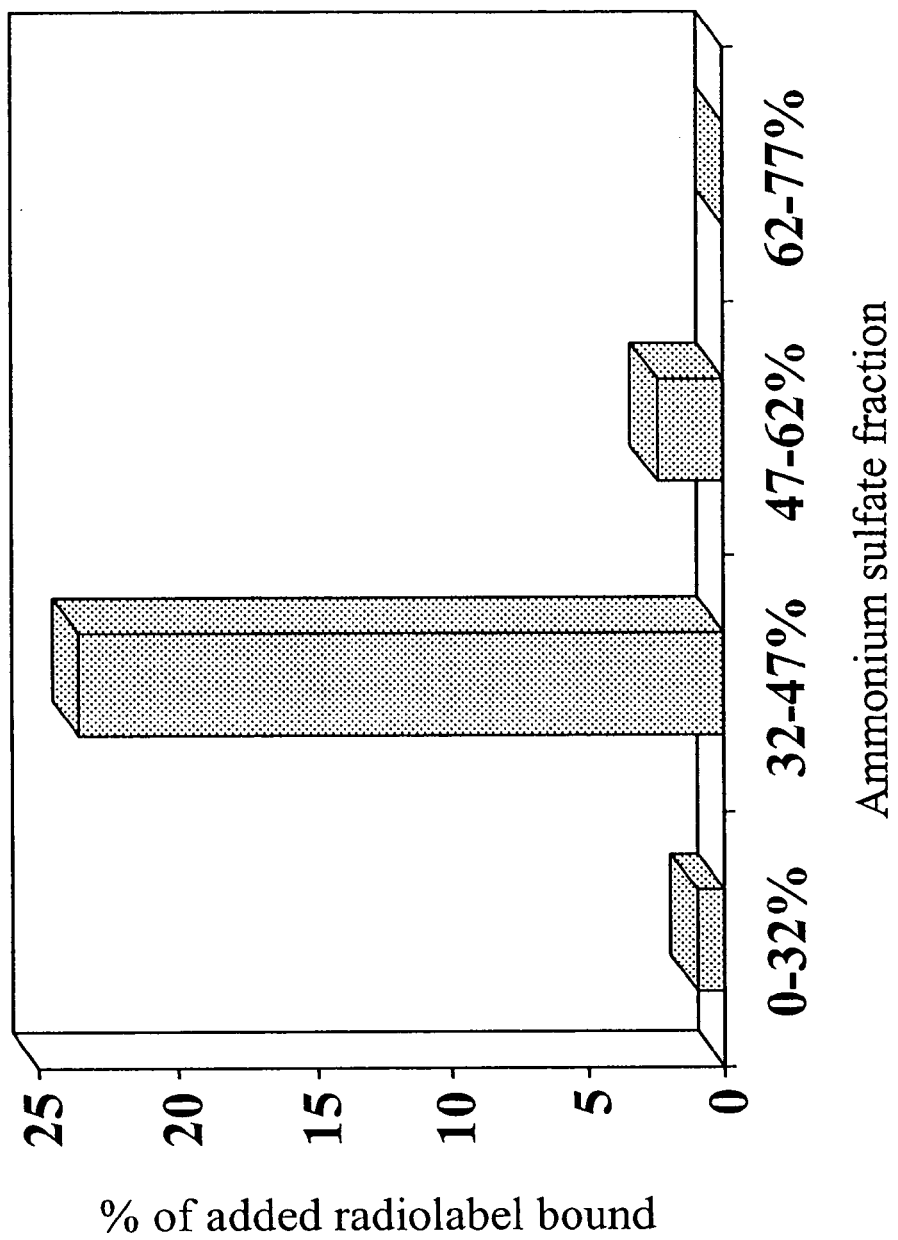
FIG. 2 is a graph depicting results of $^{125}$I-PSP94 binding in fractions of proteins, from human male serum, partially purified by ammonium sulfate precipitation. Whole human male serum was precipitated with various concentrations of ammonium sulfate (0 to 32%, 32 to 47%, 47 to 62% and 62 to 77% of ammonium sulfate (% are calculated in w/v)), and the presence of PSP94-binding activity within the fractions was assessed by measuring the ability of radiolabeled PSP94 to associate with proteins contain in each fraction (high molecular weight components) of serum. Results are expressed as the amount of radioactivity bound to human male serum proteins in each fraction relative to the total amount of radioactivity used in the binding assay (in terms of percentage)

In order to isolate a PSP94-binding protein for further characterization and identification, a first purification step was performed by ammonium sulfate precipitation. To establish the appropriate concentration of ammonium sulfate necessary to precipitate a PSP94-binding protein, small scale ammonium sulfate precipitation trials were performed. The presence of a PSP94-binding protein in the precipitate was determined after dissolution and dialysis against PSP94 by radioligand binding analysis as discussed in example 1. These trials determined that the 32-47% ammonium sulfate fraction contained the vast majority of a PSP94 binding material as illustrated in FIG. 2.

Ammonium sulfate precipitation was routinely performed on a larger scale. Briefly, 1 liter of male frozen serum (Bioreclamation Inc, New York) was thawed and added to 1 liter of cold 10 mM Sodium Phosphate, 140 mM NaCl, pH 7.5 (phosphate buffered saline; PBS), and to this 370 g of ammonium sulfate (BDH ACS reagent grade) was added slowly under constant stirring to bring the ammonium sulfate concentration up to 32%. After dissolution of the salt, the mixture (i.e., male serum containing ammonium sulfate) was stirred for 20 minutes before centrifugation at 5,000×g for 15 minutes.

The pellet was discarded, and the supernatant fraction of proteins containing a PSP94-binding protein was collected. Further ammonium sulfate (188 g) was added slowly under constant stirring to the supernatant fraction, bringing the total ammonium sulfate concentration to 47%. After 20 minutes, this mixture was also spun at 5,000×g, the supernatant was discarded, and the pellet was dissolved in a total of 500 ml of 10 mM MES ((2-[N-Morpholino]ethanesulfonic acid) hydrate), 100 mM NaCl, pH 6.5. This pellet was dialyzed using 6-8,000 molecular weight cut off dialysis tubing (Spectra/Por, Fisher Scientific Canada) with 16 liters of 10 mM MES, 100 mM NaCl, pH 6.5 for 16 hours at 4° C. followed by another dialysis step using a further 16 liters of the same buffer for an additional 7 hours. The protein concentration within the product was measured using 280 nm ultraviolet (UV) absorbance and the preparation was stored at −20° C. in 4 g of protein aliquots (generally about 150 ml). A typical ammonium sulfate precipitation assay is shown in FIG. 2.

EXAMPLE 3

Ion-Exchange Chromatography Assays

Ion exchange chromatography (IEX) separates molecules based on their net charge. Negatively or positively charged functional groups are covalently bound to a solid support matrix yielding a cation or anion exchanger. When a charged molecule is applied to an exchanger of opposite charge it is adsorbed, while neutral ions or ions of the same charge are eluted in the void volume of the column. The binding of the charged molecules is reversible, and adsorbed molecules are commonly eluted with a salt or pH gradient.

Without prior knowledge of any characteristics of the PSP94-binding protein, the ability of anion and cation exchange matrices to absorb a PSP94-binding protein at a range of pH values was determined in a series of ion-exchange assays. Aliquots of ammonium sulfate precipitated serum were exchanged into the buffers indicated in table 3 using a Biorad DG 10 column equilibrated with the appropriate buffer according to the manufacturer's instructions. Seven hundred microliters aliquots were incubated with 500 microliters of ion-exchange matrix (prepared according to the manufacturer's recommendations). After incubation for 90 minutes at room temperature with gentle agitation, the mixture was spun at 1000×g for 5 minutes to separate the matrix from the supernatant. If a PSP94-binding protein is bound (adsorbed) to the matrix, it will remain bound to it after centrifugation and will not be present in the supernatant. The supernatant was immediately neutralized with 0.3 volumes of 250 mM TRIS pH 7.5 and 250 microliters of this solution was assessed in the $^{125}$I-PSP94 binding assay described herein (example 1). Conditions tested and results of these assays are presented in table 3.

TABLE 3

| Buffer | | $^{125}$I-PSP94 binding before incubation with matrix | $^{125}$I-PSP94 binding after incubation with matrix |
|---|---|---|---|
| Cation Matrix: Macro Prep High S (BIORAD) | | | |
| pH 4.7 | 10 mM Citrate | 9.5% | 0.08% |
| pH 5.7 | 10 mM MES | 11.9% | 7.7% |
| pH 6.7 | 10 mM MES | 20.6% | 18.6% |
| pH 7.9 | 10 mM MOPS | 20.5% | 11.9% |

TABLE 3-continued

| Buffer | | $^{125}$I-PSP94 binding before incubation with matrix | $^{125}$I-PSP94 binding after incubation with matrix |
|---|---|---|---|
| Anion Matrix: Macro Prep High Q (BIORAD) | | | |
| pH 5.7 | 10 mM MES | 11.9% | 0.73% |
| pH 6.7 | 10 mM MES | 20.6% | 0.66% |
| pH 8.0 | 10 mM Bicine | 14.1% | 0.81% |
| pH 9.0 | 10 mM Bicine | 12.5% | 0.65% |

The major findings from these ion-exchange chromatography assays indicate that temporary exposure of a PSP94-binding protein to extremes of pH (8 and above, and 6 and below) resulted in a reduced ability of a PSP94-binding protein to bind to PSP94, suggesting that a PSP94-binding protein is pH sensitive. No adsorption of PSP94-binding protein to the cation matrix was seen at pH 4.7. Some adsorption to the cation matrix was seen at pH 5.7 and maximal adsorption was seen at pH 6.7. These results may suggest an isoelectric point of about pH 5.

The anion-exchange chromatography assays indicated good adsorption of a PSP94-binding protein to the matrix between pH 5.7 and 9.0, consistent with an isoelectric point of 5. It was clear that a preferred purification strategy would have to use the anion-matrix, because good adsorption could be attained at neutral (non-denaturing) pH values. So the anion-exchange matrix, and the 10 mM MES buffer at pH 6.5 was selected for further work using salt concentration elution rather than pH elution.

Optimization of conditions of PSP94-binding protein elution from the anion-exchange matrix was performed using various sodium chloride concentration.

A column (1×15 cm) containing Macro Prep High Q was equilibrated with buffer containing 10 mM MES, 100 mM NaCl, pH 6.5 and run at 0.5 ml per minute. Seven milliliters of the 32-47% ammonium sulfate cut (i.e., starting material of table 4) equilibrated into the same buffer, was applied to the column, and various buffers were applied to elute a PSP94-binding protein. The eluant was monitored with a UV recorder. The fractions were collected, and buffer was exchanged into PBS using CentriPrep concentrators with a molecular weight cut off of 10 kDa (Amicon). These samples were tested in the $^{125}$I-PSP94 binding assay described in example 1. Table 4 summarizes the different conditions used and the results obtained in this experiment. A star (*) indicate that some losses was experienced during buffer exchange. Protein concentrations were estimated from absorbance at 280 nm (A280) with 1 OD unit equivalent to 1 mg of protein.

TABLE 4

| Sodium chloride concentration | Total protein Eluted (mg) | Total protein in binding assay | % $^{125}$I-PSP94 bound |
|---|---|---|---|
| Starting material (ammonium sulfate cut) | 179 mg* | 7.2 mg | 12.7% |
| 100 mM (flow through) | 50 mg | 0.67 mg | 0.89% |
| 200 mM | 37 mg | 0.80 mg | 1.4% |
| 300 mM | 12 mg | 0.63 mg | 24.4% |
| 400 mM | 5 mg | 0.30 mg | 1.5% |
| 500 mM | 8 mg | 0.62 mg | 0.9% |
| 1000 mM | 7 mg | — | — |

From these data, it is clear that the buffer containing 300 mM NaCl was effective and would be preferably used for eluting a PSP94-binding protein from the anion-exchange matrix. Using these results, a scale up ion-exchange protocol was developed allowing the application of 4 g of ammonium sulfate precipitated serum extract to a 5 cm×12 cm anion-exchange matrix as described below.

EXAMPLE 4

Large-Scale Anion-Exchange Chromatography Purification of PSP94-Binding Protein

An anion exchange column (5 cm diameter×12 cm length, Macro-Prep Hi Q, Biorad) was prepared and equilibrated in accordance with the manufacturer's guidelines in 10 mM MES, 100 mM NaCl, pH 6.5 and run at room temperature with a flow rate of about 3 ml per minute. An aliquot of ammonium sulfate precipitated serum (from example 2; 4 g total protein in about 150 ml of solution) was applied to the column which, was then washed with about 250 ml of 10 mM MES, 100 mM NaCl, pH 6.5 (FIG. 3). Elution was performed with about 400 ml of 10 mM MES, 200 mM NaCl, pH 6.5 buffer, followed by elution with 10 mM MES, 300 mM NaCl. The 300 mM eluting fraction was collected (FIG. 3). The profile of the eluting proteins was monitored by UV absorbance at 280 nm on a chart recorder. A typical profile is illustrated in FIG. 3. FIG. 3 is a graph showing anion-exchange chromatography results using a MacroPrep High Q anion exchange column, loaded with proteins purified by ammonium sulfate (about 4 grams). Proteins are eluted with stepwise increases in sodium chloride concentration. The peak located between point A and B represents the protein fraction containing a PSP94-binding protein. Proteins are detected by the absorbance measured at 280 nm.

The column could be regenerated with 10 mM MES, 1 M NaCl, pH 6.5 (300 ml) followed by an equilibration with 500 ml of 10 mM MES, 100 mM NaCl, pH 6.5. Sodium azide was added to this buffer at 0.05% (w/v) for storage of the column for greater than 24 hours.

The 300 mM fraction (about 90 ml) was collected (between markers A and B, FIG. 3) and this was shown previously to contain the majority of a PSP94-binding activity. This preparation identified "partially pure PSP94-binding protein" (PPBP) was concentrated to about 20 ml in centrifugal concentrators according to the manufacturer's instruction (Centriprep 10, Amicon) diluted with PBS to 60 ml, concentrated to 20 ml, further diluted with PBS to 60 ml, concentrated to 20 ml, and finally diluted with PBS to give a solution with an A280 of 2.0 (generally a final volume of about 150 ml). This solution was stored at −20° C. After a total application of 20 g of protein (5 cycles) the column was sanitized using 1 M NaOH and re-equilibrated in 10 mM MES, 100 mM NaCl, pH 6.5 using the protocol described by BIORAD.

Ammonium sulfate fractionation (i.e., precipitation) and anion exchange chromatography have resulted in approximately 4 fold and 10 fold purification of a PSP94-binding protein respectively. In neat serum, estimations indicated that the ratio of PSP94-binding protein:total protein was 1:80,000. The efficiency of the two protein purification steps described in example 2 and example 4 were monitored using the PSP94 radioligand binding assay described in example 1. In both steps, the vast majority of the PSP94 binding material was confined within a single fraction. From this information, it appears that in combination, these two steps result in an efficient purification process with little loss (qualitatively) of the PSP94 binding material. However, assuming losses are small, the partially purified binding protein (PPBP) yielded by the combination of the two protein purification steps described in examples 2 and 4, should contain about 1 part of binding protein: 2000 parts of other proteins, by mass.

EXAMPLE 5

Affinity Chromatography Assays

Preparation of affinity matrix for PSP94-binding protein purification was performed as followed. Approximately 0.5 g of cyanogen bromide activated sepharose CL 4B (Sigma Chemical Company) was swelled in 1 mM HCl and prepared as per the manufacturer's recommendations. To 1 ml of this matrix, 5 ml of a solution containing 5 mg of PSP94 purified as described in Baijal Gupta et al. (Prot. Exp. and Purification 8:483-488, 1996) in 100 mM $NaHCO_3$ 0.5 M NaCl, pH 8.0 was added and the reactants incubated at 4° C. with periodic agitation. At time intervals, the reactants were spun at 200×g for 2 minutes, and the absorbance at 280 nm (A280) expressed in optical density (OD) units, of an aliquot of supernatant was measured in order to determine the proportion of binding of PSP94 to the matrix. Results showing the time course of conjugation (i.e., binding) of PSP94 to the activated sepharose (i.e., matrix) are summarized in table 5.

TABLE 5

| Duration of reaction (min) | A280 (OD) units not bound to matrix | A280 (OD) units bound to matrix | % of PSP94 incorporation |
|---|---|---|---|
| 0 (start) | 5.1 | 0 | 0 |
| 5 | 4.7 | 0.48 | 9.6 |
| 15 | 3.0 | 2.1 | 41 |
| 30 | 2.0 | 3.1 | 61 |
| 60 | 1.6 | 3.5 | 69 |

The conjugation reaction was continued until 70-80% of the PSP94 had bound to the matrix (after about 60 minutes in the preparation illustrated in table 5). At this time, 1 ml of 200 mM glycine was added to block any further reactive groups and the slurry was incubated overnight at 4° C. with gentle agitation. The matrix was washed according to the manufacturer's recommendations and diluted in PBS to give a slurry with a concentration with respect to PSP94 of 1 microgram per microliter. Sodium azide ($NaN_3$) was added to 0.05% as an anti-microbial agent.

Based on the results of optimization assay described above, a PSP94 affinity matrix was prepared by conjugating PSP94 to cyanogen bromide activated sepharose. The matrix typically had 4 micrograms of PSP94 per microliter of packed matrix, and a working slurry with 1 microgram of PSP94 per microliter was prepared by dilution with PBS containing 0.05% $NaN_3$. The PSP94 affinity matrix (at a concentration of 5 micrograms per milliliter with respect to PSP94) was added to the partially pure PSP94-binding protein. Tween 20 at a concentration of 0.1% (v/v) and $NaN_3$ at 0.05% (w/v) were also included in the mixture, which was then incubated at 34° C. for 18 hours on a rocking table. In a parallel control experiment, free-PSP94 was also added at a concentration of 50 micrograms per milliliter. The addition of free PSP94 in this control experiment would compete with the PSP94 conjugated to the matrix for the binding of a PSP94-binding protein. This will reverse the binding of a PSP94-binding protein to the affinity column thus enabling the identification of proteins specifically binding to PSP94. The affinity matrix was separated from the supernatant by rapid filtration, and the matrix was extensively washed in PBS at 4° C. The matrix was collected and boiled in sodium dodecyl sulfate-polyacrylamide gel electrophoresis (SDS-PAGE) reducing sample buffer (final concentration in sample: 5 mM Tris pH 6.8, 2% (w/v) SDS, 10% glycerol (v/v), 8 mM dithiothreitol, 0.001% Bromophenol blue) to dissociate the bound proteins and these were resolved by 7.5% SDS-PAGE. Result of this experiment is illustrated in FIG. 4

FIG. 4 shows results of a sodium dodecyl sulfate-polyacrylamide gel electrophoresis (SDS-PAGE) loaded with samples obtained following PSP94-affinity chromatography. The gel was run in an electric field and stained with Coomassie Brilliant Blue. Lane 1 represents the molecular weight marker (Kaleidoscope prestained standards, Bio-Rad). Lane 2 represents proteins bound to the PSP94-conjugated affinity matrix. Lane 3 represents proteins bound to PSP94-conjugated affinity matrix and incubated with excess of PSP94. Note that at least two proteins, A and C, remain present in the two lanes, (lane 2 and 3). Two bands, B and D, are present in the lane 3 but not in the control experiment (lane 2). These bands (B and D) are likely to be specific PSP94-binding proteins.

EXAMPLE 6

Optimization of PSP94-Binding Protein Elution from the PSP94-Affinity Matrix

A range of conditions were assessed in order to dissociate a PSP94-binding protein from the affinity matrix using less denaturing conditions than boiling in SDS-PAGE sample buffer (either in non-reducing conditions or not). Conditions tested are summarized in table 6. Undenatured active PSP94-binding protein is required for antibody generation and further experimentation and development. Aliquots of PSP94-affinity matrix that had been pre-incubated with partially pure PSP94-binding protein and washed (i.e., with binding protein attached) were incubated for 1 hour in the elution (dissociation) conditions listed in table 6. After incubation, the affinity matrices were removed from the eluting buffers by centrifugation. The matrices were washed in PBS, and boiled in non-reducing SDS-PAGE sample buffer (final concentration in sample: 5 mM Tris pH 6.8, 2% (w/v) SDS, 10% glycerol (v/v), 0.001% Bromophenol blue) and proteins were resolved on 7.5% SDS-PAGE. If proteins remains associated with the matrix after elution, the conditions are not suitable for an appropriate dissociation. Thus if a PSP94-binding protein is absent from the SDS-PAGE illustrated in FIG. 5, elution (dissociation) conditions are suitable. Non-reducing conditions were found to provide superior separation conditions, because the major contaminating band was left at the top of the gel, rather than between the two PSP94-binding protein bands. Conditions tested and results of this experiment are illustrated in FIG. 5 and summarized in table 6.

TABLE 6

| Lane | Dissociation conditions | Effect on PSP94-binding protein |
|---|---|---|
| A | Molecular weight marker | — |
| B | No treatment | None |
| C | 1 hour in PBS at 34° C. | None observable |
| D | 1 hour in water at 34° C. | None observable |
| E | 300 µg PSP94 in 1 ml PBS at 34° C. | Near total elution from matrix |
| F | (Competition control) | (near full competition) |
| G | 2 M urea | None observable |
| H | 8 M urea | Some loss of binding |
| I | 100 mM sodium acetate pH 2.7 | Some loss of binding |
| J | 100 mM CAPS pH 11.0 | Some loss of binding |

FIG. 5 shows a SDS-PAGE loaded with samples obtained following the elution of a PSP94-binding protein from the PSP94-conjugated affinity matrix using different eluting (dissociation) conditions. After incubation, in the different eluting buffers, the affinity matrix was removed from the eluting buffer by centrifugation. The matrix was washed in PBS, and boiled in non-reducing SDS-PAGE sample buffer. The SDS-PAGE was run in an electric field and was stained with Gelcode® Blue Code Reagent (Pierce). Arrows represent the position of the high molecular weight binding protein (HMW) and the low molecular weight binding protein (LMW). Lane A represents the molecular weight marker (Kaleidoscope prestained standards, Bio-Rad). Lane B represents untreated sample. Lane C represents sample incubated for 1 hour in PBS at 34° C. Lane D represents sample incubated for 1 hour in water at 34° C. Lane E represents sample incubated with 300 μg of PSP94 in 1 ml of PBS at 34° C. Lane F represents the competition control, where the matrix was incubated with the PPBP in the same way as the sample from lane B, but included in this incubation was a saturating excess of free PSP94. Lane G represents sample incubated in 2 M urea. Lane H represents sample incubated in 8 M urea. Lane I represents sample incubated in 100 mM sodium acetate at pH 2.7. Lane J represents sample incubated in 100 mM 3-(Cyclohexylamino)-1-propanesulfonic acid (CAPS) at pH 11.0.

From the experiment described above, it is clear that a PSP94-binding protein and PSP94-affinity matrix interaction was highly stable under a variety of conditions. Some dissociation was seen with 8 M urea, and extremes of pH, however these denaturing conditions were less favored than non-denaturing competitive dissociation using excess free ligand (i.e., PSP94). This approach was therefore selected in order to purify the active PSP94-binding protein.

Data indicate that the HMW and LMW bands of FIG. 5 are the same as bands B and D of FIG. 4, respectively.

EXAMPLE 7

PSP94-Binding Protein Purification by PSP94-Affinity Chromatography

Figure 6:
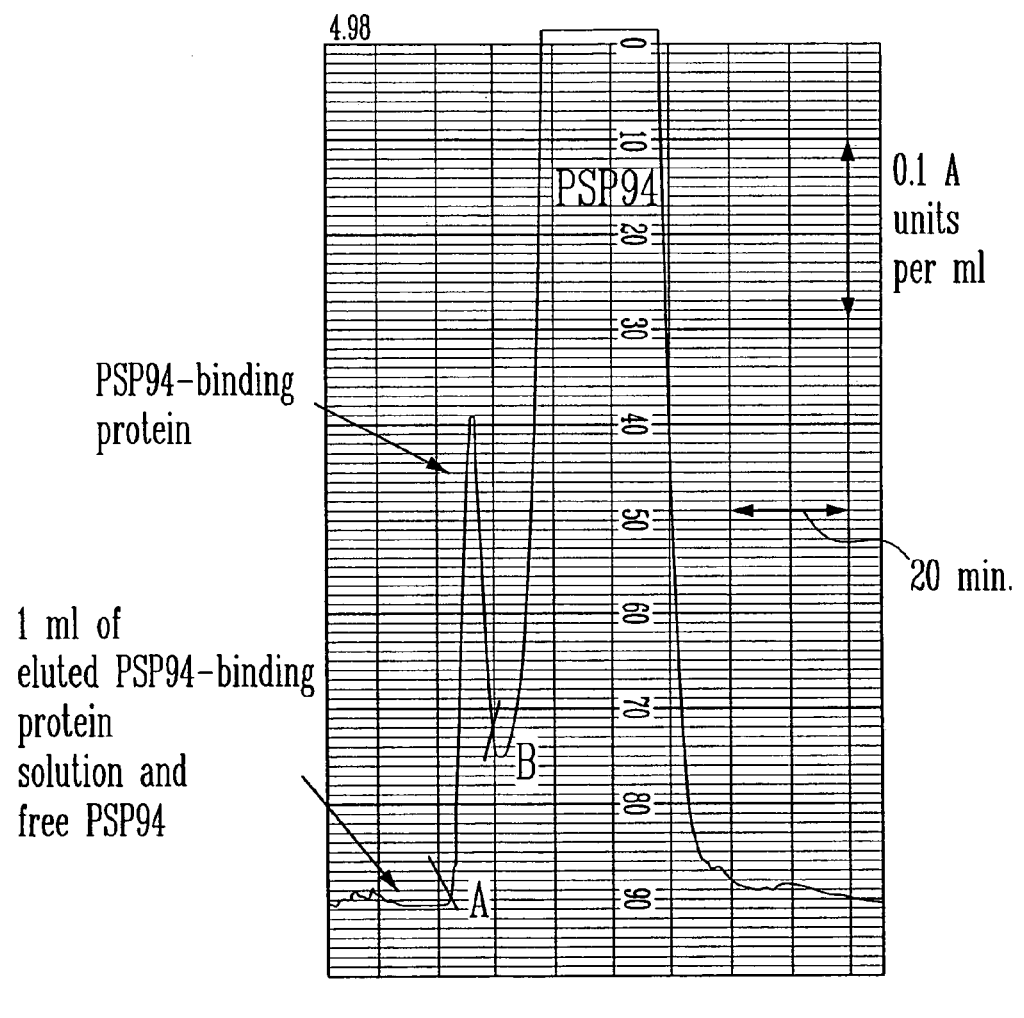
FIG. 6 is a graph showing affinity chromatography (using PSP94-conjugated affinity matrix) results of samples purified by ammonium sulfate precipitation followed by anion-exchange chromatography. PSP94-binding protein was eluted from the column by adding excess PSP94. The peak located between point A and B represents the PSP94-binding protein fraction. Proteins are detected and quantified by the absorbance at 280 nm.

One hundred milliliters of partially pure PSP94-binding protein (preparation generated as described in example 4), containing 0.1% (v/v) Tween-20 and 0.05% (w/v) NaN$_3$, was incubated with 250 micrograms (with respect to PSP94) of affinity matrix for 16 hours at 34° C. The matrix was separated from the soluble fraction by rapid filtration using a disposable Poly-Prep Column (Bio Rad). The liquid was forced through the column by applying air pressure from a 10 ml syringe attached to the column end cap. The matrix was washed three times with 10 ml of ice cold PBS similarly, and the matrix was collected from the column's polymer bed support with a micropipette. The matrix was resuspended in 1 milliliter of 10 mM sodium phosphate, 500 mM NaCl pH 7.5 containing 2 mg of free PSP94 and incubated with gentle agitation for 5 hours at 34° C. The matrix was then separated from the solution by centrifugation (1000×g for 30 seconds) and the supernatant (containing the eluted PSP94-binding protein and free PSP94) was resolved by molecular sieve chromatography at room temperature using a 1×20 cm sephadex G100 column equilibrated with 10 mM sodium phosphate, 500 mM NaCl, pH 7.5 and run at a flow rate of approximately 0.7 ml per minute. The absorbance at 280 nm of the eluant was recorded on a chart recorder (FIG. 6). Qualitative assessments of PSP94-binding protein capture, elution, and purified product were made by non-reducing 7.5% SDS-PAGE (FIG. 7).

FIG. 6 shows affinity chromatography (using PSP94-conjugated affinity matrix (Sephadex G-100)) results of samples purified by ammonium sulfate precipitation and anion-exchange chromatography. PSP94-binding protein was eluted from the column by adding excess PSP94 (free-PSP94). The high molecular weight proteins were collected (between points A and B) in a total volume of 4 ml. This solution was buffer exchanged into PBS (150 mM NaCl) using centrifugal concentrators (Centricon-10 from Amicon) and concentrated to approximately 100 ng per microliter. Typical yield=40 micrograms from 100 ml of PPBP starting material. The peak located between points A and B represents a PSP94-binding protein fraction. Proteins are detected and quantified by the absorbance measured at 280 nm. Results obtained indicate a proper separation between free PSP94 and a PSP94-binding protein.

Figure 7:
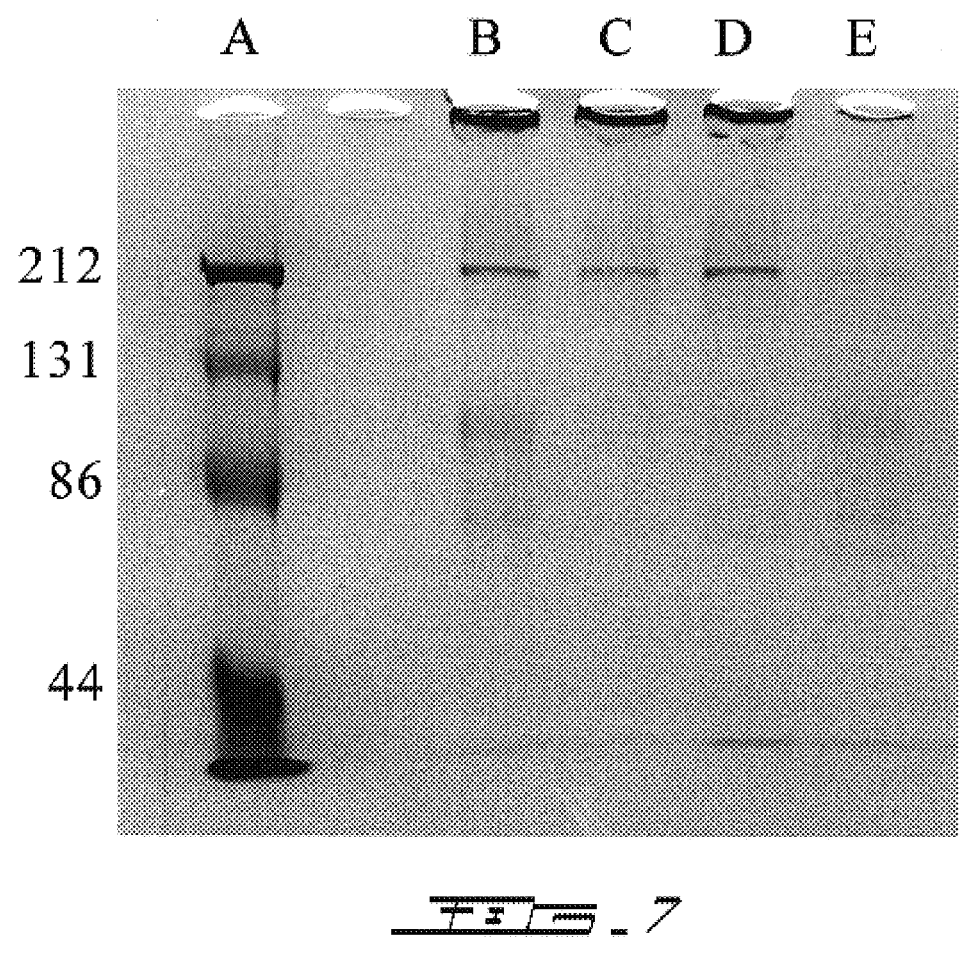
FIG. 7 is a picture of a SDS-PAGE performed in non-reducing conditions. Lane A is the molecular weight marker. Lane B represents the PSP94-affinity matrix after incubation with PSP94-binding protein purified by ammonium sulfate precipitation and anion-exchange chromatography, and prior to elution with competing PSP94. Lane C represents the competition control. Lane D represents the affinity matrix after elution with excess PSP94. Lane E represents the final eluted and concentrated (substantially) pure PSP94-binding protein.

FIG. 7 is a picture of a SDS-PAGE (7.5%) performed in non-reducing conditions. Lane A is the molecular weight marker (Kaleidoscope prestained standards, Bio-Rad). Lane B represents a PSP94-affinity matrix after incubation with a PSP94-binding protein purified by ammonium sulfate precipitation and anion-exchange chromatography, and prior to elution with competing (i.e., excess) PSP94 (i.e., free-PSP94). Lane C represents the competition control. Lane D represents the affinity matrix after elution with excess PSP94. Lane E represents the final eluted and concentrated (substantially) pure PSP94-binding protein. Results obtained indicate that affinity chromatography increase the purity of a PSP94-binding protein(s) in a significant manner.

Figure 8:
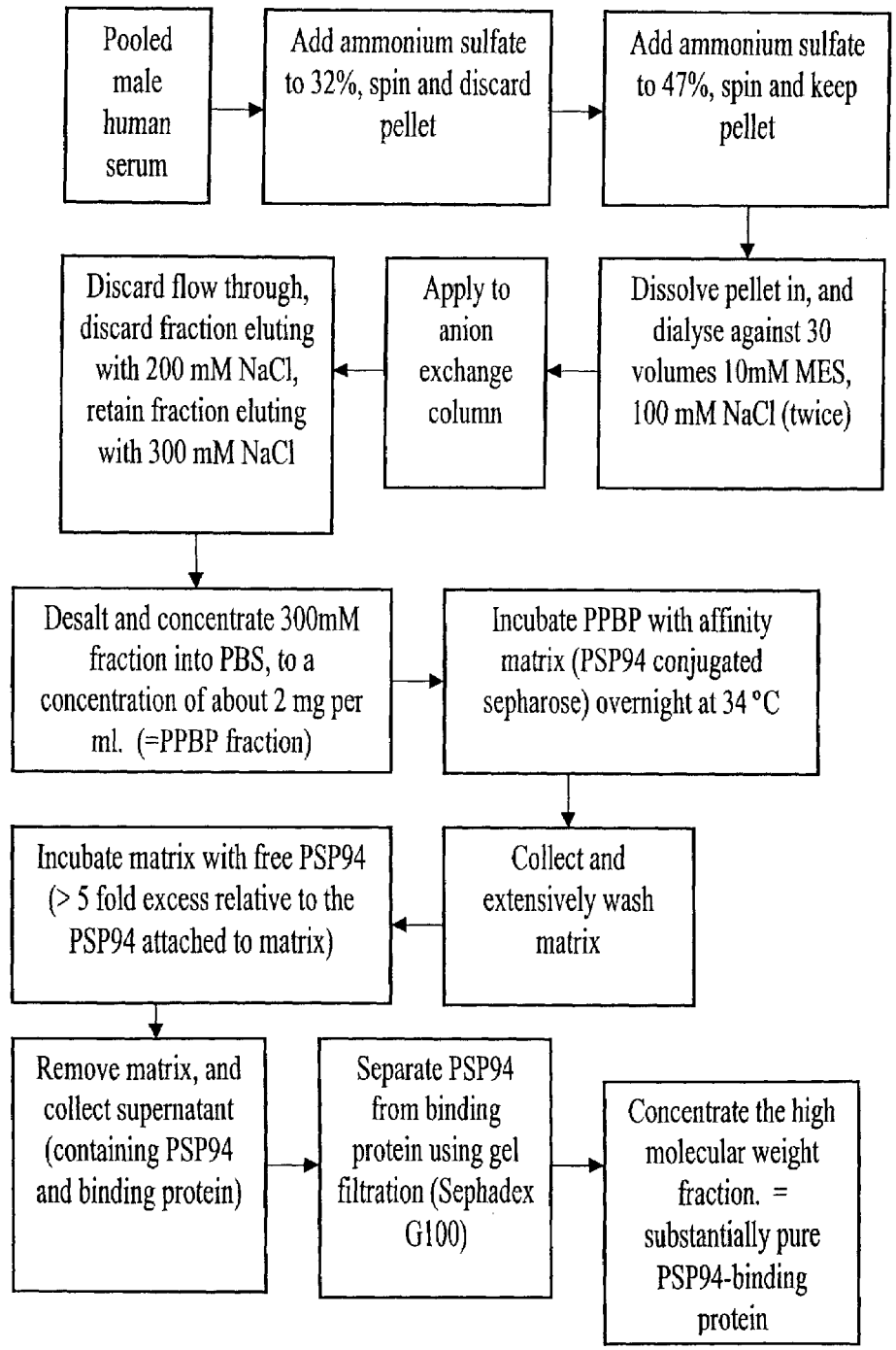
FIG. 8 is a schematic of a proposed purification process for the PSP94-binding protein.

The purification process of a PSP94-binding protein has been summarized in FIG. 8.

EXAMPLE 8

PSP94-Binding Protein Amino-Terminal Amino Acid Sequencing

A SDS-PAGE gel was prepared as described in example 5. However the proteins were transferred to sequencing grade PVDF membranes (ProBlott membranes, Applied Biosystem) using a Mini Trans-Blot transfer cell (Bio-Rad) according to the manufacturer's recommendations for sequencing preparation. This membrane was stained with Coomassie Brilliant blue, and analyzed by amino-terminal (i.e., N-terminal) amino acid sequencing. The amino-terminal amino acid sequencing was carried out for bands B, C and D illustrated in FIG. 4.

TABLE 7

| Band | Amino acid Sequence |
|---|---|
| B | (L)TDE(E)KRLMVELHN |
|   | (Corresponding to residues 28-41 of SEQ ID NO.:2) |
| C | Ubiquitous immunoglobulin sequence |
| D | LTDEEKRLMVELHNLYRAQVSPTASDMLHM |
|   | (Corresponding to residues 28-57 of SEQ ID NO.:2) |

As seen in table 7 bands B and D have the same N-terminal amino acid sequences, so these are likely to be different forms of the same protein, with B possibly representing some form of aggregate (multi-mere), or alternatively, B and D being alternatively spliced, or processed.

EXAMPLE 9

Cloning of a PSP94-Binding Protein Gene Sequences

Total RNA was isolated from 2×10$^6$ Jurkat clone E6-1 cells (TIB 152, American Type Culture Collection, Manassas, Va.) or from healthy blood donor peripheral blood mononuclear cells using Tri-reagent (Molecular Research Center Inc., Cincinnati, Ohio). RNA was ethanol-precipitated and resuspended in water. RNA was reverse transcribed into cDNA using the Thermoscript RT-PCR System (Life Technologies, Rockville, Md.). The cDNA was subsequently amplified by polymerase chain reaction (PCR) using Platinum Taq DNA Polymerase High Fidelity (Life Technologies) using a 5'-primer (5'-ATGCACGGCTCCTGCAGTTTCCTGAT-GCTT-3') and a 3'-primer (5'-GCCCACGCGTCGACTAG-TAC(T)$_{17}$-3')(Life Technologies 3' Race adapter primer, Life Technologies). The 5'-primer DNA sequence was based on PSP94-binding protein amino acid sequence and partial cDNA sequence published in Gene Bank database (National Institute of Health, U.S.A.) G.B. Accession No. AA311654 (EST182514 Jurkat T-cells VI *Homo sapiens* cDNA 5' mRNA sequence). Amplified DNA was resolved by agarose gel electrophoresis, excised from the gel and concentrated using Qiagen II DNA extraction kit (Qiagen, Mississauga, ON, Canada). Purified DNA was ligated into pCR2.1 plasmid (Invitrogen, Carlsbad, Calif.) and used to transform *E. coli*, strain TOP10 (Invitrogen). Ampicillin-resistant colonies were screened for cDNA-positive inserts by restriction enzyme analysis and DNA sequence analysis.

Blasting of DNA sequence of PSP94-binding protein into Gene Bank has identified some DNA sequence of unknown utility such as, for example, Gene Bank accession numbers XM 094933 (PRI Feb. 6, 2002), BC022399 (PRI Feb. 4, 2002), NM 153370 (PRI Apr. 7, 2003), BC035634 (PRI Sep. 23, 2002), etc.

EXAMPLE 10

Tissue Expression of PSP94-Binding Protein Messenger RNA

A PSP94-binding protein messenger RNA (mRNA) was isolated and the size and relative expression level in human tissues was determined by Northern blot. Commercial Northern blots containing 1 or 2 micrograms of human tissue poly-A RNA per lane (Multiple Tissue Northern (MTN™) Blot, Clontech, Palo Alto, Calif.) were hybridized as per the manufacture's recommendations with a [$^{32}$P]-labeled PSP94-binding Protein cDNA probe which spanned PSP94-binding Protein cDNA sequences 346 to 745. The intensity of the band was quantified with an alpha imager 2000, model 22595. The relative intensity of the band was determined and given an arbitrary score ranging from + to +++. This scoring was based on the lowest detectable 2.0 kb signal band seen.

Figure 9A:
FIG. 9a is a picture of a Northern blot performed on samples of human tissue poly-A RNA. Lane 1 represents brain RNA, lane 2 represents heart RNA, lane 3 represents skeletal muscle RNA, lane 4 represents colon RNA, lane 5 represents thymus RNA, lane 6 represents spleen RNA, lane 7 represents kidney RNA, lane 8 represents liver RNA, lane 9 represents small intestine RNA, lane 10 represents placenta RNA, lane 11 represents lung RNA and lane 12 represents peripheral blood lymphocytes (PBL) RNA.
Figure 9B:
FIG. 9b is a picture of a Northern blot performed on samples of human tissue poly-A RNA. Lane 1 represents spleen RNA, lane 2 represents thymus RNA, lane 3 represents prostate RNA, lane 4 represents testis RNA, lane 5 represents ovary RNA, lane 6 represents small intestine RNA, lane 7 represents colon RNA and lane 8 represents peripheral Blood Lymphocytes (PBL) RNA.
Figure 10:
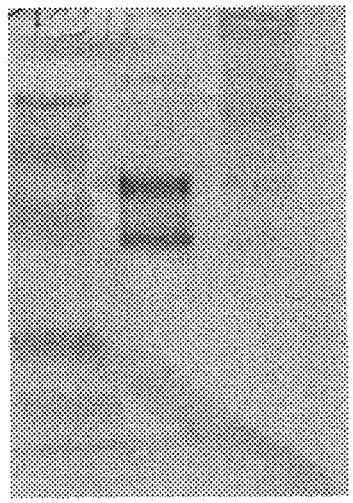
FIG. 10 is a picture of a Western blot showing recognition (binding) of PSP94-binding protein with a specific monoclonal antibody (1B11). Lane 1 is molecular weight markers (from top to bottom, 212, 132, 86, 44 kDa). Lane 2 is 0.2 μg of (substantially) purified PSP94-binding protein and lane 3 is 25 μl of partially pure PSP94-binding protein.

Quantification of the results illustrated in FIGS. 9a and 9b are summarized in tables 8 and 9 respectively. Briefly, RNA from brain, heart, skeletal muscle, colon, thymus, spleen, kidney, liver, small intestine, placenta, lung, prostate, testis, ovary, and peripheral blood lymphocytes (PBL) was analyzed for the expression of a PSP94-binding protein RNA expression.

TABLE 8

| Tissue | RNA signal (+) size kb | Relative intensity |
| --- | --- | --- |
| Brain | 0 | |
| Heart | +2.0 | +++ |
| Skeletal muscle | +2.0 | ++ |
| Colon | +2.0 | + |
| Thymus | +2.0 | + |
| Spleen | | |
| Kidney | | |
| Liver | | |

TABLE 8-continued

| Tissue | RNA signal (+) size kb | Relative intensity |
| --- | --- | --- |
| Small intestine | +2.0 | + |
| Placenta | | |
| Lung | | |
| Liver | | |

TABLE 9

| Tissue | RNA signal (+) and size kb | Relative intensity |
| --- | --- | --- |
| Spleen | | |
| Thymus | | |
| Prostate | +2.0 | +++ |
| Testis | +2.0 and 2.5 | ++ |
| Ovary | +2.0 | ++ |
| Small intestine | +2.0 | +++ |
| Colon | +2.0 | + |
| PBL | | |

EXAMPLE 11

Generation of Polyclonal Antibodies and Monoclonal Antibodies for Free PSP94, Bound PSP94 and PSP94-Binding Protein Antibody Generation The immunization scheme described herein was developed to promote the production of antibodies to PSP binding protein, or to PSP94. Anti-PSP94 antibodies such as, antibodies which bind to an epitope of PSP94 that is exposed when PSP94 is in a bound form (e.g., bound to a PSP94-binding protein), antibodies which bind to an epitope of PSP94 that is available only when PSP94 is in a free form (free of PSP binding protein) or antibodies which bind both the free and bound forms of PSP94.

Monoclonal Antibodies

Four Balb/c mice (identified a, b, c and d) were immunized subcutaneously with 15 micrograms each of a (substantially) pure PSP94-binding protein (i.e., this preparation also contains PSP94) preparation in TiterMax™ adjuvant. Twenty-one days later, all mice were given a second boost and after a further 8 days, the mouse serum was tested for reactivity for both PSP94 and PSP94-binding protein in the ELISA screening assay described above. Since the purification of a PSP94-binding protein involves saturating all the binding sites with PSP94, the sera of the animals immunized with the substantially pure PSP94-binding protein preparation, had also the possibility of being tested positive for both antigens.

Mice a and b were boosted intra-peritoneally with a further 15 μg of a PSP94-binding protein with no adjuvant. The remaining two mice (c and d) were boosted subcutaneously with a further 15 μg of a PSP94-binding protein together with 15 μg of native PSP94 in Titer Max™ adjuvant in order to increase the likelihood of obtaining antibodies to exposed epitopes of PSP94.

After a further 4 days, the spleens of mice a and b were harvested, the B lymphocytes collected, and fused with NSO myeloma cells in order to generate hybridomas (Galfre G. and Milstein C, Meth. Enzymol. 73:3-46, 1981). A hundred thousand splenocytes, in Iscove's MDM selection medium (supplemented with 20% FBS, HAT, 10 ng per ml interleukine-6, and antibiotics), were plated into each well of 96 well plates. Since antibodies are secreted from the cells, cell culture media (i.e., supernatant) may be harvested for characterization of the antibodies produced. After 10 days of incubation at 37° C., the supernatants of wells containing clones were assessed by an ELISA screening assay (see bellow). Clones producing antibodies showing a positive recognition (binding) of the PSP94 or PSP94-binding protein plates and free of unspecific binding to PBS coated plate, were selected for further investigation and characterization.

Desired (positive) hybridoma clones were plated into 6 well plates. The supernatants were re-tested for the presence of the specific antibody, and those of the clones remaining positive were passed through successive cycles of cloning by limiting dilution. Cloning in such a manner to ensure that the hybridoma cell line produced is stable and pure. Typically, two cycles of cloning were necessary to achieve this goal. Multiple vials of frozen stocks were prepared, with one vial from each batch tested for viability and antibody production. Results of clone characterization are illustrated in table 10.

Alternatively, for the generation of anti-PSP94 antibodies, mice are immunized with a PSP94 preparation (substantially pure PSP94) in TiterMax™ adjuvant. Boosting and hybridoma procedures are performed as described above.

Therefore, antibodies which bind to an epitope of PSP94 that is exposed when PSP94 is in a bound form are produced using the immunization schemes described above. The binding specificity of the antibody is determined in an ELISA assay or in a Western blot assay by contacting the desired antibody which is conjugated with a reporter molecule with a complex formed by PSP94 and a PSP94-binding protein. When the antibody binds to the complex, a positive reaction arises upon detection of the signal generated by the reporter molecule.

Antibodies which bind to an epitope of PSP94 that is available only when PSP94 is in a free form (free of a PSP binding protein) are also produced using the immunization schemes described above. The binding specificity of the antibody is determined in an ELISA assay or in a Western blot by contacting the desired antibody which is conjugated with a reporter molecule with a substantially purified PSP94 and in a parallel experiment by contacting the antibody with a complex formed by PSP94 and a PSP94-binding protein. An antibody (e.g., conjugated with a reporter molecule) which binds to an epitope of PSP94 that is available only when PSP94 is in a free form will produce a positive reaction when contacted with a substantially purified PSP94 and a negative reaction (i.e., no signal (color) is detected) when contacted with the complex.

Antibodies which bind both the free and bound forms of PSP94 (total PSP94) are also produced using the immunization schemes described above. However an antibody which binds both the free and bound forms of PSP94 will produce a positive reaction when contacted with a substantially purified PSP94 and will also produce a positive reaction when contacted with the complex formed by PSP94 and a PSP94-binding protein.

Hybridomas producing a desired antibody are isolated, expanded and stored as described above.

Monoclonal Antibody Purification.

Mouse IgG1 monoclonal antibodies were purified using a high salt protein A procedure as detailed in Antibodies: A Laboratory Manual eds Harlow and Lane, Cold Spring Harbor Laboratory (for reference see above).

Monoclonal Antibody Isotyping

Isotyping was performed using a Mouse Monoclonal Antibody Isotyping Kit (Roche Diagnostics Corporation Indianapolis USA). This kit provides information relating to the class (IgG, IgA or IgM) the type of light chain (kappa or lambda) and IgG subtype (IgG1, IgG2a, IgG2b or IgG3). The antibodies tested were mainly of the IgG1 kappa subtype. However, one antibody was shown to be of the IgM kappa subtype (B26B10).

Polyclonal Antibodies

The polyclonal antibody to PSP94 of the present invention was produced by immunizing New Zealand white rabbits. Each rabbit was immunized with 50 micrograms of purified human PSP94 (>95% purity) in Freunds complete adjuvant. 3 weeks later the rabbits were boosted with a further 50 micrograms of PSP94. After a further 4 weeks, the rabbits were bled every week for a period of 12 weeks (25 ml bleed each week). The serum was separated from the whole blood and affinity purified antibodies were purified from the IgG fraction as described below.

First Step: Purification of IgG Fraction Using Protein A 1.5 g of Protein A immobilized on Sepharose CL-4B obtained from Sigma (Cat no. P-3391) was swelled and washed in 20 volumes of PBS (0.14 m NaCl, 10 mM sodium Phosphate, pH 7.4). Once the sepharose was swelled, two additional aliquots of PBS were used to wash the matrix twice. The total volume of swelled matrix was about 5 ml which correspond to a capacity of binding of at least 50 mg of rabbit IgG.

Twenty-five milliliters of rabbit serum was diluted with an equal volume of PBS and filtered through a 0.22 micron filter. Five milliliters of protein A slurry were added to this mixture and the mixture was agitated on a rocker for 1 hour at room temperature. The suspension was then poured into a 20 ml disposable plastic chromatography column, and the flow through discarded. The column was washed with PBS and the O.D. (or OD; optical density) of the flow through monitored periodically at 280 nM until it was stabilized to less than 0.1.

0.1 M glycine at pH 3.0 was carefully applied to the matrix and 1 ml fractions were collected directly into 100 microlitres of 1.0 M Tris pH 8.0. The IgG eluted within 10 ml. Any tightly bound proteins were then eluted and discarded with 0.1 M Glycine pH 2.0, and the column was re-equilibrated with PBS. The OD280 of the collected fractions was measured, and the fractions containing the majority of the IgG were pooled. The yield was about 40-50 mg of IgG from an initial starting volume of 25 ml of rabbit serum (an OD280 of 1.4 for a 1 mg/ml solution). The IgG fraction were either stored at 4° C. with 0.05% azide for short term storage (about 1 week) or frozen for long term storage.

Step 2: Affinity Purification of Anti-PSP94 IgG on PSP94 Affinity Column.

Step 2 A: Matrix Preparation

A first step in purification of an anti-PSP94-specific IgG antibody was to produce an affinity purification matrix. It was found that a good efficiency may be achieved using a column with about 1 mg of PSP94 per milliliter of matrix. This protocol produces about a 5 ml column with 5 mg of conjugated PSP94.

Seven milligrams of PSP94 were prepared in 5 ml of 200 mM sodium bicarbonate buffer (about pH 8, no need for pH adjustment). The OD 280 of this solution was about 2.24.

Two grams of cyanogen bromide activated sepharose (Sigma) was weighted and swelled for 3×10 minutes in 100 ml of ice cold 1 mM HCl to remove stabilizers. The matrix was kept in suspension during the process, and the buffer was changed either by cold rapid filtration or cold centrifugation.

Finally, the sepharose was washed with 100 ml of ice cold water. The matrix was pelleted and excess water removed.

The OD of the cold PSP94 solution was first measured and the solution was added to 5 ml of the cold matrix, and mixed. After 1 minute, 1 ml of slurry was removed and spined for 10 seconds in a microfuge. The supernatant was removed and the OD 280 was measured. The removed slurry and antibody solution was replaced to the conjugation mixture. The reaction was continued until the OD measurement indicated that between about 70 and 80% of the PSP94 has been removed from the solution. The reaction was stopped by adding 10 ml of 0.1 m Glycine in 100 mM sodium bicarbonate. The mixture was incubated for 30 minutes at about 4° C. Exemplary results of conjugation of PSP94 to the sepharose matrix are illustrated in Table B.

TABLE B

Progress of PSP94 conjugation to sepharose

| Time (min.) | OD280 of solution | Volume (ml) | A units on (mg) | A units off (mg) | Conjugation efficiency |
|---|---|---|---|---|---|
| 0 | 2.24 | 5 | 0.0 (0.0) | 11.2 (7.0) | 0% |
| 1 | 0.96 | 10 | 1.6 (1.0) | 9.6 (6.0) | 14% |
| 2 | 0.63 | 10 | 4.9 (3.1) | 6.3 (3.9) | 44% |
| 5 | 0.35 | 10 | 8.3 (4.8) | 3.5 (2.2) | 69% |
| Stop | 0.16 | 20 | 8.6 (5.0) | 3.2 (2.0) | 71% |

Since 71% of the PSP94 has been removed from the solution, it is assumed that the 71% is attached to the matrix. To condition the matrix and to remove any loosely bound PSP94 a series of high salt washes at low and high pH was performed. A disposable 20 ml column was packed with the PSP94 affinity matrix, and washed through 3 cycles of 10 ml volumes of 0.1 M sodium bicarbonate, 0.5 M NaCl, followed by 0.1 M glycine, 0.5 M NaCl, pH 2.5. A peristaltic pump at a flow rate of about 2 ml per minute may be used. Finally the column was equilibrated in PBS containing 0.05% $NaN_3$ and stored at 4° C.

Step 2 B: Affinity Purification of PSP94 Specific IgG.

The protein A purified IgG was at a concentration of about 5-10 mg per ml in 0.1 M glycine, 100 mM Tris at neutral pH. This solution was diluted in PBS to a concentration of 1 mg per ml, (OD 280 of 1.4). This buffer composition was adequate for the affinity purification.

A hundred and fifty milliliters of protein A purified IgG (1 mg/ml) were applied to the 5 ml PSP affinity column at a flow rate of 2.5 ml per minute. The OD 280 of the flow through was monitored and was kept to provide a reduction of about 30% (OD 280 of about 1.0). The reduction in OD indicates that specific antibodies are binding to the column. When the OD of the flow through approaches the OD of the solution being applied, then the column is saturated. If the OD of the eluant is the same as the solution being applied from the start, the column is inactive, or the protein A purified IgG has no PSP94 specific antibodies in it.

Once all the protein A purified IgG had flowed through the column, the column was whashed with PBS until the OD 280 stabilizes (less than 0.05). The antibody was eluted with 0.1 M glycine, pH 2.5 and 1 ml aliquots were collected directly into eppendorf tubes containing 150 microlitres of 1 M TRIS, pH 8.0. Ten fractions were collected and the column was equilibrated with PBS containing 0.05% $NaN_3$. The OD280 of the eluant was measured and the major fractions were pooled. Three milliliters aliquots were desalted using a PD10 desalting column (BioRad) equilibrated with PBS. The concentration of antibody was estimated using OD280 (1 mg/ml=1.40) and aliquots were stored at −80° C. The yield was about 25 mg of polyclonal anti-PSP94 IgG antibody.

EXAMPLE 12

Antibody Characterization

ELISA-Based Hybridoma Screening Assay

In order to evaluate the titer and the specificity of the antibodies produced from mice or from the hybridoma generated from mouse B cells, an ELISA screening assay was developed.

Briefly, microtitre plates (Nunc, MaxiSorp) were coated with 100 µl aliquots of either native PSP94 (isolated from human seminal plasma; 5 µg/ml in 0.1 M sodium carbonate pH 9.6) or with a PSP94-binding protein (0.1 µg/ml in 0.1 M $NaHCO_3$) or phosphate buffered saline (PBS; 140 mM NaCl 10 mM sodium phosphate pH 7.5) overnight at 4° C. Plates were blocked for 1 hour with a solution of 1% bovine serum albumin (BSA) in phosphate buffered saline at 34° C. (BSA allows the saturation of the binding sites and limit unspecific binding to the plates). The plates (wells) were then washed in PBS containing 0.1% polyoxyethyylene-sorbitan monolaurate (PBS-Tween), prior to application of the mouse serum samples, or hybridoma supernatants diluted in 0.5% BSA. The plates were incubated for 1 hour at 34° C. prior to application of a 1:1000 dilution in PBS 0.5% BSA of peroxidase conjugated polyclonal rabbit immunoglobulins recognizing mouse immunoglobulins. (rabbit anti-mouse IgG peroxidase). After a further 1 hour incubation at 34° C. the plates were extensively washed in PBS Tween, prior to development of the peroxidase signal in 3,3',5,5'-Tetramethylbenzidine (TMB). After 30 minutes the optical density at 630 nm was read in a micro plate reader.

Antibody Biotinylation

The diluent (buffer) of the purified antibody was exchanged for 0.1 M $NaHCO_3$ buffer pH 8.0 and the protein concentration was adjusted to 1 mg/ml. A 2 mg/ml solution of biotinamidocaproate N-hydroxysuccinimide ester was prepared in DMSO and an appropriate volume of this solution was added to the antibody to give either a 5, 10 or 20 fold excess of biotinylating agent. The solution was incubated on ice for 2 hours with occasional agitation before an equal volume of 0.2 M glycine in 0.1 M $NaHCO_3$ was added to give a final concentration of 0.1 M glycine.

After one further hour incubation on ice, the antibody was separated from the free biotinylating agent by gel filtration using a PD10 gel filtration column (Biorad). Biotinylated antibodies were stored at 4° C. in with 0.05% sodium azide added as preservative. The optimal extent of biotinylation and optimal usage concentration of the biotinylated antibodies was determined on antigen-coated plates.

Relative Epitope Analysis

ELISA plates were coated either with a PSP94-binding protein or PSP94 and blocked as described above. Appropriate concentrations of the biotinylated antibodies prepared as described above were incubated with the coated plates in the presence or absence of a 50-fold excess of a panel of unlabelled antibodies. Competition with the unlabelled antibodies indicates epitopes that are shared between the two antibodies. Detection is performed using streptavidin peroxidase.

Lack of competition indicates independent epitopes. Results of epitope analysis are illustrated in table 10.

TABLE 10

| Clone | Specificity | Class and subclass | Epitope shared with | ATCC Patent Depository No. |
|---|---|---|---|---|
| 2B10 | Binding protein | IgG$_1$κ | 9B6, 3F4 | — |
| 1B11 | Binding protein | IgG$_1$κ | Unique | — |
| 9B6 | Binding protein | IgG$_1$κ | 2B10, 3F4 | — |
| 17G9 | Binding protein | IgG$_1$κ | Unique | PTA-4243 |
| 3F4 | Binding protein | IgG$_1$κ | 2B10, 9B6 | PTA-4242 |
| P8C2 | Binding protein | IgG$_1$κ | Unique | — |
| B3D1 | Binding protein | IgG$_1$κ | — | — |
| 26B10 | Binding protein | IgMκ | — | — |
| 2D3 | Free PSP94 | IgG$_1$κ | Unique | PTA-4240 |
| P1E8 | Free and bound (total) PSP94 | IgG$_1$κ | Unique | PTA-4241 |
| 12C3 | Free PSP94 | IgG$_1$κ | Unique | — |
| 1A6 | Free PSP94 | IgG$_1$κ | | PTA-6599* |

*PTA-6599 was deposited to the ATCC on Feb. 23, 2005

Antibody Conjugation

Kits using antibodies conjugated with a reporter molecule were developed. Antibodies listed in table 10 were conjugated with a reporter molecule using the following procedures.

Horse radish peroxidase (3 mg) (HRP) was diluted into 0.6 ml of deionized water. 0.2 ml of sodium periodate 0.01 M in PBS pH 7.5 was added to the diluted HRP and the mixture was incubated for 25 minutes at room temperature. Dialysis was carried out against sodium acetate solution (1 mM pH 4.0) at 4° C. Buffer changes (3 times) were effected at each two hours.

For example, five milligrams of protein-A purified and lyophilized 1A6 antibody was diluted with 50 μl of carbonate buffer (0.2M, pH 9.5). The dialyzed HRP mixture was added to the antibody mixture. 0.2 ml of the same carbonate buffer was added. Reaction was allowed to proceed for 2 hours at room temperature with agitation. 0.1 ml of sodium borohydrate (4 mg/ml in deionized water) was added and incubation was perfomed for 2 hours at 4° C. with agitation.

The mixture was transferred in a conical tube and 1.2 ml of ammonium sulfate saturated solution (300 g of (NH$_4$)$_2$ SO$_4$ in 400 ml of deionized water) was added and was left for 1 hour at 4° C. with agitation. The precipitated solution was centrifuged at 300 RPM for 20 minutes. The pellet was resuspended in the ammonium sulfate saturated solution. Centrifugation was again performed as described above. The pellet was then resuspended in 2 ml of PBS (0.01M pH 7.1). Dyalisis was performed against 0.01M PBS pH 7.4. The buffer was changed every 2 hours with fresh 0.01M PBS pH 7.4 (4 buffer changes). HRP conjugated antibody was diluted in a stabilizing solution (50% fetal bovine serum in Tris-HCl (31.52 g/L in deionized water), pH 6.8) and was used at a concentration of between 1.5 to 10 mg/ml in the assays, methods and kits of the present invention.

Preparation of PSP94 Master Solution Standard

A PSP94 master solution standard was prepared and lyophylized in bovine serum albumin/mannitol stabilization buffer (5 micrograms of PSP94 in 4 mg/ml mannitol, 2% BSA (fraction v) in 10 mM sodium phosphate, 20 mM EDTA, 40 micrograms per ml Thimerosal pH 7.5 in 0.5 ml). For this purpose PSP94 was purchased from US Biologicals and quantified using ultraviolet absorbance (1 mg/ml at 280 nm=1.53). Multiple vials of the master solution were stored at −20° C. and this material was used to calibrate the standard curves used in each batch of ELISA kits. Several dilution of the standard for use within the kits was prepared as indicated below.

Specificity of PSP94 Antibodies for Free or Total PSP94

In order to further characterize the specificity of the antibodies generated herein, an assay was developed to determine if the monoclonal antibodies recognize PSP94 in its free form and/or when it is bound to a PSP94-binding protein.

In order to promote the formation of a PSP94/PSP94-binding protein complex, the two (substantially or partially) purified proteins were pre-incubated together. Briefly, a partially pure PSP94-binding protein preparation (see example 4), at a concentration of 1 mg/ml (total protein concentration) in PBS containing 0.5% BSA was pre-incubated for 1 hour at 34° C. with or without 5 μg/ml of native PSP94.

An ELISA plate (96 well plate) was coated with 17G9 monoclonal antibody at a concentration of 2 μg/ml (in 0.1M NaHCO$_3$ pH 8.0) by an overnight incubation at 4° C. As described herein, this antibody recognizes a PSP94-binding protein. Wells of the plate were subsequently blocked with 1% BSA for 1 hour at 34° C. The PSP94/PSP94-binding protein complex generated above was incubated with the 17G9 coated plates for 1 hour at 34° C. before washing off any unbound material. The plates were then incubated with biotinylated PSP94-specific antibodies (2 μg/ml in PBS 0.5% BSA). Any positive binding of these antibodies would indicate that the PSP94 epitope that is recognized is exposed (available) even when bound to a PSP94-binding protein. These results are illustrated in table 10. Binding of the biotinylated PSP94-specific antibodies to the bound PSP94 was visualized with a streptavidin peroxidase system and developed with TMB giving a blue color.

Figure 11:
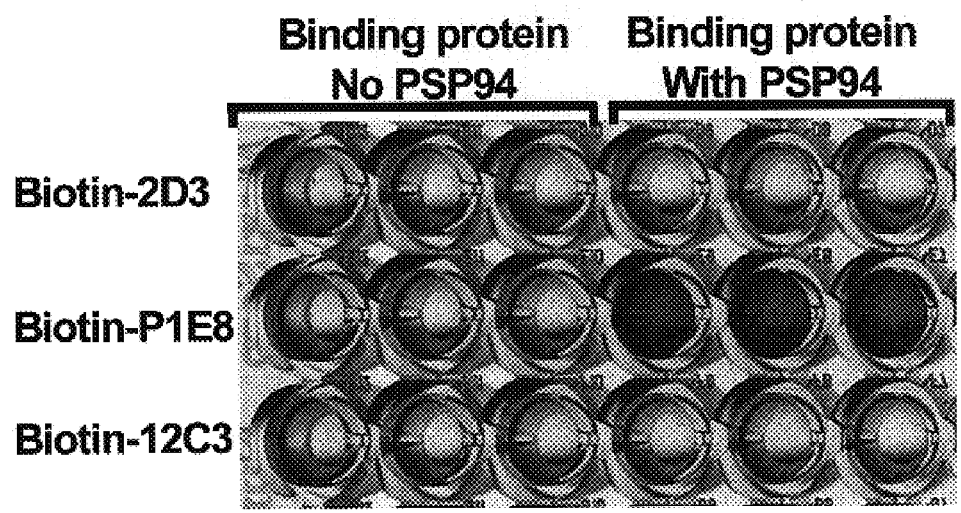
FIG. 11 is a picture of an ELISA plate where the specificity of monoclonal antibodies for bound and free forms of PSP94 is evaluated. Colored wells represent a positive result.

Results illustrated in FIG. 11 indicate that none of the antibodies tested react with captured PSP94-binding protein when the binding sites are not saturated with PSP94. When the binding sites are saturated with PSP94, P1E8 shows strong reactivity towards the complex. However, 2D3 and 12C3 do not. Thus, P1E8 recognize bound and free PSP94 and the other two antibodies (2D3 and 12C3) only recognize the free form of the protein. Antibodies 2D3 and 12C3 probably recognize a PSP94 epitope that is masked when it is bound to a PSP94-binding protein. Each of these antibodies detects native and recombinant PSP94 when coated onto ELISA plates. All three antibodies function as capture or detector antibodies in sandwich ELISA formats to produce a linear standard curve over a useful range of concentrations of PSP94. However, 12C3 appears to be of lower affinity than 2D3 or P1E8 toward PSP94.

The utility of these antibodies to detect PSP94 was illustrated in the following assay; an ELISA plate was coated with 5 μg/ml of PSP94 in pH 9.6 carbonate buffer and incubated overnight at 4° C. The plate was blocked with 1% BSA for 1 h at 34° C. Samples were then incubated in the plate overnight at 4° C. Biotinylated P1E8 was applied at 1 microgram/ml for 2 hrs at 34° C. and peroxidase streptavidin was applied for 1 h at 34° C. before development in TMB. The lower limit of quantification (LLQ) was shown to be in the range of 1 ng/ml. It is of particular interest that the assay (e.g., standard curve) may be performed with native PSP94 (i.e., PSP94 isolated from human serum) or recombinant PSP94.

Western Blots

Some antibodies described herein were assessed by Western blot. Briefly, 0.2 micrograms of (substantially) purified PSP94-binding protein, or 25 microliters of partially pure PSP94-binding protein were run on 7.5% SDS PAGE gels under non-reducing conditions. The proteins were transferred to PVDF membranes, the membranes were blocked with 1% BSA, probed with the hybridoma supernatants at a dilution of 1:5 (in PBS/0.5% BSA), and the bound antibody was detected with an anti-mouse immunoglobulin peroxidase-conjugate raised in rabbit. The signal was developed in 0.05% diaminobenzidine 0.01% hydrogen peroxide.

EXAMPLE 13

Free PSP94 Immunodetection Assays

The PSP94 antibodies described above (2D3 (PTA-4240), P1E8 (PTA-4241), 12C3, polyclonal and 1A6 (PTA-6599)), may be used in a competitive ELISA assays e.g., coating plates with PSP94 (or sample), and using the PSP94 within the sample to inhibit the binding of the antibody to the PSP94 coated plates. These antibodies may also be used in standard ELISA assays where an antibody is coated to the plate and a sample containing PSP94 is added. Specific detection of the complex is subsequently performed with a second antibody able to bind to PSP94 (the first and second antibodies binding to a different epitope of PSP94).

Figure 12A:
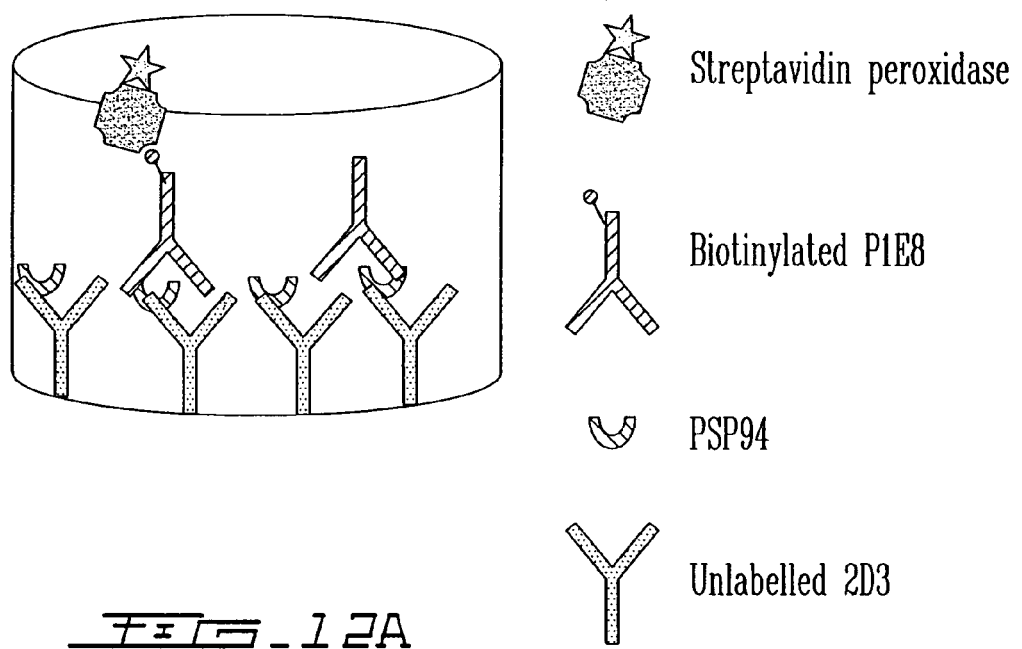
FIG. 12A is a schematic of a method used to measure the amount of free PSP94.
Figure 12B:
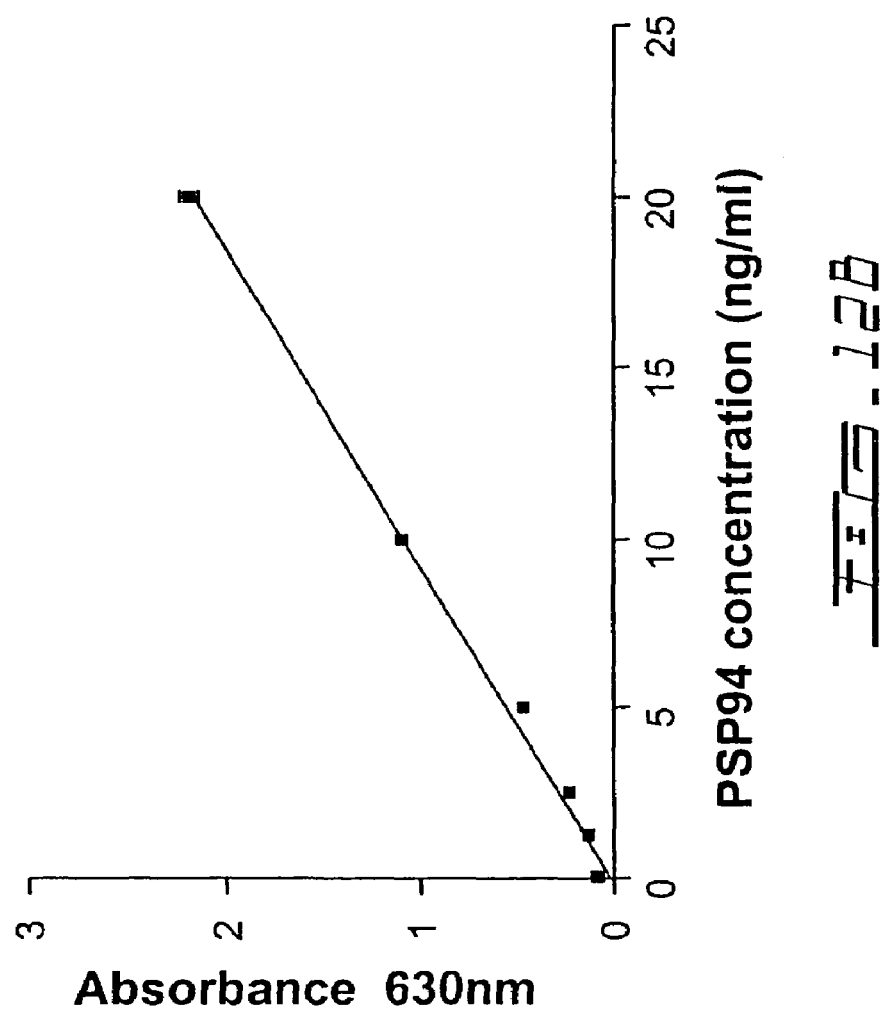
Figure 12D:
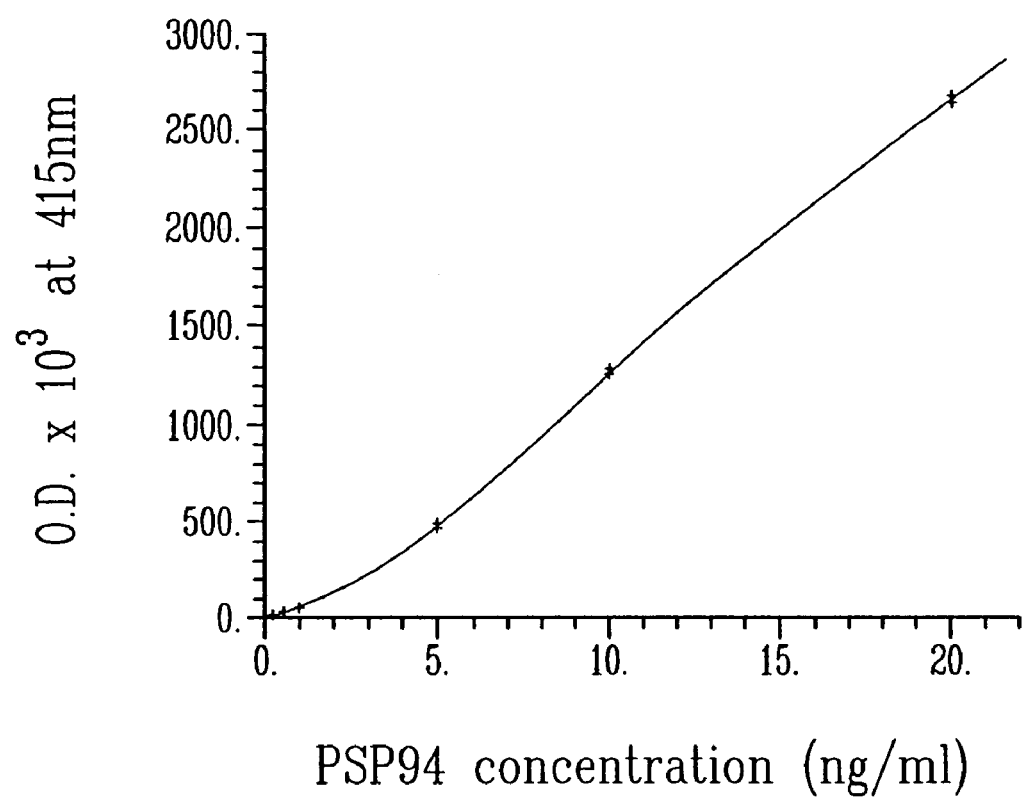
FIG. 12D is a graph illustrating the results of a sandwich ELISA assay for measuring free PSP94.

In a first experiment, the use of 2D3 in a competitive ELISA format was investigated. As illustrated in FIG. 12a, the plates were coated with the 2D3 antibody and samples containing PSP94 was added. The complex was detected with a biotynylated P1E8 (which recognizes a different epitope of PSP94). Detection is performed by adding streptavidin coupled with peroxidase and subsequently adding the perosidase's substrate. FIG. 12b represent results of an ELISA assay using the method illustrated in FIG. 12a.

In order to limit the possible dissociation (e.g., promoted by 2D3) of the PSP94/PSP94-binding protein complex during the ELISA assay, improvements were introduced. Briefly, the improved assay involves pre-absorption (removal) of the PSP94/PSP94-binding protein complex with a PSP94-binding protein antibody described herein before performing the assay. The PSP94-binding protein antibodies selectively remove PSP94-binding protein and the PSP94/PSP94-binding protein complex (i.e., bound PSP94). This is done without upsetting the kinetics of the equilibrium reaction between a PSP94-binding protein and PSP94. Pre-absorption can be done with, for example the 17G9 linked to a sepharose matrix, giving then a sample that is free of the complex (unbound PSP94 remains). The sample is then processed as described above (i.e., incubating the complex-free sample with the plate coated with 2D3 and detecting with biotinylated P1E8, streptavidin peroxidase and peroxidase's substrate.

Another standard immunodetection assay (a sandwich ELISA assay measuring free PSP94) was performed. Briefly, wells of an ELISA plate were coated with 150 microlitres of an anti-PSP94 polyclonal antibody (which has been generated as described herein) at 3 µg/mL in $KPO_4$ 0.1M, Glutaraldehyde 0.001% at a pH of 6.5. The antibody is allowed to bind to the plates for 24 hours at room temperature and rinsed with 300 microlitres of deionized water. After washing, the wells were coated with 200 microlitres of 10 mM sodium phosphate, 140 mM NaCl, pH 7.5 with 0.5% BSA (fraction v) and 2% sucrose and incubated for 24 hours before aspiration of the solution. The plates were allowed to dry at room temperature overnight. The plates may be used right away or may be dried and stored for subsequent experiments.

Six PSP94 standards dilutions were prepared by diluting a master solution of PSP94 to obtain concentrations of 0, 1, 5, 10, 20, 40 ng/mL in a final volume of 0.5 mL of 10 mM sodium phosphate, 20 mM EDTA, 40 micrograms per ml Thimerosal, 0.25% BSA Twenty-five micro liters of serum samples containing PSP94 or PSP94 standards (the samples and standards were brought to room temperature, i.e., about 22° C.+/−2° C.) and added to independent wells. A hundred micro liters of the anti-free PSP94 antibody (1A6 (PTA-6599)) conjugated with horse-radish peroxidase was also added to each well. The plates were incubated for sixty minutes on a plate shaker (110+/−10 rpm) at room temperature (i.e., about 22° C.+/−2° C.). The well content was decanted by inverting the plates and excess liquid was absorbed by putting the inverted plate onto absorbing paper. The wells were then washed three times with 300 µL of washing solution. At the last wash, the plates were completely decanted by tapping them against absorbing paper until there was no trace of liquid remaining. A hundred microliters of the enzyme's substrate solution was added to each well and the reaction was allowed to proceed for 15 minutes on a plate shaker (110+/−10 rpm) at room temperature (i.e., about 22° C.+/−2° C.). Fifty microliters of stopping solution (0.5M sulfuric acid) was added to each well. When the enzyme's substrate (substrate-chromogen solution) is added, the enzyme catalyzes a reaction which produces a blue color. When the stopping solution is added, the color turns yellow. The intensity of the color is directly proportional to the concentration of PSP94 in the sample or standard. The intensity of the color was measured by reading the absorbance at 415 or 405 nm in a microplate reader (spectrophotometer) immediately after the assay was completed.

The quantity of free PSP94 in the sample was determined by making a plot of the optical density (on the ordinate) measured for the standards as a function of the concentration of standards (on the abscissa) and the corresponding concentration which gives the optical density measured for the sample was evaluated. Table 11 represents results obtained by measuring the concentration of PSP94 in 2 unknown human serum samples using the sandwich ELISA assay for measuring free PSP94 described above. These results are also illustrated as a graph in FIG. 12c.

TABLE 11

| WELLS | OPTICAL DENSITY at 415 nm | CONCENTRATION (ng/mL) |
| --- | --- | --- |
| 0 ng/mL | 0 | |
| 0.25 ng/mL | 0.013 | |
| 0.5 ng/mL | 0.025 | |
| 1 ng/mL | 0.049 | |
| 5 ng/mL | 0.475 | |
| 10 ng/mL | 1.261 | |
| 20 ng/mL | 2.665 | |
| Serum | 0.638 | 6.1 |
| Serum | 1.915 | 14.4 |

Several parameters of the sandwich ELISA assay for measuring free PSP94 described herein have also been measured in order to verify the assay performance.

Precision:

The precision of an analytical method describes the closeness of mean test results obtained by the method to the true value (concentration) of the analyte. Precision is determined by replicate analysis of samples containing a known amount of the analyte.

In duplicate, the standard curve and five times each of the three control levels are measured. For each level of controls the mean, the standard deviation and the coefficient of variation (in percent) are calculated. The within assay % coefficient of variation is preferably below 15%.

Calculation:

$$\% \text{ Coefficient of variation } (CV) = \frac{\text{Standard Deviation}}{\text{Mean}} \times 100$$

The intra-assay precision was determined for three (3) serum samples from the mean of 10 replicates each. Results are illustrated in Table 12 below.

TABLE 12

Intra-Assay

| Sample | N | Mean (ng/mL) | Standard Deviation (ng/mL) | Coefficient of variation (%) |
|---|---|---|---|---|
| 1 | 10 | 7.4 | 0.2 | 2.1 |
| 2 | 10 | 14.3 | 0.2 | 1.4 |
| 3 | 10 | 23.3 | 0.8 | 3.5 |

The inter-assay precision was determined for three (3) serum samples from the mean of 20 replicates. Results are illustrated in Table 13 below.

TABLE 13

Inter-Assay

| Sample | N | Mean (ng/mL) | Standard Deviation (ng/mL) | Coefficient of variation (%) |
|---|---|---|---|---|
| 1 | 20 | 7.7 | 0.4 | 4.8 |
| 2 | 20 | 14.6 | 1.4 | 2.5 |
| 3 | 20 | 24.0 | 1.0 | 4.1 |

Accuracy: or recovery study: known amounts of PSP94 were added to a human serum sample to determine recovery performance of the assay. The data obtained are indicated in Table 14 below.

TABLE 14

| Samples | Expected value (ng/mL) | Observed value (ng/mL) | % of recovery |
|---|---|---|---|
| 1 | 19.2 | 15.7 | 81.5 |
| 2 | 29.2 | 21.8 | 74.5 |
| 3 | 39.2 | 28.7 | 73.2 |

Linearity:

The linearity is the ability of a diluted patient sample to show proportional values when read through the working standard curve. Two serum samples were diluted and run.

The patient dilution calculation was done as follows: The standard curve and the patient dilution curve were calculated and drawn. The controls values were read against the reference curve. The theoretical and expected values were then compared. Results of the linearity experiment are illustrated in Table 15:

TABLE 15

| Parameters | Samples | |
|---|---|---|
|  | 1 | 2 |
| Undiluted | 14.9 | 11.7 |
| ½ | 7.0 | 6.0 |
| ¼ | 2.7 | 2.5 |
| ⅛ | 1.2 | 1.2 |

Specificity

The cross-reactivity studies were performed using substances which may potentially interfere with the performance of the assay. The results were as shown in the Table 16 below (ND=not detectable):

TABLE 16

| CROSS-REACTANT | CROSS-REACTIVITY |
|---|---|
| Prostate specific antigen (PSA) 10 μg/mL | ND |
| alpha feto protein (AFP) 10 μg/mL | ND |
| carcinoembryonic antigen (CEA) 10 μg/mL | ND |
| human chorionic gonadotrophin (HCG) 10 μg/mL | ND |
| PAP 1 μg/mL prostatic acid phosphatase | ND |
| LACTALBUMIN 10 mg/mL | ND |
| HEMOGLOBIN 500 mg/dL | ND |
| BILIRUBIN 20 mg/dL | ND |
| TRIGLYCERIDES 1000 mg/dL | ND |
| CYCLOPHOSPHAMIDE 800 μg/mL | ND |
| METHOTREXATE 50 μg/mL | ND |
| DOXORUBUCIN-HCL 20 μg/mL | ND |
| DIETHYSTILBESTROL 2 μg/mL | ND |
| FLUTAMIDE 10 μg/mL | ND |

Other parameters such as reproducibility, recovery, hook effect, matrix effect, etc. were all determined and results obtained indicated that the free PSP94 assay may be used successfully to determine the levels of PSP94 in human samples and especially of free PSP94 in human serum sample.

EXAMPLE 14

Total PSP94 Immunodetection Assays

Since the P1E8 antibody is able to recognize PSP94 both in its free and bound form, an assay to measure total PSP94 has been developed. For example, P1E8 is immobilized to the plate and a sample containing free PSP94 and PSP94 complexed with a PSP94-binding protein is added. The PSP94 and the complex remains bound to the antibody and an antibody having a different affinity (a different binding site on PSP94) than P1E8 may be added. An example of such an antibody is 2D3 or any other suitable PSP94-antibody. Detection is performed by using a label that may be conjugated to 2D3 or by a secondary molecules (antibody or protein) recognizing directly or indirectly (e.g., biotin/avidin or streptavidin system) the 2D3 antibody.

However, based on the observation that 2D3 might disturb the binding equilibrium between PSP94 and PSP94-binding protein, the assay to measure total PSP94 (bound and unbound) was improved.

Particularly, the assay was performed as illustrated in FIG. 13. In FIG. 13, total PSP94 is captured with the P1E8 antibody, and a high concentration (excess) of biotinylated 2D3 is used to encourage the dissociation (displacement) of a PSP94-binding protein. In the previously described assay, the actual concentration of 2D3 for coating the plate is low as the plastic has a capacity of no more than 50 ng.

Note, that this assay may also measure free (unbound) PSP94, if the complex (PSP94/PSP94-binding protein) is adsorbed out from the serum prior to measurement.

EXAMPLE 15

PSP94-Binding Protein Immunodetection Assays

Specificity for all the PSP94-binding protein antibodies has been confirmed in the ELISA assay discussed previously, and by Western blot. Each of them recognizes both the high and low molecular weight form of the binding protein by western blot.

Figure 14A:
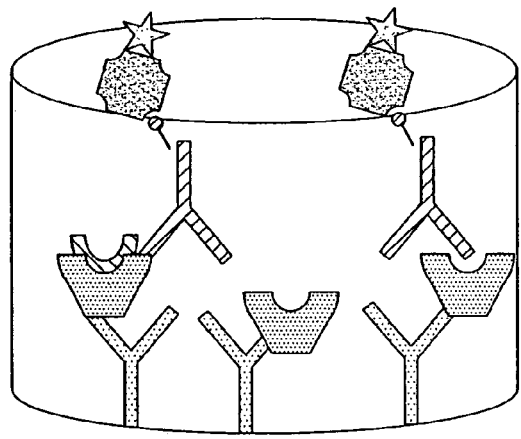
FIG. 14a is a schematic of a method used to measure the amount of total PSP94-binding protein (using a PSP94-binding protein sandwich ELISA) in a sample.

As shown in table 10, the antibody 17G9 recognize a different epitope than 3F4. Thus a sandwich ELISA assay, as illustrated in FIG. 14a, has been developed using these two antibodies. FIG. 14b illustrates a standard curve from the assays used to measure a PSP94-binding protein within serum samples. Note that these two antibodies may be interchanged. For example, the capture antibody can be switched to be used as detection reagent (when labeled).

Forty serum samples from male donors have been assessed with a PSP94-binding protein ELISA assay described above (illustrated in FIG. 14a). The PSP94-binding protein serum concentration was successfully measured. Values of PSP94-binding protein in these male donors ranged from about 1 µg/ml to about 10 µg/ml, with two cases having in excess of 20 µg/ml. Two cases from female donors have been assessed; one has about 3 µg/ml, the other about 7.8 µg/ml.

EXAMPLE 16

Immunodetection Assays Application

Male human serum samples with known total PSA values were obtained from a reference standard laboratory. Forty cases had low total PSA serum levels (<4 ng per ml) and 69 had high total PSA serum levels (>4 ng per ml). Analysis was performed on these low and high categories. There is no traceable link back to these patients, thus, there is no clinical information associated with the specimens, except for the total PSA value. The purpose of this analysis is to look for trends and patterns rather than determine the clinical relevance of PSP94 measurements. The distributions of the serum concentrations of total PSP94, PSP94-binding protein, free PSP94 and corrected free PSP94 are illustrated in additional figures described herein.

Figure 15A:
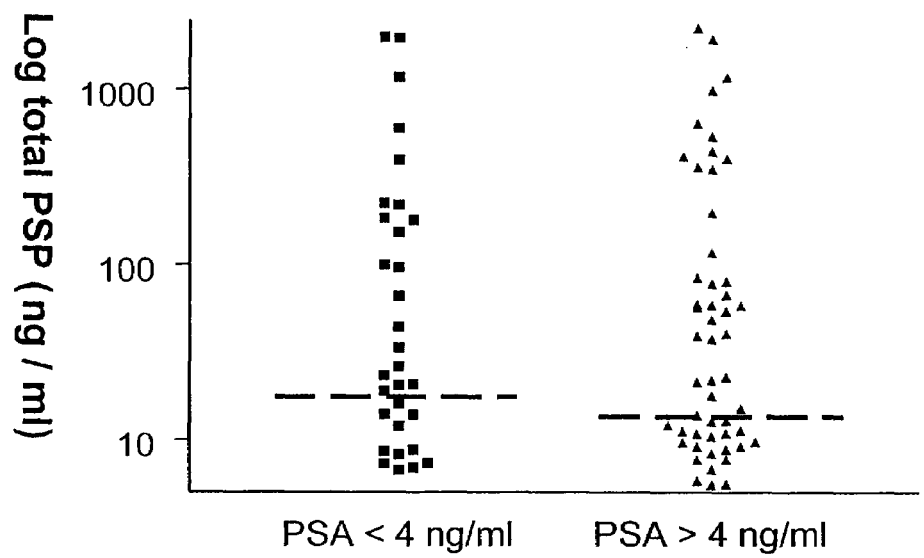
FIG. 15A represents concentration of total PSP94 levels from serum of individuals in low (<4 ng/ml) and high (>4 ng/ml) PSA categories.

With respect to additional figures;

FIG. 15A, is a graph illustrating results obtained following measurement of total PSP94 in serum of individuals for which PSA values are known to be lower or higher than the cut-off value of 4 ng/ml and using an assay as illustrated in FIG. 13 and described in example 14. Results are expressed as the log of total PSP94 concentration (in ng/ml) measured for each individual. Each point represents results obtained for a specific individual. With respect to this figure, total PSP94 concentration of 1 to 2250 ng/ml were measured in serum of individuals.

Figure 15B:
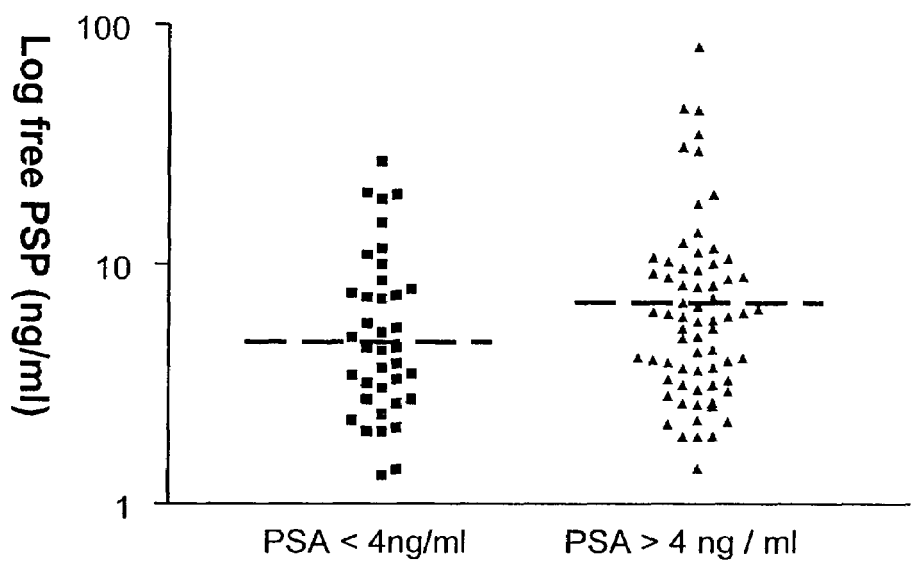
FIG. 15B represents concentration of free PSP94 levels from serum of individuals in low (<4 ng/ml) and high (>4 ng/ml) PSA categories.

With respect to FIG. 15B, this figure is a graph illustrating results obtained following measurement of free PSP94 in serum of individuals for which PSA values are known to be lower or higher than the cut-off value of 4 ng/ml. Results were obtained using an assay which is based on the removal (depletion) of PSP94-binding protein and PSP94/PSP94-binding protein complex from serum using an anti-PSP94-binding protein antibody as described herein prior to measurement of free PSP94 with the 2D3 and P1E8 monoclonal antibodies in a sandwich ELISA assay. Results are expressed as the log of free PSP94 concentration (in ng/ml) measured for each individual. Each point represent results obtained for a specific individual.

Figure 15C:
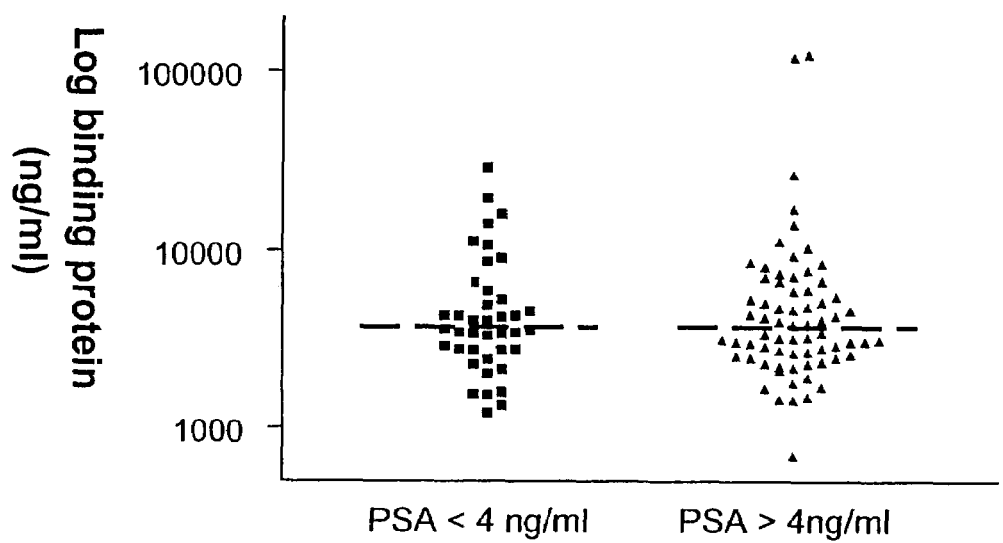
FIG. 15C represents concentration of total PSP94 Binding protein levels from serum of individuals in low (<4 ng/ml) and high (>4 ng/ml) PSA categories.

With respect to FIG. 15C, this figure is a graph illustrating results obtained following measurement of total PSP94-binding protein in serum of individuals for which PSA values are known to be lower or higher than the cut-off value of 4 ng/ml. Results were obtained using an assay which is illustrated in FIG. 14a and described in example 15. Results are expressed as the log of total PSP94-binding protein concentration (in ng/ml) measured for each individual. Each point represent results obtained for a specific individual. With respect to this figure, PSP94-binding protein concentration ranging from 0.7 to 125 micrograms/ml were measured in serum of individuals.

Figure 15D:
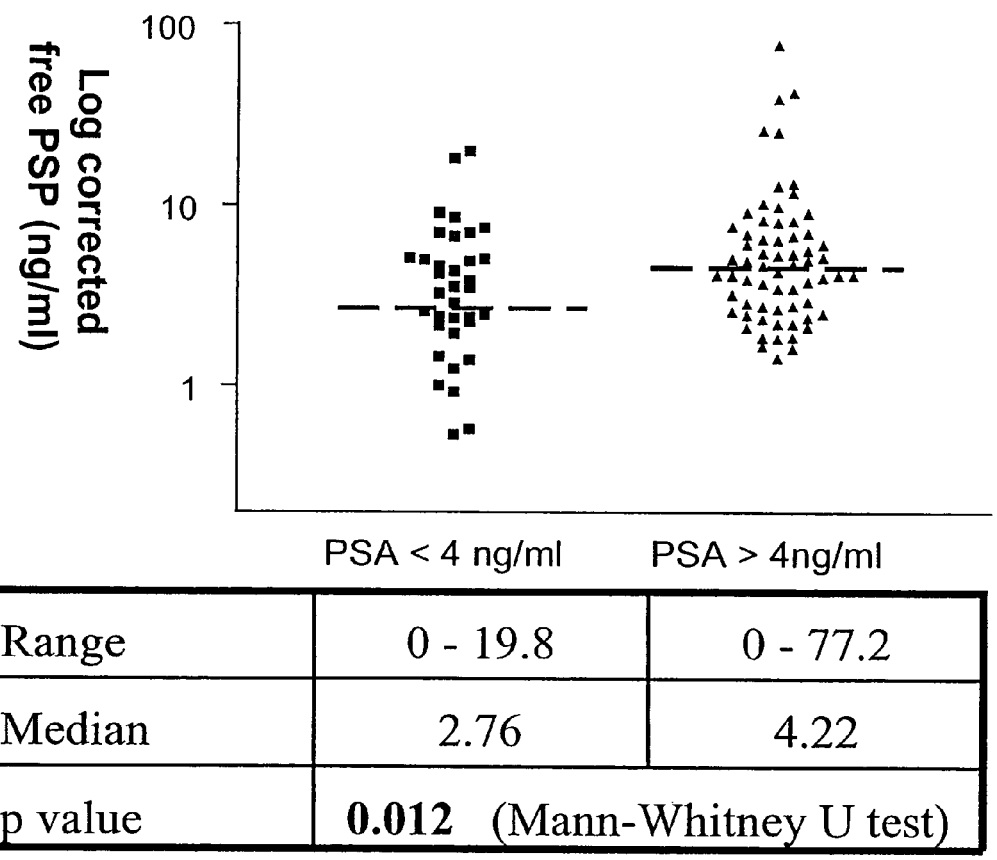
FIG. 15D represents concentration of corrected free PSP94 levels from serum of individuals in low (<4 ng/ml) and high (>4 ng/ml) PSA categories. Free PSP94 values were corrected since 1-5% of PSP94 binding protein (and complexed PSP94) remained after absorption protocol. The correction subtracts the bound PSP94×proportion of PSP94 binding protein not absorbed from the uncorrected free PSP94 value.

With respect to FIG. 15D, this figure is a graph illustrating results obtained following correction of the free PSP94 concentration obtained in serum of individuals for which PSA values are known to be lower or higher than the cut-off value of 4 ng/ml; Results were corrected by taking into account that 1 to 5% of residual PSP94/PSP94-binding protein complex remains in the serum even after depletion which may affect the results obtain, i.e., PSP94 may be dissociated from the complex after the 2D3 antibody is added, falsely increasing the "free PSP94" value. Results are again expressed as the log of corrected free PSP94 concentration (in ng/ml) measured for each individual. Each point represent results obtained for a specific individual. With respect to this figure, corrected free PSP94 levels were significantly elevated in the high PSA category (>4 ng/ml).

Figure 16:
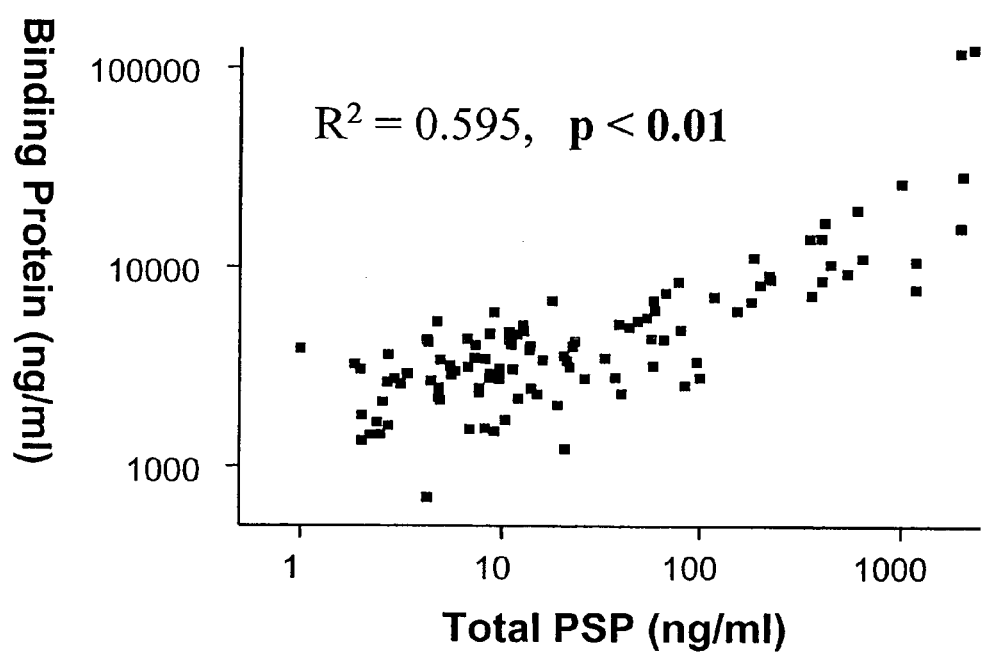
FIG. 16 represents total PSP94 binding protein concentration compared to total PSP94.

FIG. 16, is a graph illustrating the total PSP94-binding protein concentration (ng/ml) versus the total PSP94 concentration (ng/ml) measured in serum of individuals, where each point represent results obtained for a specific individual. With respect to this figure, a significant positive relationship between these two parameters may be observed.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

We claim:

1. An hybridoma cell line producing an antibody that binds to an epitope of PSP94 which is available when PSP94 is in a free form which is deposited to the ATCC under Patent Deposit No.: PTA-6599.

2. An antibody able to bind to an epitope of PSP94 which is available when PSP94 is in a free form, wherein said antibody is produced by a hybridoma cell line deposited to the ATCC under Patent Deposit No.: PTA-6599 or is an antigen binding fragment thereof.

3. A kit comprising the antibody of claim 2.

4. The kit of claim 3, wherein said antibody is conjugated with a reporter molecule.

5. The kit of claim 4, wherein said reporter molecule is an enzyme.

6. The kit of claim 5, wherein said enzyme is a peroxidase.

7. The kit of claim 6, wherein said enzyme is horseradish peroxidase.

8. The kit of claim 3, further comprising a control sample containing a known amount of PSP94.

9. The kit of claim 3, further comprising an isolated polyclonal antibody which binds to PSP94.

10. The kit of claim 3, further comprising a second isolated antibody binding to a different epitope of PSP94.

11. The kit of claim 10, wherein said second antibody is produced by a hybridoma cell line deposited to the ATCC under Patent Deposit No.: PTA-4240.

12. The kit of claim 3, wherein said antibody is bound to a solid matrix.

13. The kit of claim 12, wherein unspecific binding sites of said solid matrix are blocked.

14. A method for detecting or measuring a free form of PSP94 in a sample, the method comprising:
    a) contacting said sample with an antibody able to specifically bind to an epitope of PSP94 which is available when PSP94 is in a free form, wherein said antibody is produced by a hybridoma cell line deposited to the ATCC under Patent Deposit No.: PTA-6599 or is an antigen binding fragment thereof; and,
    b) detecting a complex formed by said antibody and the free form of PSP94 in the contacted sample thereby detecting or measuring the free form of PSP94 in the sample.

15. The method of claim 14, wherein the free form of PSP94 in the sample is quantitatively compared with a control sample containing a predetermined amount of PSP94.

16. The method of claim 14, wherein said sample is selected from the group consisting of blood, plasma, serum, urine, seminal fluid, cell culture media and cell lysate.

17. An antibody conjugate comprising a first moiety and a second moiety, said first moiety being an antibody able to bind to an epitope of PSP94 which is available when PSP94 is in a free form wherein said first moiety is an antibody produced by a hybridoma cell line deposited to the ATCC under Patent Deposit No.: PTA-6599 and said second moiety being selected from the group consisting of a pharmaceutical agent, a solid support, a reporter molecule, a group carrying a reporter molecule, a chelating agent, an acylating agent, a cross-linking agent, and a targeting group.

* * * * *

SEQUENCE LISTING

<160> NUMBER OF SEQ ID NOS: 9

<210> SEQ ID NO 1
<211> LENGTH: 2005
<212> TYPE: DNA
<213> ORGANISM: Homo sapiens

<400> SEQUENCE: 1

```
atgcacggct cctgcagttt cctgatgctt ctgctgccgc tactgctact gctggtggcc      60
accacaggcc ccgttggagc cctcacagat gaggagaaac gtttgatggt ggagctgcac     120
aacctctacc gggcccaggt atccccgacg gcctcagaca tgctgcacat gagatgggac     180
gaggagctgg ccgccttcgc caaggcctac gcacggcagt gcgtgtgggg ccacaacaag     240
gagcgcgggc gccgcggcga gaatctgttc gccatcacag acgagggcat ggacgtgccg     300
ctggccatgg aggagtggca ccacgagcgt gagcactaca acctcagcgc cgccacctgc     360
agcccaggcc agatgtgcgg ccactacacg caggtggtat gggccaagac agagaggatc     420
ggctgtggtt cccacttctg tgagaagctc cagggtgttg aggagaccaa catcgaatta     480
ctggtgtgca actatgagcc tccggggaac gtgaagggga acggcccta ccaggagggg      540
actccgtgct cccaatgtcc ctctggctac cactgcaaga actccctctg tggtgagtcc     600
acgggtggat ggccccccac gcgcagccac tttggcgccc tgtcgttcca agtggccgga     660
tttcaacccct tcaaagggag gatgttagaa agtctggcgg cttcgggggg gcccgcgcga     720
gaacccatcg gaagcccgga agatgctcag gatttgcctt acctggtaac tgaggcccca     780
tccttccggg cgactgaagc atcagactct aggaaaatgg gtactccttc ttccctagca     840
acggggattc cggctttctt ggtaacagag gtctcaggct ccctggcaac caaggctctg     900
cctgctgtgg aaacccaggc cccaacttcc ttagcaacga agacccgcc ctccatggca      960
acagaggctc caccttgcgt aacaactgag gtcccttcca ttttggcagc tcacagcctg    1020
ccctccttgg atgaggagcc agttaccttc cccaaatcga cccatgttcc tatcccaaaa    1080
tcagcagaca aagtgacaga caaaacaaaa gtgccctcta ggagcccaga gaactctctg    1140
gaccccaaga tgtccctgac aggggcaagg gaactcctac cccatgccca ggaggaggct    1200
gaggctgagg ctgagttgcc tccttccagt gaggtcttgg cctcagtttt tccagcccag    1260
gacaagccag gtgagctgca ggccacactg gaccacacgg ggcacacctc ctccaagtcc    1320
ctgcccaatt tccccaatac ctctgccacc gctaatgcca cgggtgggcg tgccctggct    1380
ctgcagtcgt ccttgccagg tgcagagggc cctgacaagc ctagcgtcgt gtcagggctg    1440
aactcgggcc ctggtcatgt gtggggccct tcctgggac tactgctcct gcctcctctg     1500
gtgttggctg aatcttctg aaggggatac cactcaaagg gtgaagaggt cagctgtcct    1560
cctgtcatct tccccaccct gtccccagcc cctaaacaag atacttcttg gttaaggccc    1620
tccggaaggg aaaggctacg ggcatgtgc ctcatcacac catccatcct ggaggcacaa     1680
ggcctggctg gctgcgagct caggaggccg cctgaggact gcacaccggg cccacacctc    1740
tcctgcccct ccctcctgag tcctgggggt gggaggattt gagggagctc actgcctacc    1800
tggcctgggg ctgtctgccc acacagcatg tgcgctctcc ctgagtgcct gtgtagctgg    1860
ggatggggat tcctagggggc agatgaagga caagccccac tggagtgggg ttctttgagt    1920
gggggaggca gggacgaggg aaggaaagta actcctgact ctccaataaa aacctgtcca    1980
acctgtggca aaaaaaaaa aaaaa                                            2005
```

<210> SEQ ID NO 2
<211> LENGTH: 506
<212> TYPE: PRT
<213> ORGANISM: Homo sapiens

<400> SEQUENCE: 2

-continued

```
Met His Gly Ser Cys Ser Phe Leu Met Leu Leu Pro Leu Leu Leu
1               5                   10                  15

Leu Leu Val Ala Thr Thr Gly Pro Val Gly Ala Leu Thr Asp Glu Glu
            20                  25                  30

Lys Arg Leu Met Val Glu Leu His Asn Leu Tyr Arg Ala Gln Val Ser
                35                  40                  45

Pro Thr Ala Ser Asp Met Leu His Met Arg Trp Asp Glu Glu Leu Ala
    50                  55                  60

Ala Phe Ala Lys Ala Tyr Ala Arg Gln Cys Val Trp Gly His Asn Lys
65                  70                  75                  80

Glu Arg Gly Arg Arg Gly Glu Asn Leu Phe Ala Ile Thr Asp Glu Gly
                85                  90                  95

Met Asp Val Pro Leu Ala Met Glu Glu Trp His His Gly Arg Glu His
            100                 105                 110

Tyr Asn Leu Ser Ala Ala Thr Cys Ser Pro Gly Gln Met Cys Gly His
                115                 120                 125

Tyr Thr Gln Val Val Trp Ala Lys Thr Glu Arg Ile Gly Cys Gly Ser
    130                 135                 140

His Phe Cys Glu Lys Leu Gln Gly Val Glu Glu Thr Asn Ile Glu Leu
145                 150                 155                 160

Leu Val Cys Asn Tyr Glu Pro Pro Gly Asn Val Lys Gly Lys Arg Pro
                165                 170                 175

Tyr Gln Glu Gly Thr Pro Cys Ser Gln Cys Pro Ser Gly Tyr His Cys
            180                 185                 190

Lys Asn Ser Leu Cys Gly Glu Ser Thr Gly Gly Trp Pro Pro Thr Arg
        195                 200                 205

Ser His Phe Gly Ala Leu Ser Phe Gln Val Ala Gly Phe Gln Pro Phe
    210                 215                 220

Lys Gly Arg Met Leu Glu Ser Leu Ala Ala Ser Gly Gly Pro Ala Arg
225                 230                 235                 240

Glu Pro Ile Gly Ser Pro Glu Asp Ala Gln Asp Leu Pro Tyr Leu Val
                245                 250                 255

Thr Glu Ala Pro Ser Phe Arg Ala Thr Glu Ala Ser Asp Ser Arg Lys
            260                 265                 270

Met Gly Thr Pro Ser Ser Leu Ala Thr Gly Ile Pro Ala Phe Leu Val
        275                 280                 285

Thr Glu Val Ser Gly Ser Leu Ala Thr Lys Ala Leu Pro Ala Val Glu
    290                 295                 300

Thr Gln Ala Pro Thr Ser Leu Ala Thr Lys Asp Pro Pro Ser Met Ala
305                 310                 315                 320

Thr Glu Ala Pro Pro Cys Val Thr Thr Glu Val Pro Ser Ile Leu Ala
                325                 330                 335

Ala His Ser Leu Pro Ser Leu Asp Glu Glu Pro Val Thr Phe Pro Lys
            340                 345                 350

Ser Thr His Val Pro Ile Pro Lys Ser Ala Asp Lys Val Thr Asp Lys
        355                 360                 365

Thr Lys Val Pro Ser Arg Ser Pro Glu Asn Ser Leu Asp Pro Lys Met
    370                 375                 380

Ser Leu Thr Gly Ala Arg Glu Leu Leu Pro His Ala Gln Glu Glu Ala
385                 390                 395                 400

Glu Ala Glu Ala Glu Leu Pro Pro Ser Ser Glu Val Leu Ala Ser Val
                405                 410                 415

Phe Pro Ala Gln Asp Lys Pro Gly Glu Leu Gln Ala Thr Leu Asp His
```

```
                420             425             430
Thr Gly His Thr Ser Ser Lys Ser Leu Pro Asn Phe Pro Asn Thr Ser
            435             440             445
Ala Thr Ala Asn Ala Thr Gly Gly Arg Ala Leu Ala Leu Gln Ser Ser
        450             455             460
Leu Pro Gly Ala Glu Gly Pro Asp Lys Pro Ser Val Val Ser Gly Leu
465             470             475             480
Asn Ser Gly Pro Gly His Val Trp Gly Pro Leu Leu Gly Leu Leu Leu
                485             490             495
Leu Pro Pro Leu Val Leu Ala Gly Ile Phe
            500             505

<210> SEQ ID NO 3
<211> LENGTH: 593
<212> TYPE: PRT
<213> ORGANISM: Homo sapiens
<220> FEATURE:
<221> NAME/KEY: MISC_FEATURE
<222> LOCATION: (507)..(507)
<223> OTHER INFORMATION: Xaa may be any amino acid  (e.g., Ala, Cys,
      Asp, Glu, Phe, Gly, His, Ile, Lys, Leu, Met, Asn, Pro, Gln, Arg,
      Ser, Thr, Val, Trp, Tyr)

<400> SEQUENCE: 3

Met His Gly Ser Cys Ser Phe Leu Met Leu Leu Pro Leu Leu Leu
1               5                   10                  15

Leu Leu Val Ala Thr Thr Gly Pro Val Gly Ala Leu Thr Asp Glu Glu
            20                  25                  30

Lys Arg Leu Met Val Glu Leu His Asn Leu Tyr Arg Ala Gln Val Ser
        35                  40                  45

Pro Thr Ala Ser Asp Met Leu His Met Arg Trp Asp Glu Glu Leu Ala
    50                  55                  60

Ala Phe Ala Lys Ala Tyr Ala Arg Gln Cys Val Trp Gly His Asn Lys
65                  70                  75                  80

Glu Arg Gly Arg Arg Gly Glu Asn Leu Phe Ala Ile Thr Asp Glu Gly
                85                  90                  95

Met Asp Val Pro Leu Ala Met Glu Glu Trp His His Glu Arg Glu His
            100                 105                 110

Tyr Asn Leu Ser Ala Ala Thr Cys Ser Pro Gly Gln Met Cys Gly His
        115                 120                 125

Tyr Thr Gln Val Val Trp Ala Lys Thr Glu Arg Ile Gly Cys Gly Ser
    130                 135                 140

His Phe Cys Glu Lys Leu Gln Gly Val Glu Glu Thr Asn Ile Glu Leu
145                 150                 155                 160

Leu Val Cys Asn Tyr Glu Pro Pro Gly Asn Val Lys Gly Lys Arg Pro
                165                 170                 175

Tyr Gln Glu Gly Thr Pro Cys Ser Gln Cys Pro Ser Tyr His Cys
            180                 185                 190

Lys Asn Ser Leu Cys Gly Glu Ser Thr Gly Gly Trp Pro Pro Thr Arg
        195                 200                 205

Ser His Phe Gly Ala Leu Ser Phe Gln Val Ala Gly Phe Gln Pro Phe
    210                 215                 220

Lys Gly Arg Met Leu Glu Ser Leu Ala Ala Ser Gly Gly Pro Ala Arg
225                 230                 235                 240

Glu Pro Ile Gly Ser Pro Glu Asp Ala Gln Asp Leu Pro Tyr Leu Val
                245                 250                 255
```

-continued

```
Thr Glu Ala Pro Ser Phe Arg Ala Thr Glu Ala Ser Asp Ser Arg Lys
            260                 265                 270

Met Gly Thr Pro Ser Ser Leu Ala Thr Gly Ile Pro Ala Phe Leu Val
        275                 280                 285

Thr Glu Val Ser Gly Ser Leu Ala Thr Lys Ala Leu Pro Ala Val Glu
    290                 295                 300

Thr Gln Ala Pro Thr Ser Leu Ala Thr Lys Asp Pro Pro Ser Met Ala
305                 310                 315                 320

Thr Glu Ala Pro Pro Cys Val Thr Thr Glu Val Pro Ser Ile Leu Ala
                325                 330                 335

Ala His Ser Leu Pro Ser Leu Asp Glu Pro Val Thr Phe Pro Lys
            340                 345                 350

Ser Thr His Val Pro Ile Pro Lys Ser Ala Asp Lys Val Thr Asp Lys
        355                 360                 365

Thr Lys Val Pro Ser Arg Ser Pro Glu Asn Ser Leu Asp Pro Lys Met
    370                 375                 380

Ser Leu Thr Gly Ala Arg Glu Leu Leu Pro His Ala Gln Glu Glu Ala
385                 390                 395                 400

Glu Ala Glu Ala Glu Leu Pro Pro Ser Ser Glu Val Leu Ala Ser Val
                405                 410                 415

Phe Pro Ala Gln Asp Lys Pro Gly Glu Leu Gln Ala Thr Leu Asp His
            420                 425                 430

Thr Gly His Thr Ser Ser Lys Ser Leu Pro Asn Phe Pro Asn Thr Ser
        435                 440                 445

Ala Thr Ala Asn Ala Thr Gly Gly Arg Ala Leu Ala Leu Gln Ser Ser
    450                 455                 460

Leu Pro Gly Ala Glu Gly Pro Asp Lys Pro Ser Val Val Ser Gly Leu
465                 470                 475                 480

Asn Ser Gly Pro Gly His Val Trp Gly Pro Leu Leu Gly Leu Leu
                485                 490                 495

Leu Pro Pro Leu Val Leu Ala Gly Ile Phe Xaa Arg Gly Tyr His Ser
            500                 505                 510

Lys Gly Glu Glu Val Ser Cys Pro Pro Val Ile Phe Pro Thr Leu Ser
        515                 520                 525

Pro Ala Pro Lys Gln Asp Thr Ser Trp Leu Arg Pro Ser Gly Arg Glu
    530                 535                 540

Arg Leu Arg Gly Met Cys Leu Ile Thr Pro Ser Ile Leu Glu Ala Gln
545                 550                 555                 560

Gly Leu Ala Gly Cys Glu Leu Arg Arg Pro Glu Asp Cys Thr Pro
                565                 570                 575

Gly Pro His Leu Ser Cys Pro Ser Leu Leu Ser Pro Gly Gly Gly Arg
            580                 585                 590

Ile
```

<210> SEQ ID NO 4
<211> LENGTH: 30
<212> TYPE: DNA
<213> ORGANISM: Homo sapiens

<400> SEQUENCE: 4
atgcacggct cctgcagttt cctgatgctt                                      30

<210> SEQ ID NO 5
<211> LENGTH: 37
<212> TYPE: DNA

<213> ORGANISM: Homo sapiens

<400> SEQUENCE: 5

```
gcccacgcgt cgactagtac ttttttttt tttttt                                37
```

<210> SEQ ID NO 6
<211> LENGTH: 1876
<212> TYPE: DNA
<213> ORGANISM: Homo sapiens

<400> SEQUENCE: 6

```
atgcacggct cctgcagttt cctgatgctt ctgctgccgc tactgctact gctggtggcc     60
accacaggcc ccgttggagc cctcacagat gaggagaaac gtttgatggt ggagctgcac    120
aacctctacc gggcccaggt atccccgccg gcctcagaca tgctgcacat gagatgggac    180
gaggagctgg ccgccttcgc caaggcctac gcacggcagt gcgtgtgggg ccacaacaag    240
gagcgcgggg ccgcggcga gaatctgttc gccatcacag acgagggcat ggacgtgccg    300
ctggccatgg aggagtggca ccacgagcgt gagcactaca acctcagcgc cgccacctgc    360
agcccaggcc agatgtgcgg ccactacacg caggtggtat gggccaagac agagaggatc    420
ggctgtggtt cccacttctg tgagaagctc agggtgttg aggagaccaa catcgaatta    480
ctggtgtgca actatgagcc tccggggaac gtgaaggga acggccccta ccaggagggg    540
actccgtgct cccaatgtcc ctctggctac cactgcaaga actccctctg tgaacccatc    600
ggaagcccgg aagatgctca ggatttgcct tacctggtaa ctgaggcccc atccttccgg    660
gcgactgaag catcagactc taggaaaatg ggtgctcctt cttccctagc aacggggatt    720
ccggcttttc tggtcacagg ggtgtcaggc tcgctgccaa ccctgggact gcctgctgtg    780
gaaacccagg ccccaacttc cttagcaacg aaagacccgc cctccatggc aacagaggct    840
ccacttgcg taacaactga ggtcccttcc attttggcag ctcacagcct gcctccttg    900
gatgaggagc cagttacctt ccccaaatcg acccatgttc ctatcccaaa atcagcagac    960
aaagtgacag acaaaacaaa agtgccctct aggagcccag agaactctct ggaccccaag   1020
atgtccctga caggggcaag ggaactccta ccccatgccc aggaggaggc tgaggctgag   1080
gctgagttgc ctccttccag tgaggtcttg gcctcagttt ttccagccca ggacaagcca   1140
ggtgagctgc aggccacact ggaccacacg gggcacacct cctccaagtc cctgccaat   1200
ttccccaata cctctgccac cgctaatgcc acgggtgggc gtgccctggc tctgcagtcg   1260
tccttgccag gtgcagaggg ccctgacaag cctagcgtcg tgtcagggct gaactcgggc   1320
cctggtcatg tgtggggccc tctcctggga ctactgctcc tgcctcctct ggtgttggct   1380
ggaatcttct gaagggata ccactcaaag ggtgaagagg tcagctgtcc tcctgtcatc   1440
ttccccaccc tgtccccagc ccctaaacaa gatacttctt ggttaaggcc ctccggaagg   1500
gaaaggctac ggggcatgtg cctcatcaca ccatccatcc tggaggcaca aggcctggct   1560
ggctgcgagc tcaggaggcc gcctgaggac tgcacaccgg gcccacacct ctcctgcccc   1620
tccctcctga gtcctggggg tgggaggatt tgagggagct cactgcctac ctggcctggg   1680
gctgtctgcc cacacagcat gtgcgctctc cctgagtgcc tgtgtagctg gggatgggga   1740
ttcctagggg cagatgaagg acaagcccca ctggagtggg gttctttgag tgggggaggc   1800
agggacgagg gaaggaaagt aactcctgac tctccaataa aaacctgtcc aacctgtggc   1860
aaaaaaaaaa aaaaaa                                                    1876
```

-continued

```
<210> SEQ ID NO 7
<211> LENGTH: 625
<212> TYPE: PRT
<213> ORGANISM: Homo sapiens
<220> FEATURE:
<221> NAME/KEY: MISC_FEATURE
<222> LOCATION: (464)..(464)
<223> OTHER INFORMATION: Xaa may be any amino acid (e.g., Ala, Cys, Asp,
      Glu, Phe, Gly, His, Ile, Lys, Leu, Met, Asn, Pro, Gln, Arg, Ser,
      Thr, Val, Trp, Tyr)
<220> FEATURE:
<221> NAME/KEY: MISC_FEATURE
<222> LOCATION: (551)..(551)
<223> OTHER INFORMATION: Xaa may be any amino acid (e.g., Ala, Cys, Asp,
      Glu, Phe, Gly, His, Ile, Lys, Leu, Met, Asn, Pro, Gln, Arg, Ser,
      Thr, Val, Trp, Tyr)

<400> SEQUENCE: 7

Met His Gly Ser Cys Ser Phe Leu Met Leu Leu Pro Leu Leu Leu
1               5                   10                  15

Leu Leu Val Ala Thr Thr Gly Pro Val Gly Ala Leu Thr Asp Glu Glu
            20                  25                  30

Lys Arg Leu Met Val Glu Leu His Asn Leu Tyr Arg Ala Gln Val Ser
        35                  40                  45

Pro Pro Ala Ser Asp Met Leu His Met Arg Trp Asp Glu Glu Leu Ala
    50                  55                  60

Ala Phe Ala Lys Ala Tyr Ala Arg Gln Cys Val Trp Gly His Asn Lys
65                  70                  75                  80

Glu Arg Gly Arg Arg Gly Glu Asn Leu Phe Ala Ile Thr Asp Glu Gly
                85                  90                  95

Met Asp Val Pro Leu Ala Met Glu Glu Trp His His Glu Arg Glu His
            100                 105                 110

Tyr Asn Leu Ser Ala Ala Thr Cys Ser Pro Gly Gln Met Cys Gly His
        115                 120                 125

Tyr Thr Gln Val Val Trp Ala Lys Thr Glu Arg Ile Gly Cys Gly Ser
    130                 135                 140

His Phe Cys Glu Lys Leu Gln Gly Val Glu Glu Thr Asn Ile Glu Leu
145                 150                 155                 160

Leu Val Cys Asn Tyr Glu Pro Pro Gly Asn Val Lys Gly Lys Arg Pro
                165                 170                 175

Tyr Gln Glu Gly Thr Pro Cys Ser Gln Cys Pro Ser Gly Tyr His Cys
            180                 185                 190

Lys Asn Ser Leu Cys Glu Pro Ile Gly Ser Pro Glu Asp Ala Gln Asp
        195                 200                 205

Leu Pro Tyr Leu Val Thr Glu Ala Pro Ser Phe Arg Ala Thr Glu Ala
    210                 215                 220

Ser Asp Ser Arg Lys Met Gly Ala Pro Ser Ser Leu Ala Thr Gly Ile
225                 230                 235                 240

Pro Ala Phe Leu Val Thr Gly Val Ser Gly Ser Leu Pro Thr Leu Gly
                245                 250                 255

Leu Pro Ala Val Glu Thr Gln Ala Pro Thr Ser Leu Ala Thr Lys Asp
            260                 265                 270

Pro Pro Ser Met Ala Thr Glu Ala Pro Pro Cys Val Thr Thr Glu Val
        275                 280                 285

Pro Ser Ile Leu Ala Ala His Ser Leu Pro Ser Leu Asp Glu Glu Pro
    290                 295                 300

Val Thr Phe Pro Lys Ser Thr His Val Pro Ile Pro Lys Ser Ala Asp
305                 310                 315                 320
```

-continued

```
Lys Val Thr Asp Lys Thr Lys Val Pro Ser Arg Ser Pro Glu Asn Ser
                325                 330                 335

Leu Asp Pro Lys Met Ser Leu Thr Gly Ala Arg Glu Leu Leu Pro His
            340                 345                 350

Ala Gln Glu Glu Ala Glu Ala Glu Leu Pro Pro Ser Ser Glu
        355                 360                 365

Val Leu Ala Ser Val Phe Pro Ala Gln Asp Lys Pro Gly Glu Leu Gln
    370                 375                 380

Ala Thr Leu Asp His Thr Gly His Thr Ser Ser Lys Ser Leu Pro Asn
385                 390                 395                 400

Phe Pro Asn Thr Ser Ala Thr Ala Asn Ala Thr Gly Gly Arg Ala Leu
                405                 410                 415

Ala Leu Gln Ser Ser Leu Pro Gly Ala Glu Gly Pro Asp Lys Pro Ser
            420                 425                 430

Val Val Ser Gly Leu Asn Ser Gly Pro Gly His Val Trp Gly Pro Leu
        435                 440                 445

Leu Gly Leu Leu Leu Leu Pro Pro Leu Val Leu Ala Gly Ile Phe Xaa
    450                 455                 460

Arg Gly Tyr His Ser Lys Gly Glu Glu Val Ser Cys Pro Pro Val Ile
465                 470                 475                 480

Phe Pro Thr Leu Ser Pro Ala Pro Lys Gln Asp Thr Ser Trp Leu Arg
                485                 490                 495

Pro Ser Gly Arg Glu Arg Leu Arg Gly Met Cys Leu Ile Thr Pro Ser
            500                 505                 510

Ile Leu Glu Ala Gln Gly Leu Ala Gly Cys Glu Leu Arg Arg Pro Pro
        515                 520                 525

Glu Asp Cys Thr Pro Gly Pro His Leu Ser Cys Pro Ser Leu Leu Ser
    530                 535                 540

Pro Gly Gly Gly Arg Ile Xaa Gly Ser Ser Leu Pro Thr Trp Pro Gly
545                 550                 555                 560

Ala Val Cys Pro His Ser Met Cys Ala Leu Pro Glu Cys Leu Cys Ser
                565                 570                 575

Trp Gly Trp Gly Phe Leu Gly Ala Asp Glu Gly Gln Ala Pro Leu Glu
            580                 585                 590

Trp Gly Ser Leu Ser Gly Gly Arg Asp Glu Gly Arg Lys Val Thr
        595                 600                 605

Pro Asp Ser Pro Ile Lys Thr Cys Pro Thr Cys Gly Lys Lys Lys Lys
    610                 615                 620
Lys
625

<210> SEQ ID NO 8
<211> LENGTH: 550
<212> TYPE: PRT
<213> ORGANISM: Homo sapiens
<220> FEATURE:
<221> NAME/KEY: MISC_FEATURE
<222> LOCATION: (464)..(464)
<223> OTHER INFORMATION: Xaa may be any amino acid

<400> SEQUENCE: 8

Met His Gly Ser Cys Ser Phe Leu Met Leu Leu Pro Leu Leu Leu
1               5                   10                  15

Leu Leu Val Ala Thr Thr Gly Pro Val Gly Ala Leu Thr Asp Glu Glu
            20                  25                  30

Lys Arg Leu Met Val Glu Leu His Asn Leu Tyr Arg Ala Gln Val Ser
```

-continued

```
                35                  40                  45
Pro Pro Ala Ser Asp Met Leu His Met Arg Trp Asp Glu Glu Leu Ala
        50                  55                  60
Ala Phe Ala Lys Ala Tyr Ala Arg Gln Cys Val Trp Gly His Asn Lys
 65                  70                  75                  80
Glu Arg Gly Arg Arg Gly Glu Asn Leu Phe Ala Ile Thr Asp Glu Gly
                 85                  90                  95
Met Asp Val Pro Leu Ala Met Glu Glu Trp His His Glu Arg Glu His
            100                 105                 110
Tyr Asn Leu Ser Ala Ala Thr Cys Ser Pro Gly Gln Met Cys Gly His
            115                 120                 125
Tyr Thr Gln Val Val Trp Ala Lys Thr Glu Arg Ile Gly Cys Gly Ser
        130                 135                 140
His Phe Cys Glu Lys Leu Gln Gly Val Glu Glu Thr Asn Ile Glu Leu
145                 150                 155                 160
Leu Val Cys Asn Tyr Glu Pro Pro Gly Asn Val Lys Gly Lys Arg Pro
                165                 170                 175
Tyr Gln Glu Gly Thr Pro Cys Ser Gln Cys Pro Ser Gly Tyr His Cys
            180                 185                 190
Lys Asn Ser Leu Cys Glu Pro Ile Gly Ser Pro Glu Asp Ala Gln Asp
            195                 200                 205
Leu Pro Tyr Leu Val Thr Glu Ala Pro Ser Phe Arg Ala Thr Glu Ala
        210                 215                 220
Ser Asp Ser Arg Lys Met Gly Ala Pro Ser Ser Leu Ala Thr Gly Ile
225                 230                 235                 240
Pro Ala Phe Leu Val Thr Gly Val Ser Gly Ser Leu Pro Thr Leu Gly
                245                 250                 255
Leu Pro Ala Val Glu Thr Gln Ala Pro Thr Ser Leu Ala Thr Lys Asp
            260                 265                 270
Pro Pro Ser Met Ala Thr Glu Ala Pro Pro Cys Val Thr Thr Glu Val
            275                 280                 285
Pro Ser Ile Leu Ala Ala His Ser Leu Pro Ser Leu Asp Glu Glu Pro
        290                 295                 300
Val Thr Phe Pro Lys Ser Thr His Val Pro Ile Pro Lys Ser Ala Asp
305                 310                 315                 320
Lys Val Thr Asp Lys Thr Lys Val Pro Ser Arg Ser Pro Glu Asn Ser
                325                 330                 335
Leu Asp Pro Lys Met Ser Leu Thr Gly Ala Arg Glu Leu Leu Pro His
            340                 345                 350
Ala Gln Glu Glu Ala Glu Ala Glu Ala Glu Leu Pro Pro Ser Ser Glu
            355                 360                 365
Val Leu Ala Ser Val Phe Pro Ala Gln Asp Lys Pro Gly Glu Leu Gln
        370                 375                 380
Ala Thr Leu Asp His Thr Gly His Thr Ser Ser Lys Ser Leu Pro Asn
385                 390                 395                 400
Phe Pro Asn Thr Ser Ala Thr Ala Asn Ala Thr Gly Gly Arg Ala Leu
                405                 410                 415
Ala Leu Gln Ser Ser Leu Pro Gly Ala Glu Gly Pro Asp Lys Pro Ser
            420                 425                 430
Val Val Ser Gly Leu Asn Ser Gly Pro Gly His Val Trp Gly Pro Leu
            435                 440                 445
Leu Gly Leu Leu Leu Leu Pro Pro Leu Val Leu Ala Gly Ile Phe Xaa
        450                 455                 460
```

-continued

```
Arg Gly Tyr His Ser Lys Gly Glu Glu Val Ser Cys Pro Pro Val Ile
465                 470                 475                 480

Phe Pro Thr Leu Ser Pro Ala Pro Lys Gln Asp Thr Ser Trp Leu Arg
                485                 490                 495

Pro Ser Gly Arg Glu Arg Leu Arg Gly Met Cys Leu Ile Thr Pro Ser
            500                 505                 510

Ile Leu Glu Ala Gln Gly Leu Ala Gly Cys Glu Leu Arg Arg Pro Pro
        515                 520                 525

Glu Asp Cys Thr Pro Gly Pro His Leu Ser Cys Pro Ser Leu Leu Ser
530                 535                 540

Pro Gly Gly Gly Arg Ile
545                 550

<210> SEQ ID NO 9
<211> LENGTH: 463
<212> TYPE: PRT
<213> ORGANISM: Homo sapiens

<400> SEQUENCE: 9

Met His Gly Ser Cys Ser Phe Leu Met Leu Leu Pro Leu Leu Leu
1               5                   10                  15

Leu Leu Val Ala Thr Thr Gly Pro Val Gly Ala Leu Thr Asp Glu Glu
                20                  25                  30

Lys Arg Leu Met Val Glu Leu His Asn Leu Tyr Arg Ala Gln Val Ser
            35                  40                  45

Pro Pro Ala Ser Asp Met Leu His Met Arg Trp Asp Glu Glu Leu Ala
        50                  55                  60

Ala Phe Ala Lys Ala Tyr Ala Arg Gln Cys Val Trp Gly His Asn Lys
65                  70                  75                  80

Glu Arg Gly Arg Arg Gly Glu Asn Leu Phe Ala Ile Thr Asp Glu Gly
                85                  90                  95

Met Asp Val Pro Leu Ala Met Glu Glu Trp His His Glu Arg Glu His
                100                 105                 110

Tyr Asn Leu Ser Ala Ala Thr Cys Ser Pro Gly Gln Met Cys Gly His
            115                 120                 125

Tyr Thr Gln Val Val Trp Ala Lys Thr Glu Arg Ile Gly Cys Gly Ser
        130                 135                 140

His Phe Cys Glu Lys Leu Gln Gly Val Glu Glu Thr Asn Ile Glu Leu
145                 150                 155                 160

Leu Val Cys Asn Tyr Glu Pro Pro Gly Asn Val Lys Gly Lys Arg Pro
                165                 170                 175

Tyr Gln Glu Gly Thr Pro Cys Ser Gln Cys Pro Ser Gly Tyr His Cys
            180                 185                 190

Lys Asn Ser Leu Cys Glu Pro Ile Gly Ser Pro Glu Asp Ala Gln Asp
        195                 200                 205

Leu Pro Tyr Leu Val Thr Glu Ala Pro Ser Phe Arg Ala Thr Glu Ala
    210                 215                 220

Ser Asp Ser Arg Lys Met Gly Ala Pro Ser Leu Ala Thr Gly Ile
225                 230                 235                 240

Pro Ala Phe Leu Val Thr Gly Val Ser Gly Ser Leu Pro Thr Leu Gly
                245                 250                 255

Leu Pro Ala Val Glu Thr Gln Ala Pro Thr Ser Leu Ala Thr Lys Asp
            260                 265                 270

Pro Pro Ser Met Ala Thr Glu Ala Pro Pro Cys Val Thr Thr Glu Val
```

-continued

```
                275                 280                 285
Pro Ser Ile Leu Ala Ala His Ser Leu Pro Ser Leu Asp Glu Glu Pro
        290                 295                 300

Val Thr Phe Pro Lys Ser Thr His Val Pro Ile Pro Lys Ser Ala Asp
305                 310                 315                 320

Lys Val Thr Asp Lys Thr Lys Val Pro Ser Arg Ser Pro Glu Asn Ser
                325                 330                 335

Leu Asp Pro Lys Met Ser Leu Thr Gly Ala Arg Glu Leu Leu Pro His
            340                 345                 350

Ala Gln Glu Glu Ala Glu Ala Glu Leu Pro Pro Ser Ser Glu
        355                 360                 365

Val Leu Ala Ser Val Phe Pro Ala Gln Asp Lys Pro Gly Glu Leu Gln
    370                 375                 380

Ala Thr Leu Asp His Thr Gly His Thr Ser Ser Lys Ser Leu Pro Asn
385                 390                 395                 400

Phe Pro Asn Thr Ser Ala Thr Ala Asn Ala Thr Gly Gly Arg Ala Leu
                405                 410                 415

Ala Leu Gln Ser Ser Leu Pro Gly Ala Glu Gly Pro Asp Lys Pro Ser
            420                 425                 430

Val Val Ser Gly Leu Asn Ser Gly Pro Gly His Val Trp Gly Pro Leu
        435                 440                 445

Leu Gly Leu Leu Leu Leu Pro Pro Leu Val Leu Ala Gly Ile Phe
    450                 455                 460
```